(12) United States Patent
Sepetka et al.

(10) Patent No.: US 8,105,333 B2
(45) Date of Patent: *Jan. 31, 2012

(54) SYSTEMS, METHODS AND DEVICES FOR REMOVING OBSTRUCTIONS FROM A BLOOD VESSEL

(75) Inventors: Ivan Sepetka, Los Altos, CA (US); Martin Dieck, Cupertino, CA (US); Son Gia, San Jose, CA (US); John Miller, Redwood City, CA (US); Ryan Pierce, Mountain View, CA (US); Maria Aboytes, Palo Alto, CA (US); Tiffany Tran Ngo, San Jose, CA (US); Dan Nguyen, San Jose, CA (US); Emily Vu, San Jose, CA (US)

(73) Assignee: Concentric Medical, Inc., Mountain View, CA (US)

( * ) Notice: Subject to any disclaimer, the term of this patent is extended or adjusted under 35 U.S.C. 154(b) by 783 days.

This patent is subject to a terminal disclaimer.

(21) Appl. No.: 12/008,718

(22) Filed: Jan. 11, 2008

(65) Prior Publication Data

US 2008/0188885 A1     Aug. 7, 2008

Related U.S. Application Data

(63) Continuation of application No. 11/038,906, filed on Jan. 18, 2005, now Pat. No. 7,534,252, which is a continuation of application No. 10/055,714, filed on Jan. 22, 2002, now Pat. No. 7,285,126.

(51) Int. Cl.
*A61B 17/24* (2006.01)

(52) U.S. Cl. ........................................ 606/113; 606/127

(58) Field of Classification Search ................. 606/113, 606/114, 127, 159, 200
See application file for complete search history.

(56) References Cited

U.S. PATENT DOCUMENTS

| | | |
|---|---|---|
| 3,868,956 A | 3/1975 | Alfidi et al. |
| 3,996,938 A | 12/1976 | Clark, III |
| 4,655,771 A | 4/1987 | Wallsten |
| 4,706,671 A | 11/1987 | Weinrib |
| 4,807,626 A | 2/1989 | McGirr |
| 4,873,978 A | 10/1989 | Ginsburg |
| 4,890,611 A | 1/1990 | Monfort et al. |
| 4,969,891 A | 11/1990 | Gewertz |
| 4,994,069 A | 2/1991 | Ritchart et al. |
| 4,998,539 A | 3/1991 | Delsanti |
| 5,011,488 A * | 4/1991 | Ginsburg ............ 606/159 |
| 5,054,501 A | 10/1991 | Chuttani et al. |
| 5,071,407 A | 12/1991 | Termin et al. |
| 5,256,146 A | 10/1993 | Ensminger et al. |
| 5,514,176 A | 5/1996 | Bosley, Jr. |
| 5,527,326 A | 6/1996 | Hermann et al. |
| 5,549,626 A | 8/1996 | Miller et al. |
| 5,562,698 A | 10/1996 | Parker |
| 5,688,234 A | 11/1997 | Frisbie |

(Continued)

FOREIGN PATENT DOCUMENTS

AU     758524     3/2003

(Continued)

*Primary Examiner* — Kevin T Truong
(74) *Attorney, Agent, or Firm* — Jens E. Hoekendijk

(57) ABSTRACT

Devices and methods for removing an obstruction from a blood vessel are described. The devices are deployed in a collapsed condition and are then expanded within the body. The devices are then manipulated to engage and remove the obstruction.

2 Claims, 50 Drawing Sheets

U.S. PATENT DOCUMENTS

| | | | |
|---|---|---|---|
| 5,702,413 | A | 12/1997 | Lafontaine |
| 5,817,104 | A | 10/1998 | Bilitz et al. |
| 5,895,398 | A | 4/1999 | Wensel et al. |
| 6,179,859 | B1 * | 1/2001 | Bates et al. .................... 606/200 |
| 6,245,089 | B1 * | 6/2001 | Daniel et al. .................. 606/200 |
| 6,375,668 | B1 | 4/2002 | Gifford et al. |
| 6,425,909 | B1 | 7/2002 | Dieck et al. |
| 6,436,112 | B2 | 8/2002 | Wensel et al. |
| 6,485,497 | B2 | 11/2002 | Wensel et al. |
| 6,494,884 | B2 | 12/2002 | Sepetka et al. |
| 6,350,935 | B1 | 3/2003 | Wensel et al. |
| 6,663,650 | B2 | 12/2003 | Sepetka et al. |
| 6,692,508 | B2 | 2/2004 | Wensel et al. |
| 6,692,509 | B2 | 2/2004 | Wensel et al. |
| 6,730,104 | B1 | 5/2004 | Sepetka et al. |
| 6,746,468 | B1 | 6/2004 | Sepetka et al. |
| 6,824,545 | B2 | 11/2004 | Sepetka et al. |
| 6,890,341 | B2 | 5/2005 | Dieck et al. |
| 6,905,503 | B2 | 6/2005 | Gifford et al. |
| 7,058,456 | B2 | 6/2006 | Sepetak et al. |
| 7,285,126 | B2 | 10/2007 | Sepetka et al. |
| 7,534,252 | B2 | 5/2009 | Sepetka et al. |

FOREIGN PATENT DOCUMENTS

| | | |
|---|---|---|
| AU | 773570 | 9/2004 |
| AU | 2003204826 | 11/2006 |
| JP | S60-189973 | 8/1985 |
| JP | 02-077245 | 3/1990 |
| JP | H5-179916 | 5/1995 |

* cited by examiner

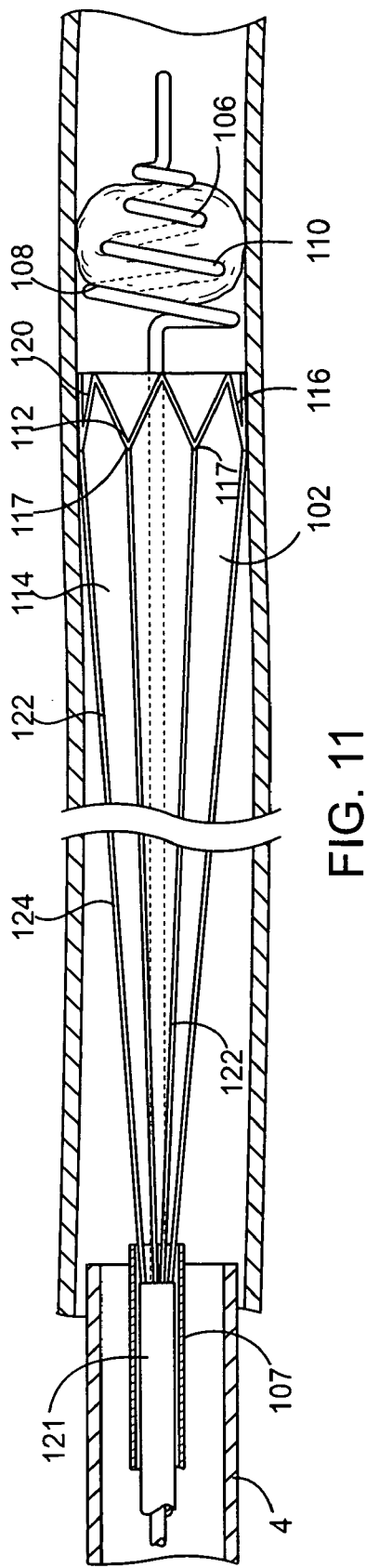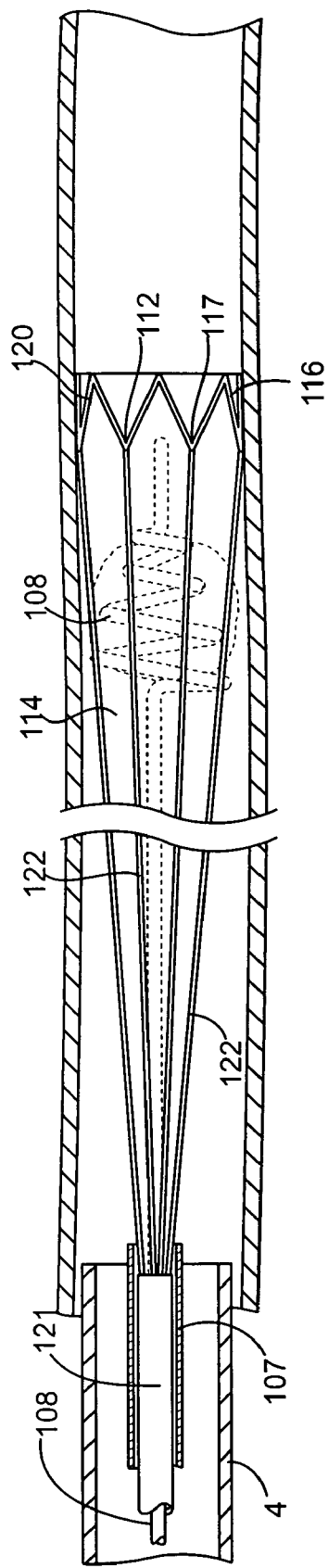

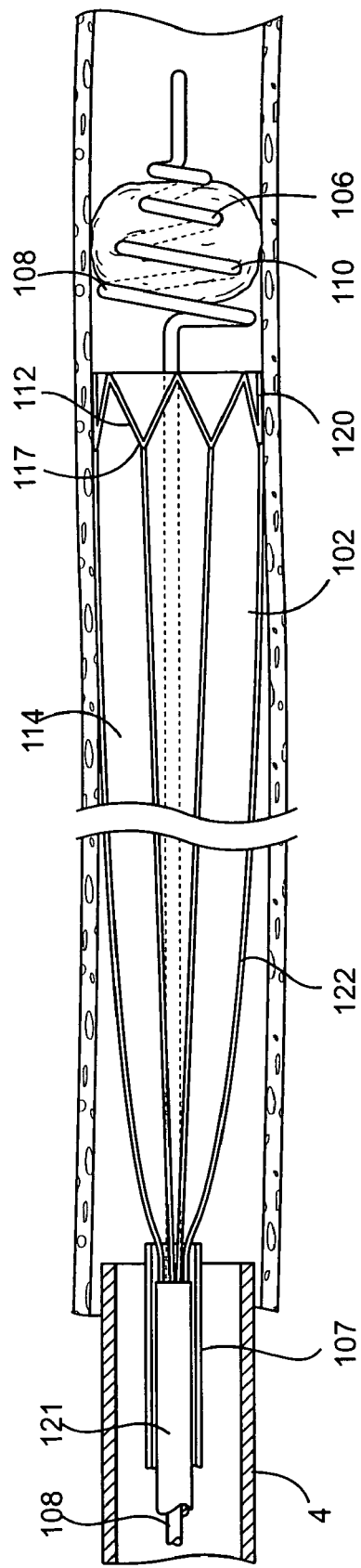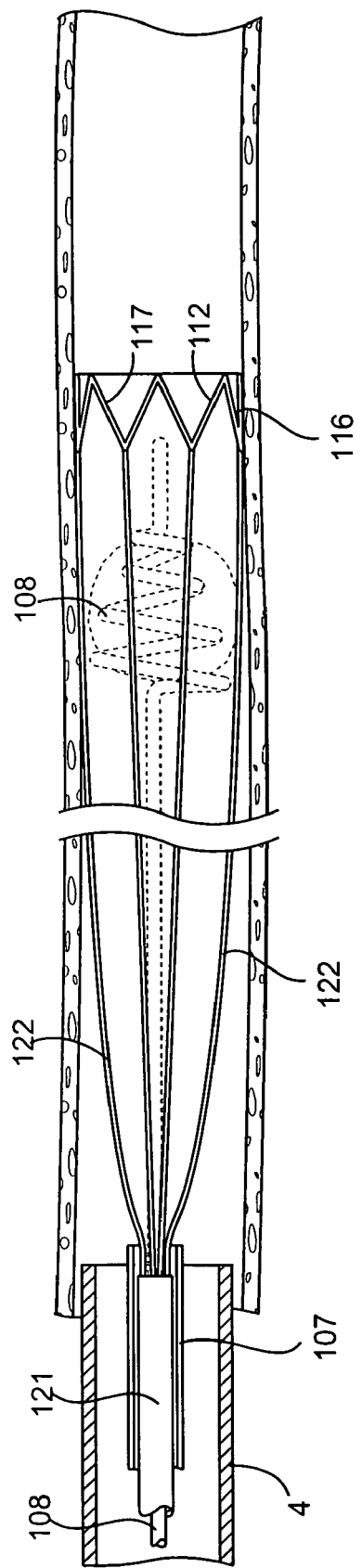
FIG. 23
FIG. 24

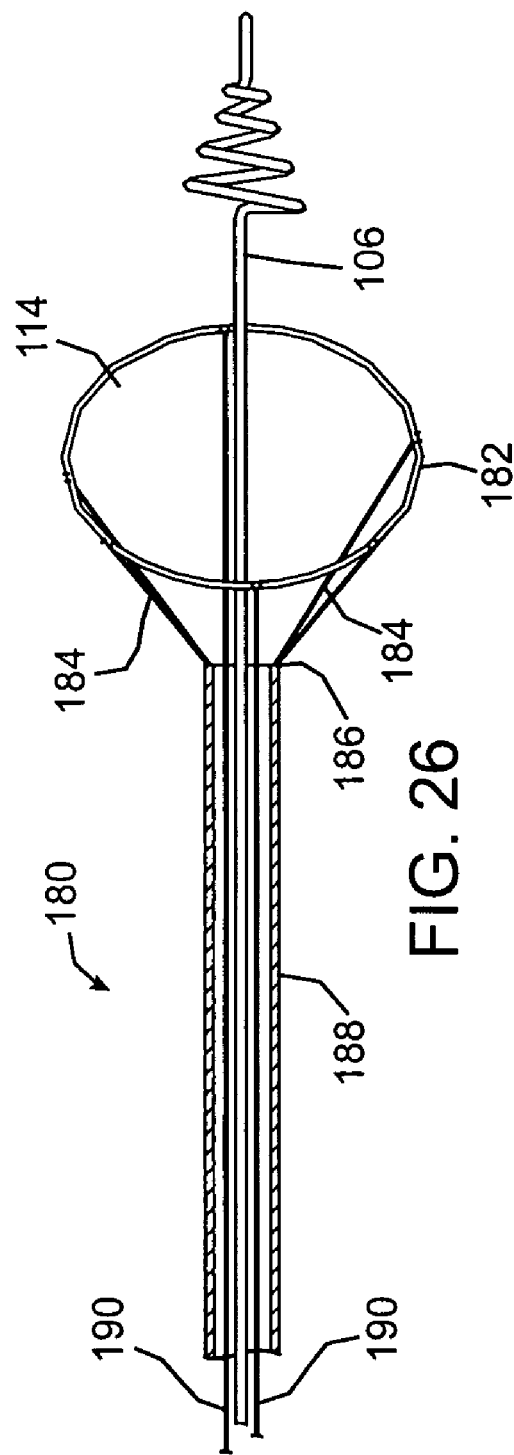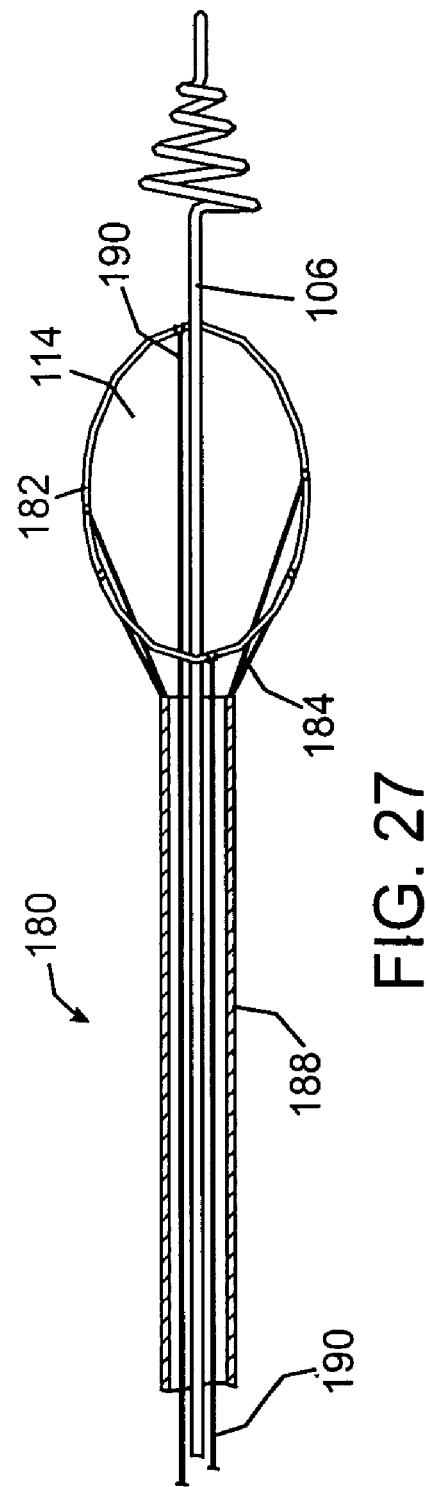

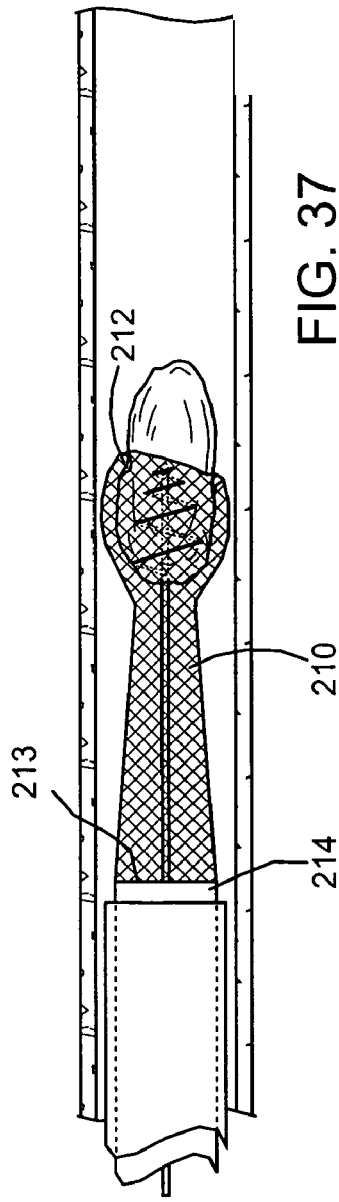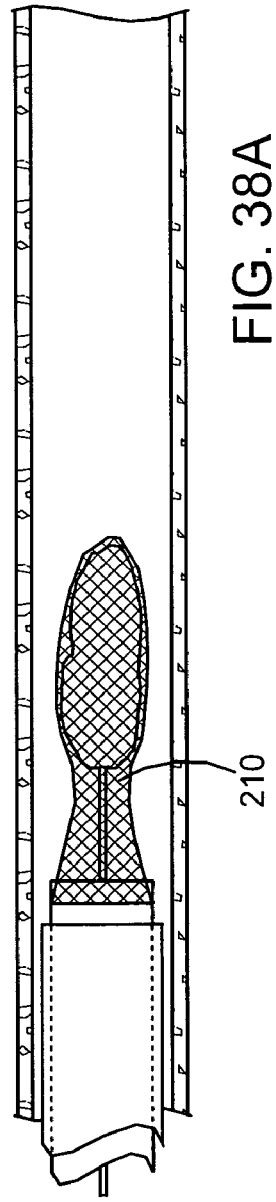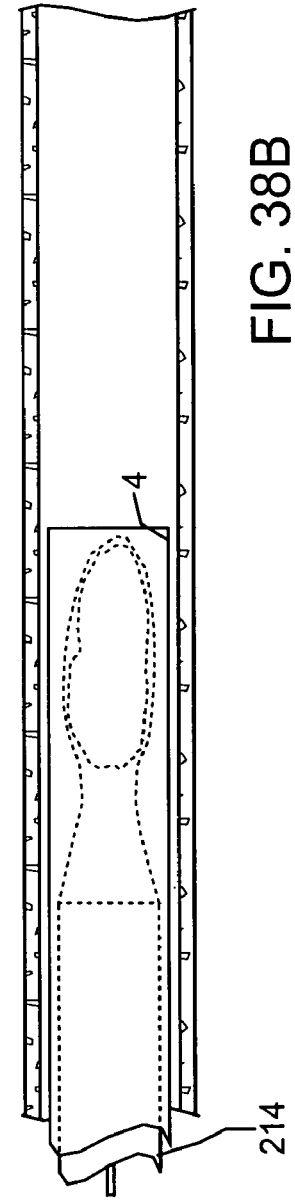

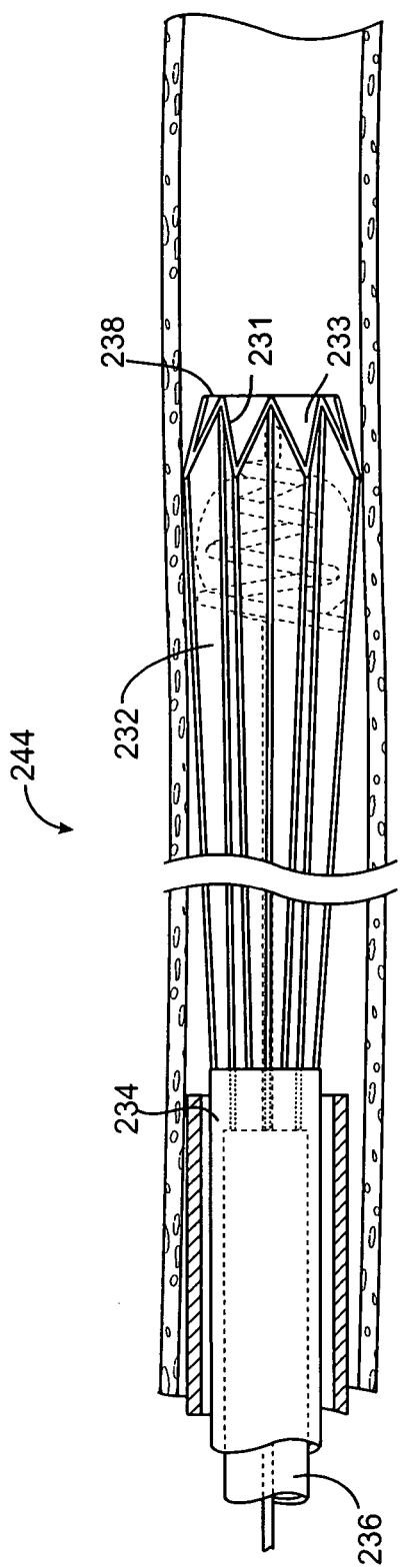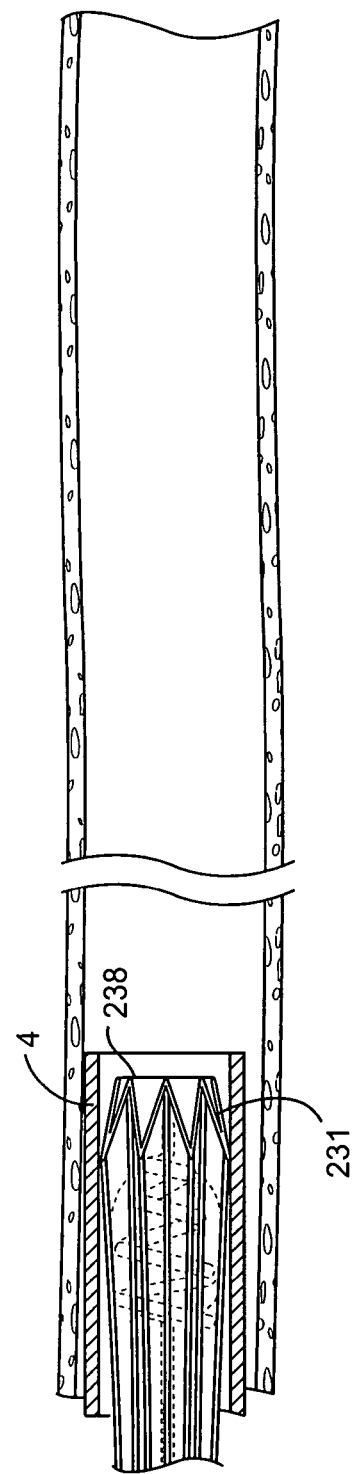
FIG. 42A
FIG. 42B

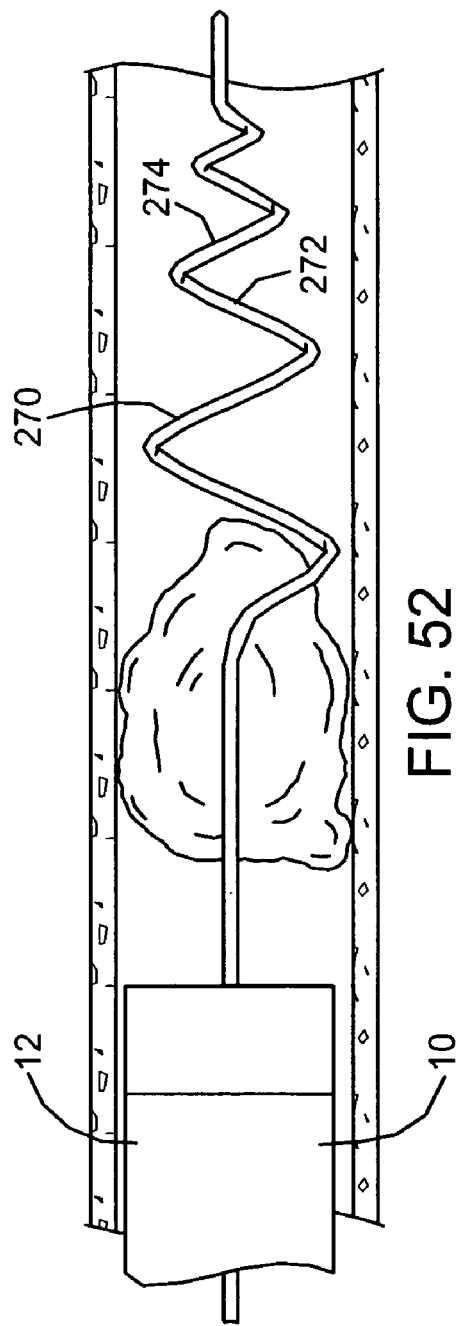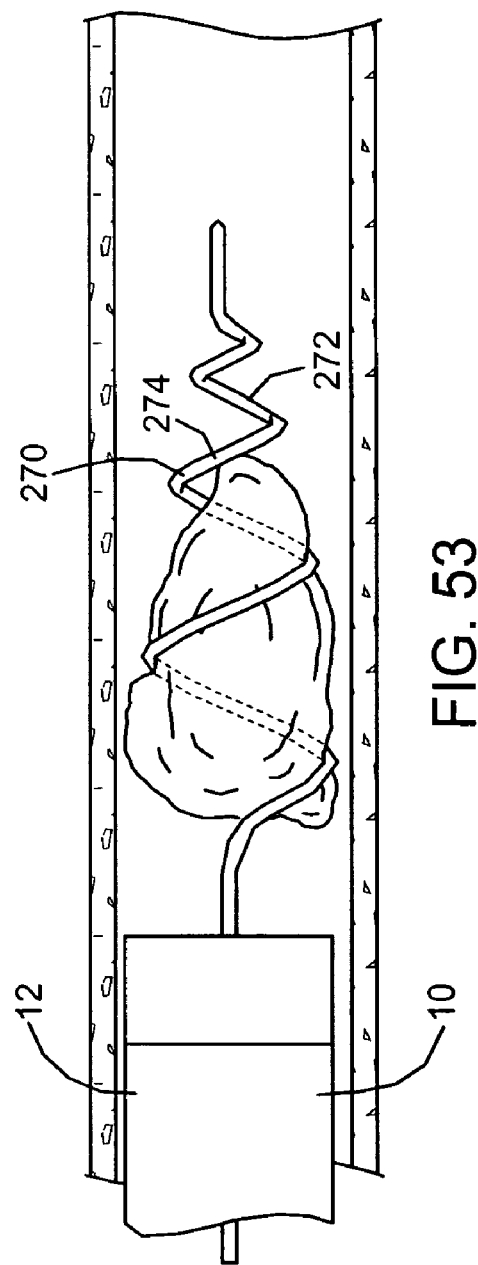

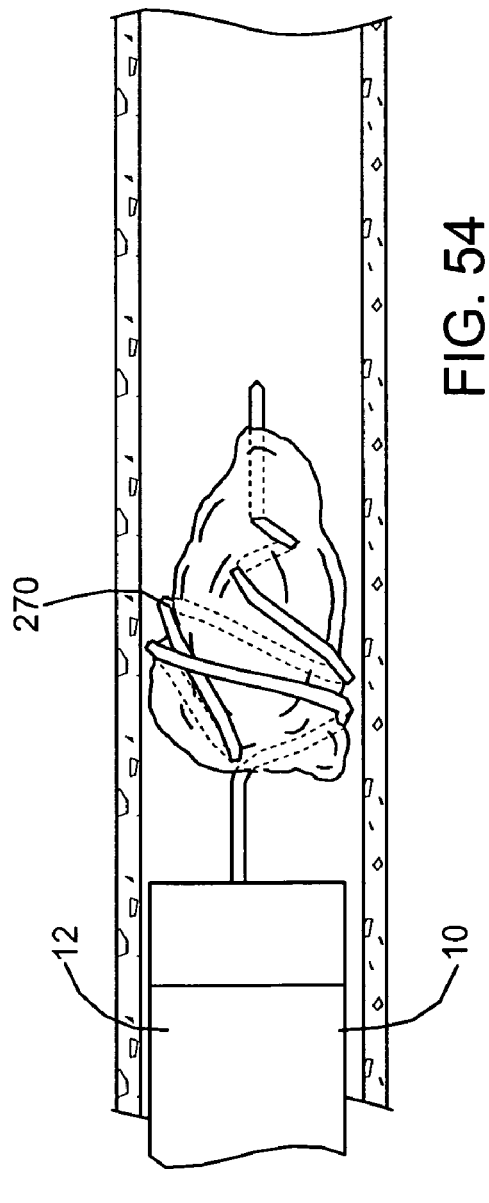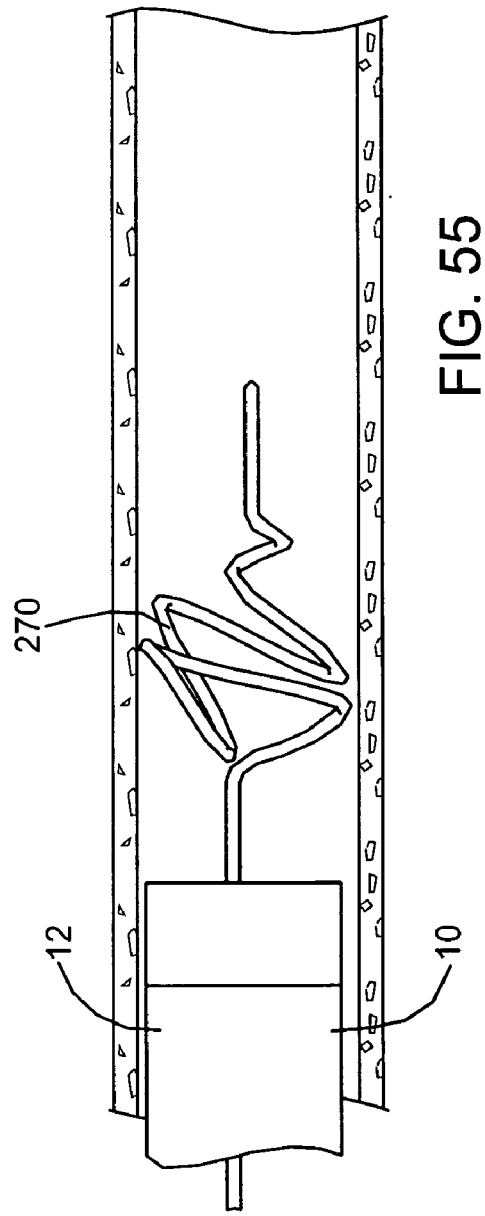

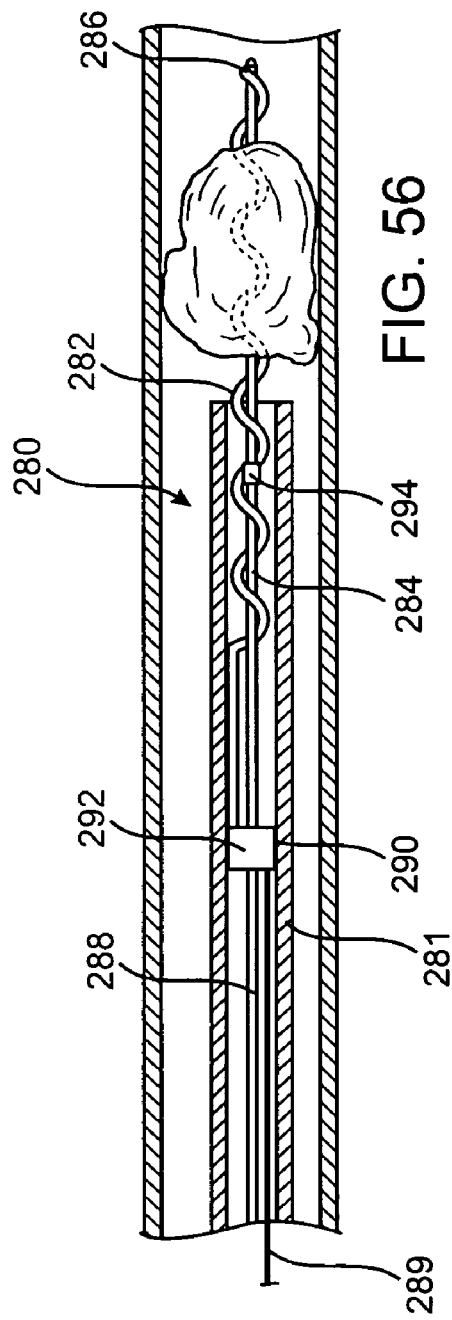
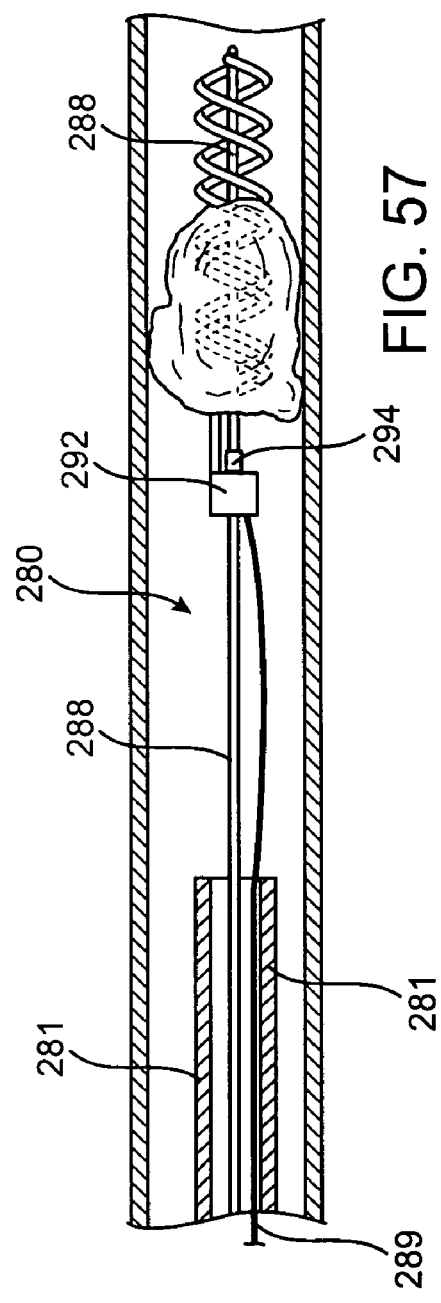

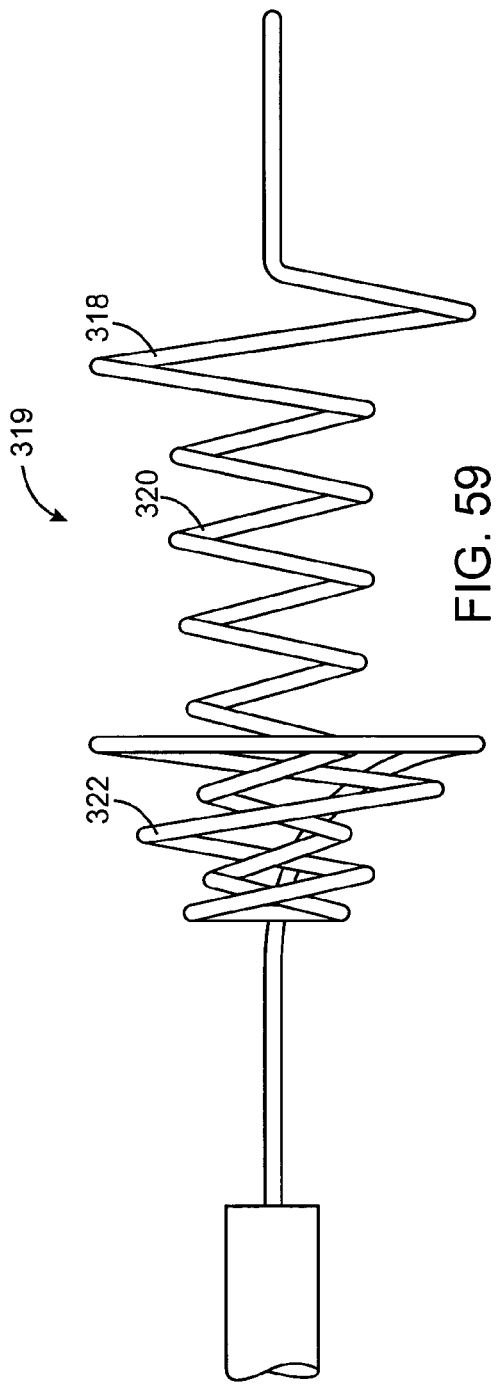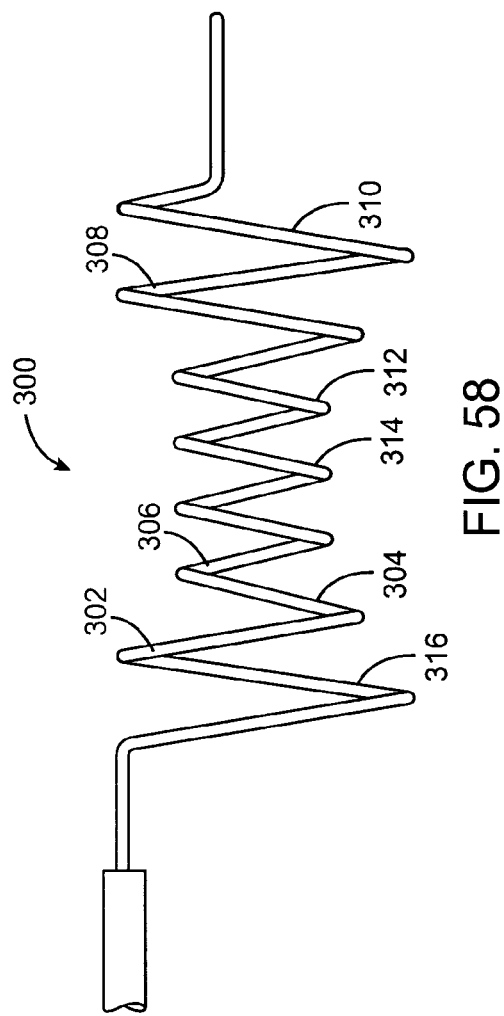
FIG. 59
FIG. 58

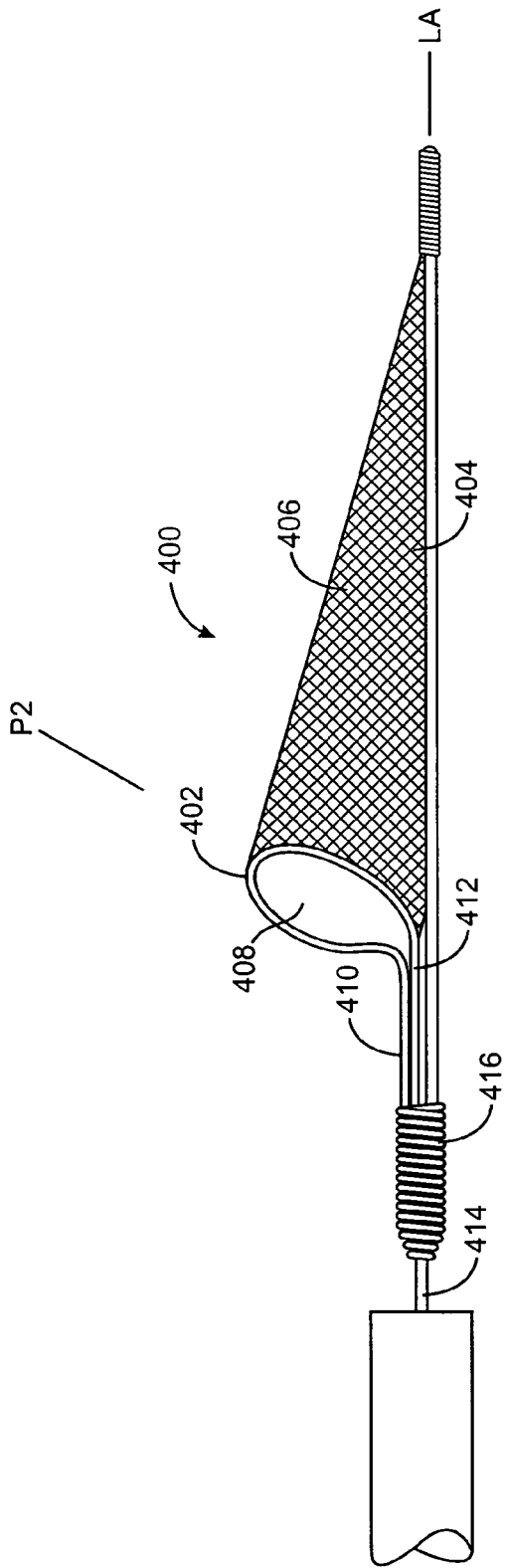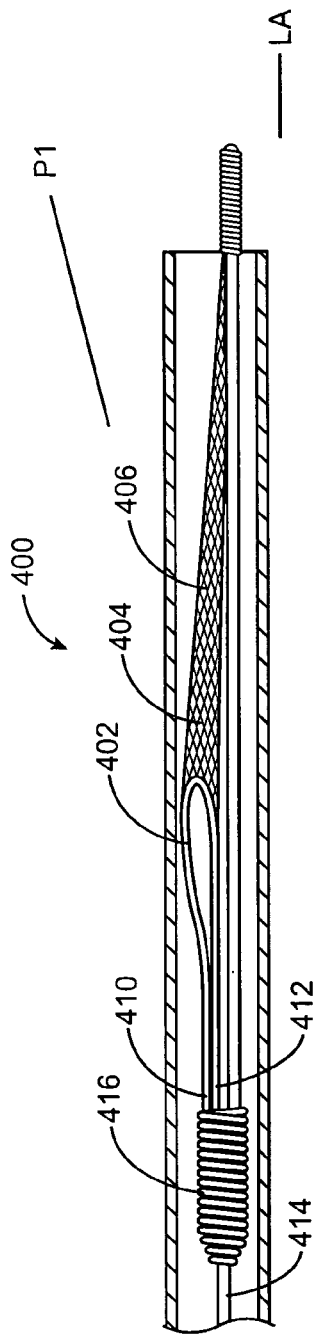
FIG. 80
FIG. 81

SYSTEMS, METHODS AND DEVICES FOR REMOVING OBSTRUCTIONS FROM A BLOOD VESSEL

CROSS-REFERENCE TO RELATED APPLICATIONS

The present application is a continuation of Application Ser. No. 11/038,906, filed Jan. 18, 2005, now U.S. Pat. No. 7,534,252 which is a continuation of Application Ser. No. 10/055,714, filed Jan. 22, 2002, now U.S. Pat. No. 7,285,126, the full disclosures of which are incorporated herein by reference for all purposes.

BACKGROUND OF THE INVENTION

Field of the Invention

The present invention is directed to methods and devices for removing obstructions from blood vessels. The device may be used to retrieve and remove clots and other biological obstructions. The device may also be used to retrieve embolic coils and the like which have been misplaced or have migrated to an undesirable location.

One such obstruction removal device is disclosed in U.S. Pat. No. 5,895,398 which is hereby incorporated by reference. The device has an expandable engaging member which is introduced into the blood vessel to engage the obstruction for removal.

The present invention is also directed to devices, systems and methods which use an expandable capture element when removing obstructions from a blood vessel. One such system for removing obstructions in a blood vessel is described in U.S. Pat. No. 5,102,415 to Guenther et al. The system described in U.S. Pat. No. 5,102,415 has a balloon catheter and a catheter having an expandable tip which receives the obstruction. The balloon catheter is passed through the obstruction while the balloon is deflated. The balloon is then inflated and the tip of the catheter is expanded. The balloon is then moved proximally so that the obstruction is pulled into the expanded tip of the catheter. A problem with the system of U.S. Pat. No. 5,102,415 is that the interaction between the balloon catheter and the leading edge of the catheter may tend to shear off portions of the obstruction. This can cause obvious problems when working in sensitive vascular areas.

The present invention is directed to additional devices and methods for removing obstructions in a blood vessel.

SUMMARY OF THE INVENTION

In accordance with the present invention, device and methods for removing obstructions are provided. In a first aspect of the invention, an obstruction removal device is provided which has an obstruction engaging element extending from an insertion element. The engaging element is movable from a collapsed position to an expanded position. The engaging element forms coils having varying diameter wherein the coils at a distal portion are larger than coils at an intermediate portion. The distal portion forms a relatively closed structure which prevents the obstruction, or any part thereof, from migrating downstream. The distal portion is expanded distal to the obstruction while the proximal portion engages and holds the obstruction.

In another aspect of the present invention, another obstruction removal device is provided which has at least one closed loop and preferably two closed loops. The closed loop provides an advantage when advanced through a catheter or sheath in that the closed loop produces opposing radial forces on the catheter or sheath through which the loop is advanced. In this manner, the obstruction removal device can be advanced more easily through the catheter or sheath to prevent binding or kinking of the device during advancement. In a preferred embodiment, the obstruction removal device has two loops of varying diameter with the distal loop having a larger diameter. Each of the loops lie in a plane with the planes of the two loops preferably being perpendicular to one another.

In another aspect of the invention, another obstruction removal device is provided which has wound sections formed by one or more filaments which are separated by sections substantially free of the filaments. The intermittent wound sections provide discrete portions where the obstruction can be engaged. In an embodiment, the wound sections can slide on the core element to provide flexibility when advancing the obstruction removal device. The wound sections and sections free of filament are preferably about 1-5 mm long. The obstruction removal device preferably has at least three wound sections and more preferably at least five wound sections.

In still another aspect of the invention, another obstruction removal device is provided which has alternating large and small diameter portions. In a preferred embodiment, the obstruction removal device has at least four large diameter sections and three smaller diameter portions. The alternating large and small diameter portions may help to engage certain types of obstructions and can also help to prevent parts of the obstruction from breaking off and migrating downstream.

Any of the obstruction removal devices described herein may also be used with a source of power coupled to the obstruction removal device for use as described below. The source of power may simply produce a positive or negative charge or may be an RF energy source. The source of power may be used to help the obstruction removal device penetrate and engage the obstruction and may also be used to adhere the obstruction to the obstruction removal device as will be described. In a preferred embodiment, a negative charge is provided when advancing the obstruction removal device into the obstruction and a positive charge, or RF energy, is supplied to adhere the device to the obstruction.

The devices of the present invention may be manufactured in any suitable manner. In another aspect of the present invention, the obstruction removal device has a core element surrounded by a sheath. A strand, preferably about four strands, are positioned between the core element and the tube. The strand and the tube prevent any part of the obstruction removal device from breaking free should the core element fail. The strand and tube will hold the obstruction removal device together even if the core element breaks. The sheath is preferably flexible so that the sheath can undergo much larger deflections than the core element.

The obstruction removal devices of the present invention may also be advanced through a guide catheter having a flow restricting element which is preferably a balloon but may be any other suitable structure. The flow restricting element is expanded to reduce blood flow through the obstructed vessel to minimize the likelihood that the obstruction will migrate downstream.

In another aspect of the invention, a system is provided which has an expandable capture element and an obstruction engaging device which together work to remove an obstruction from a blood vessel. The capture element is advanced through the patient in a collapsed position and is expanded when at the desired location. The obstruction engaging device preferably has one or more filaments which provide a relatively flexible interaction between the engaging device and the capture element. This provides advantages over the use of a balloon catheter as described in greater detail below. The obstruction engaging device preferably has 1-4 filaments and more preferably 1-2 filaments. Of course, the obstruction engaging device may have more filaments without departing from various aspects of the invention and, in fact, the device may form a filter which further helps to prevent portions of the obstruction from being carried downstream.

The capture element is preferably naturally biased toward the expanded position although the capture element may also be manually actuated as described below. The capture element has a support structure with a flexible cover attached thereto. The support structure preferably has a closed loop which opens the distal end of the cover. The loop is preferably integrally formed and has a number of integrally formed hinges which deflect when the loop is expanded and collapsed. The hinges are preferably V-shaped although other shapes may be used. A plurality of struts extend proximally from the loop.

The capture element may also be expanded by the user so that the user may select the appropriate time for expansion of the capture element. In this manner, the user may advance the capture element to a suitable location for expansion. The user may also collapse the capture element before withdrawing the capture element into a catheter. The capture element has an actuator for opening and closing the capture element. The actuator may have a control arm and a stable arm although any suitable actuator may be used. The control arm is manipulated to expand and contract a loop at the distal end of the capture element. Alternatively, the actuator may be a tube which cinches the loop closed. In a specific embodiment, the capture element may also evert when moving to the expanded position.

The device of the present invention may be used in various different locations and for various different purposes. In one embodiment, the device may be used in connection with a guide catheter. When used with the guide catheter, the device may be expanded to slow or even stop blood flow when performing other procedures downstream of the guide catheter such as removing a clot or placing a stent.

Alternatively, the device may be passed through a conventional guide catheter so that the device may be introduced further into the vasculature. In this system, the capture element passes through the guide catheter. The obstruction engaging device is then used to engage the obstruction and move the obstruction into the capture element.

The present invention is also directed to methods and devices for removing an obstruction where the obstruction engaging element has a shape which traps the obstruction. In one aspect, the element extends proximally and then distally to ensnare the obstruction. The element may have such a shape naturally or may be moved into this shape by manipulating the element. For example, the element may be rotated in one or both directions to ensnare the obstruction. The element may have a portion which prolapses to capture the element as the element is manipulated.

In still another aspect of the invention, the capture element inverts when the obstruction is moved into the capture element. The obstruction is preferably engaged with an engaging element having a filament which ensnares the obstruction. The obstruction engaging element may be independent from the capture element or may be connected to the engaging element. The capture element inverts upon application of a compressive force to the inverting portion or upon any other suitable actuation force. The capture element preferably inverts when the compressive force is applied by either the obstruction or the engaging element.

The present invention is also directed to actuators for medical devices. In a first aspect, an actuator is provided which has an outer member and a plurality of fingers extending from the outer member. The fingers form an end that can be opened and closed by bending and straightening the fingers. The fingers may be bent by moving an inner member coupled to the fingers or by tensioning or releasing tension on a filament. The medical devices described above may be used for any suitable purpose including capture or containment of obstructions. For this purpose, the fingers or frame may be covered with the cover that forms an enclosure to hold the obstruction.

In another aspect, the medical device may have a frame that extends from inner and outer members. The frame forms an end that also opens and closes. The frame has a first set of connectors coupled to the outer member and a second set of connectors coupled to the inner member. The inner and outer members are movable relative to one another to open and close the end. The frame may be an integral structure with the structure being deformed when the end opens and closes. In still another aspect, the frame may be made of a shape memory material which regains either the closed or open position when heated or cooled. For example, the frame may be heated using electrical energy or other suitable source to actuate the frame.

These and other advantages of the invention will become apparent from the following description, drawings and claims.

BRIEF DESCRIPTION OF THE DRAWING FIGURES

FIG. 1 shows a system for removing an obstruction.
FIG. 2 shows the obstruction removal device in a collapsed condition.
FIG. 3 shows the obstruction removal device with a distal portion of the obstruction removal device expanded.
FIG. 4 shows the obstruction removal device with a proximal portion expanded to engage an obstruction.
FIG. 5 shows another obstruction removal device.
FIG. 6 shows yet another obstruction removal device.
FIG. 7 shows still another obstruction removal device.
FIG. 8 is an end view of the obstruction removal device of FIG. 7.
FIG. 9 is an exploded view showing a method of constructing an obstruction removal device.
FIG. 10 shows another system for removing an obstruction from a blood vessel.
FIG. 11 shows a capture element in an expanded position with an obstruction engaging element engaging an obstruction
FIG. 12 shows the obstruction moved into the capture element with the obstruction engaging element.
FIG. 13 shows the capture element collapsed and contained within a catheter.
FIG. 14 shows an alternative structure for the capture element.
FIG. 15 shows another capture element.
FIG. 16 shows a distal end of the capture element of FIG. 15.
FIG. 17 shows the support structure for the capture element of FIGS. 15 and 16.
FIG. 18 shows the capture element collapsed around the obstruction prior to withdrawal.
FIG. 19 shows the capture element contained within the catheter in an inverted position when collapsed.

FIG. 23 shows another capture element having a support structure which bows outward to preferentially close the distal end.

FIG. 24 shows the capture element of FIG. 23 with an obstruction contained within the capture element.

FIG. 26 shows yet another capture element in an expanded position.

FIG. 27 shows the capture element of FIG. 26 in a collapsed position.

FIG. 37 shows the obstruction partially contained within the capture element.

FIG. 38A shows the obstruction completely contained within the capture element.

FIG. 38B shows the inverting portion contained within another catheter such as the guide catheter for removal from the patient.

FIG. 42A shows the actuator of FIG. 40 with the distal end closed.

FIG. 42B shows the capture device withdrawn into another catheter.

FIGS. 43A-D show the frame coupled to inner and outer members.

Figure 44:
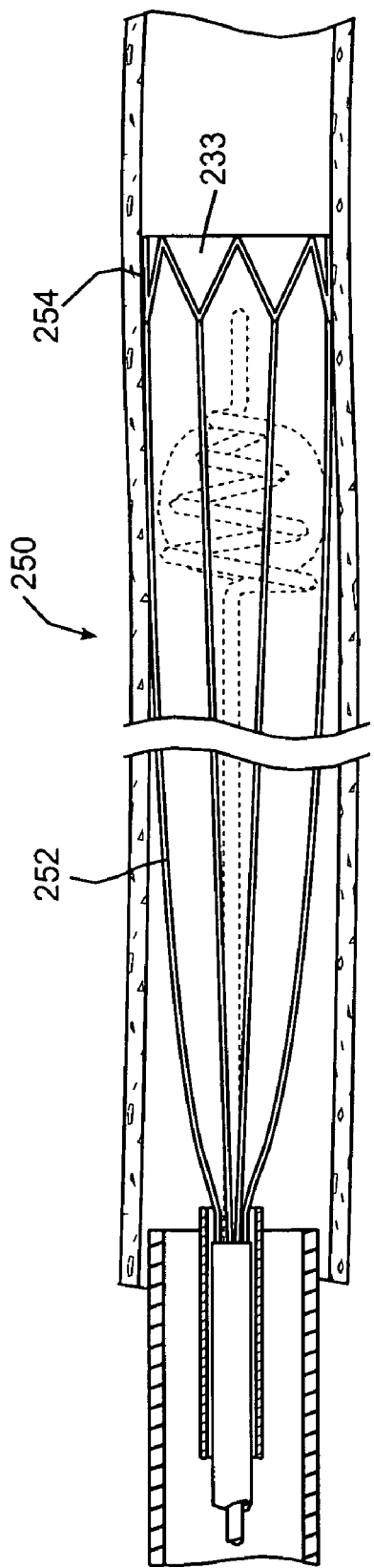

FIG. 44 shows another actuator having a frame made of a shape memory material.

Figure 45:
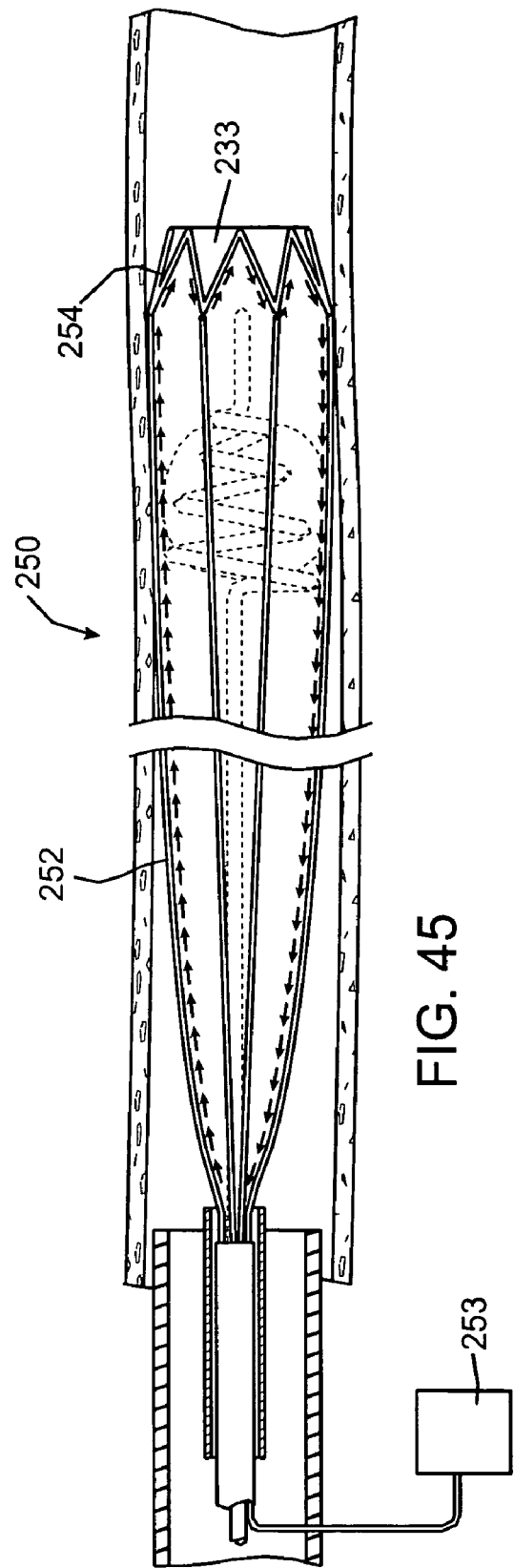

FIG. 45 shows the actuator of FIG. 43 with the distal end closed.

Figure 46:
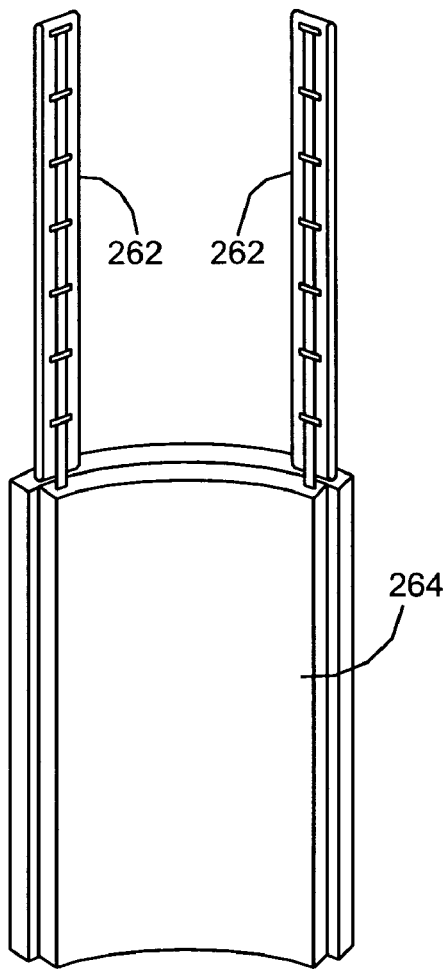

FIG. 46 shows still another actuator for a medical device.

Figure 47:
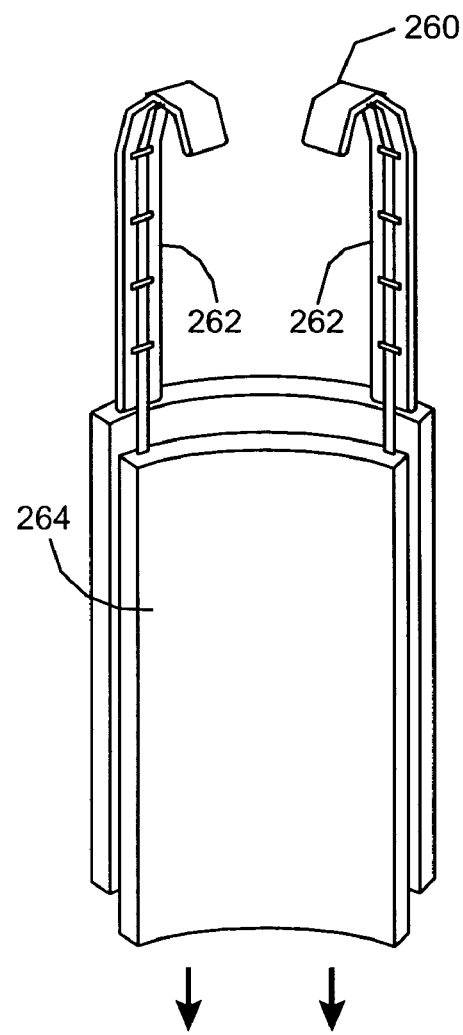

FIG. 47 shows the actuator of FIG. 46 with a plurality of fingers in a closed position.

Figure 48:
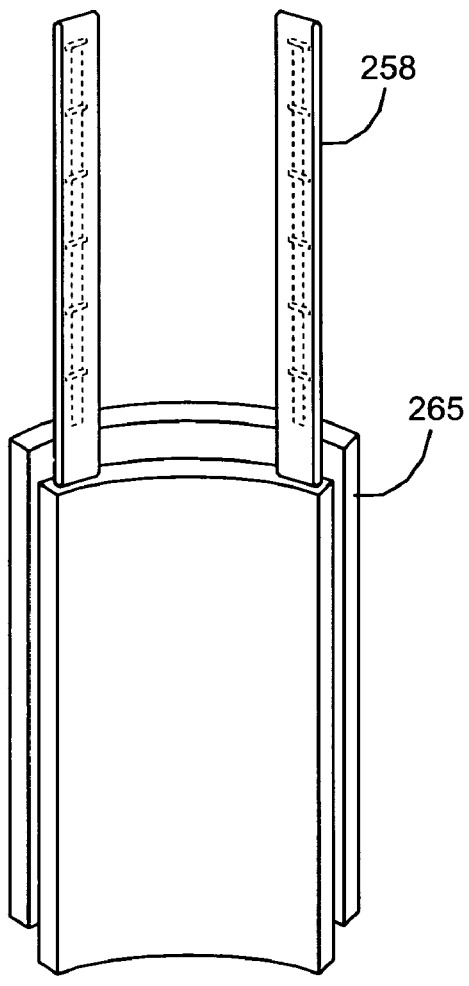

FIG. 48 shows an alternate embodiment of the medical device of FIGS. 45 and 46.

Figure 49:
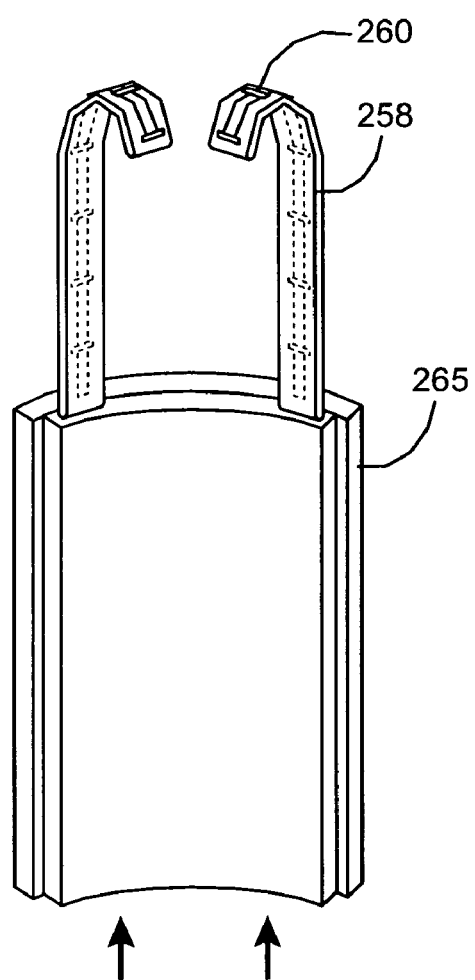

FIG. 49 shows the medical device of FIG. 48 with the fingers in a closed position.

Figure 50:
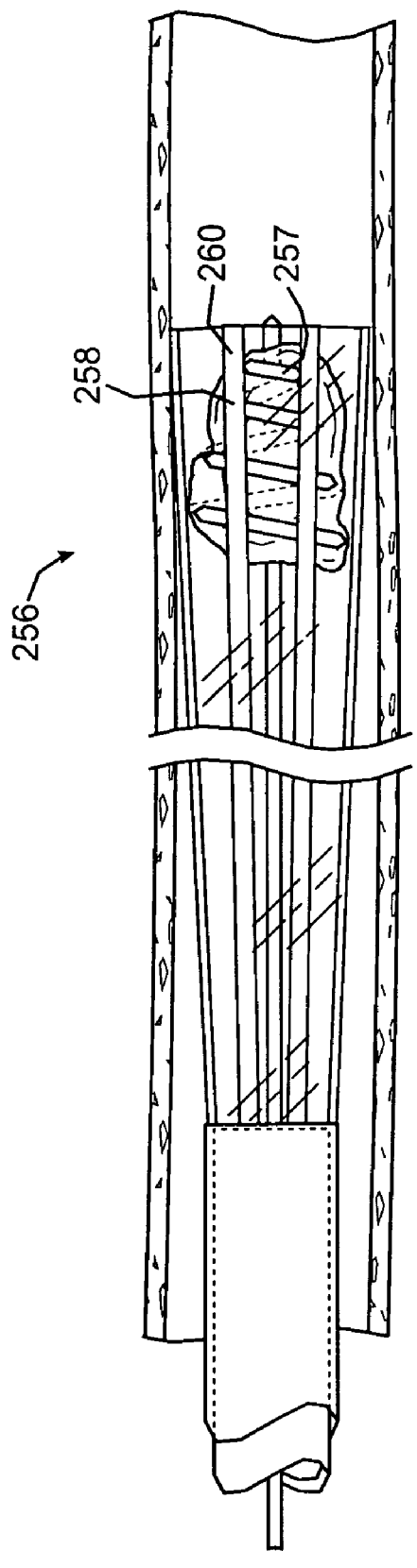

FIG. 50 shows the actuator of FIGS. 46-49 used to capture or remove an obstruction.

Figure 51:
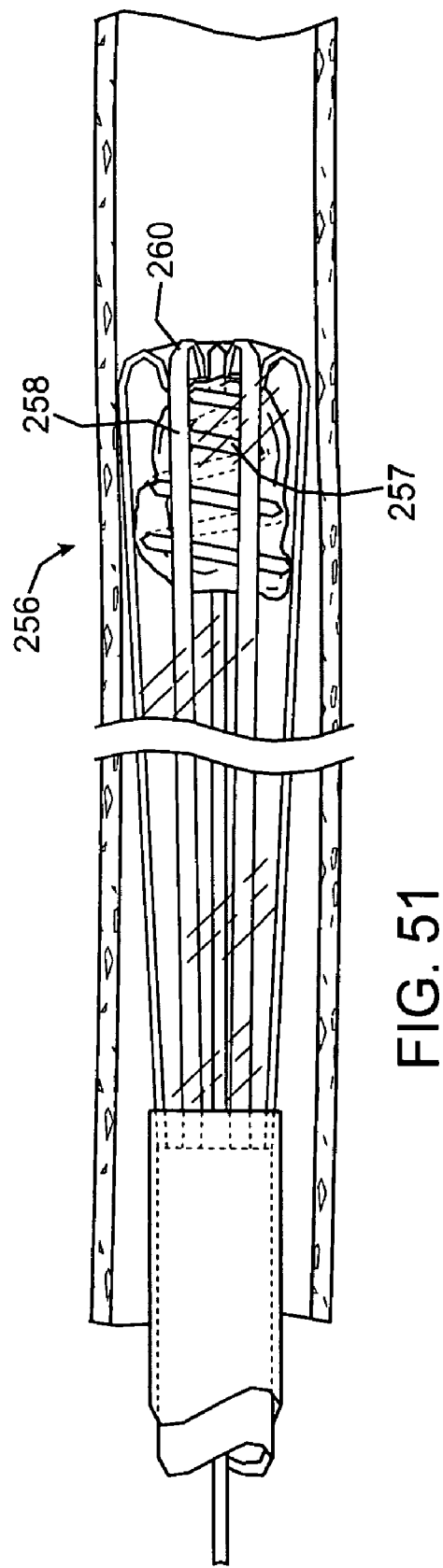

FIG. 51 shows the actuator of FIGS. 46-49 with the distal end closed to capture the obstruction.

FIG. 52 shows another obstruction engaging element.

FIG. 53 shows the obstruction engaging element of FIG. 52 with the element engaging an obstruction.

FIG. 54 shows the obstruction engaging element of FIGS. 52 and 53 with the element having a prolapsed portion.

FIG. 55 shows another obstruction engaging element in an expanded position.

FIG. 56 shows another device for removing an obstruction.

FIG. 57 shows the obstruction removing device of FIG. 56 expanded to engage the obstruction.

FIG. 58 shows another obstruction removing device in an expanded position.

FIG. 59 shows still another obstruction removing device.

Figure 60:
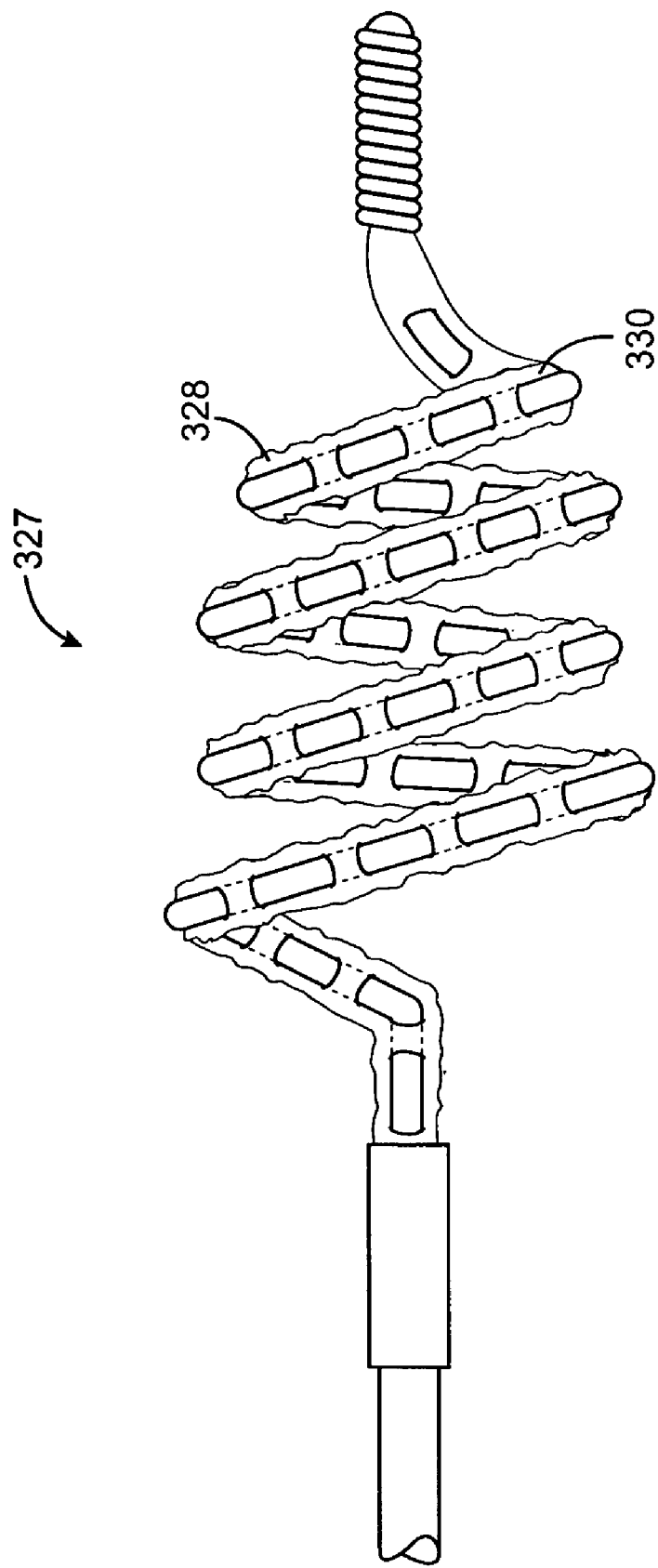

FIG. 60 shows yet another obstruction removing device.

Figure 61:
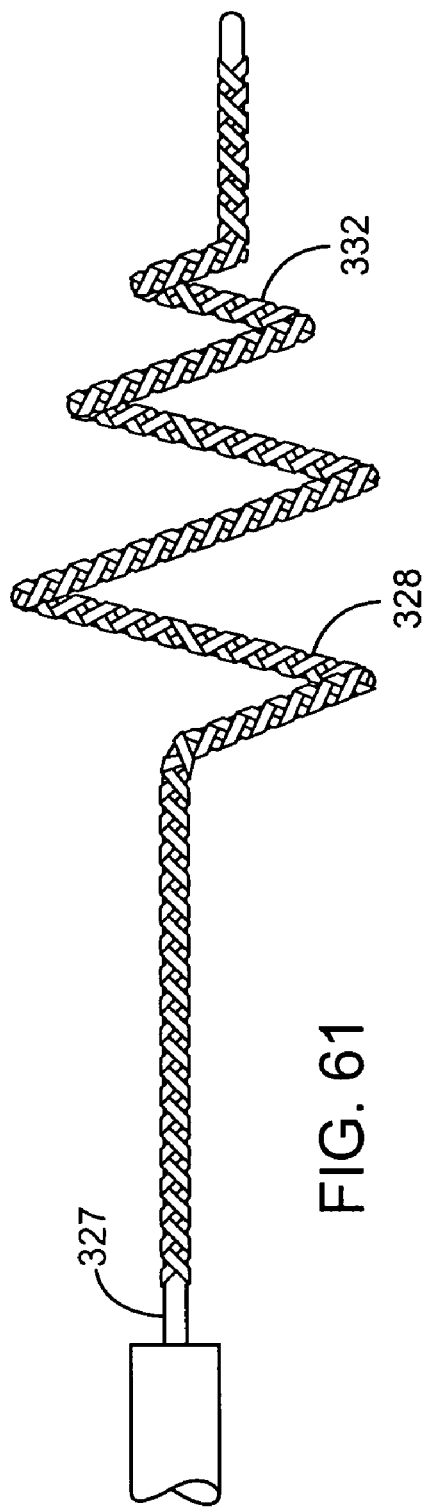

FIG. 61 shows another obstruction removing device with a braided cover.

Figure 62:
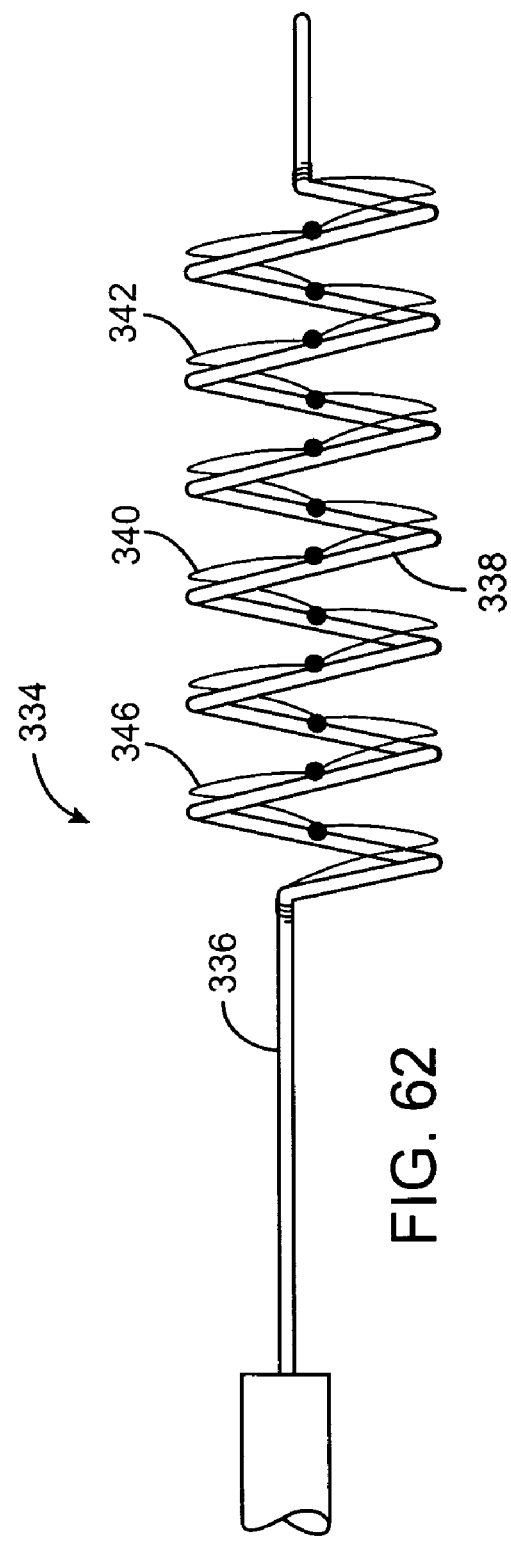

FIG. 62 shows an obstruction removing device with two side-by-side elements.

Figure 63:
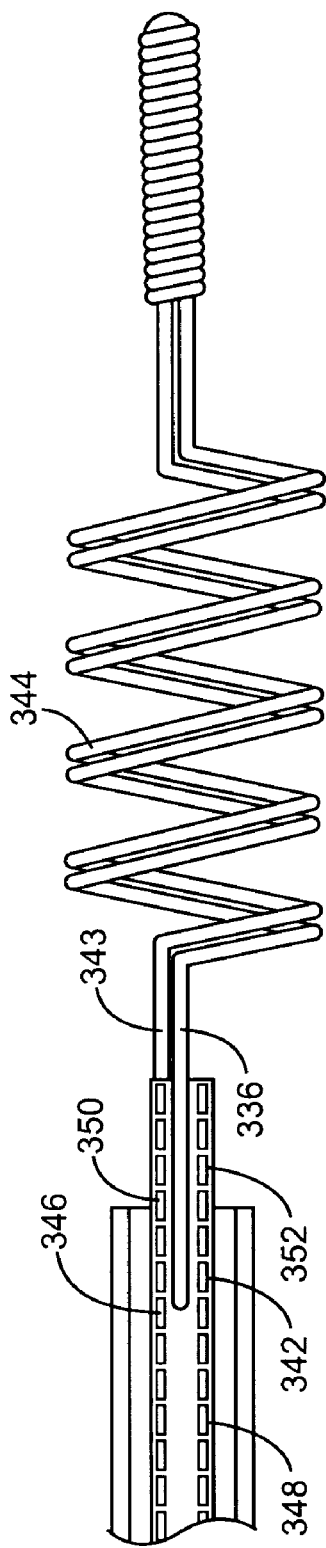

FIG. 63 shows another embodiment with side-by-side elongate elements.

Figure 64:
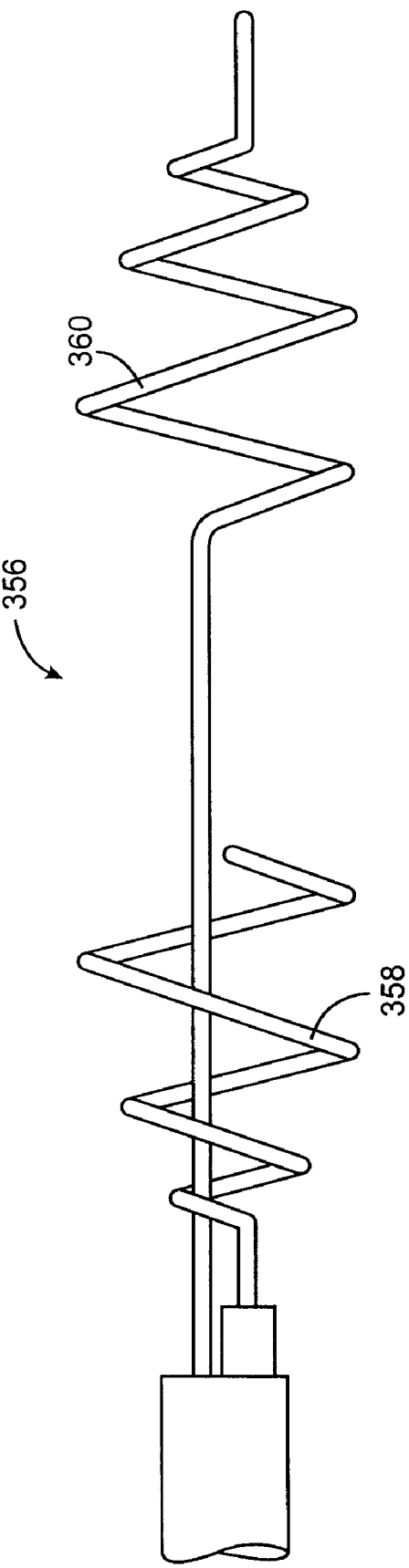

FIG. 64 shows an obstruction removing device having independently movable proximal and distal portions.

Figure 65:
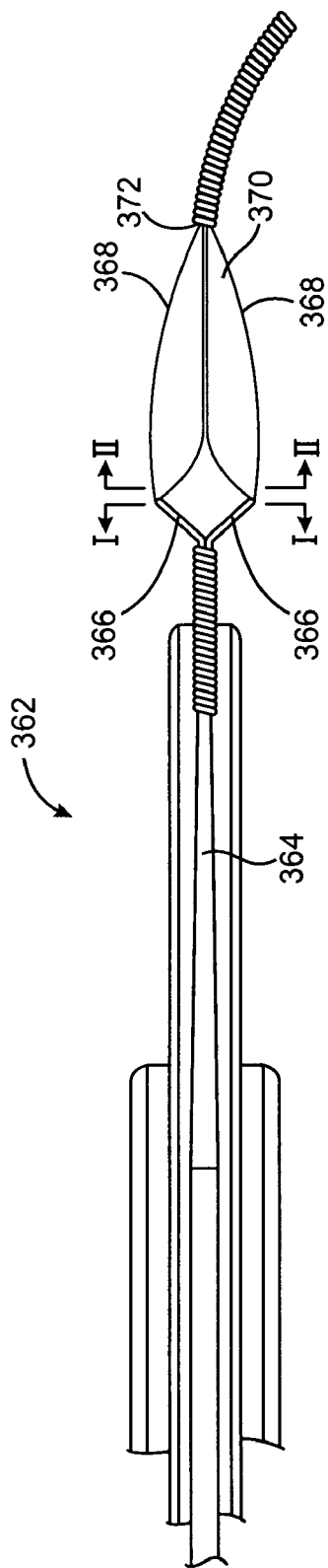

FIG. 65 shows still another obstruction removing device.

Figure 66:
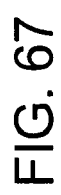

FIG. 66 is a cross-sectional view of FIG. 65 along line I-I.

Figure 67:
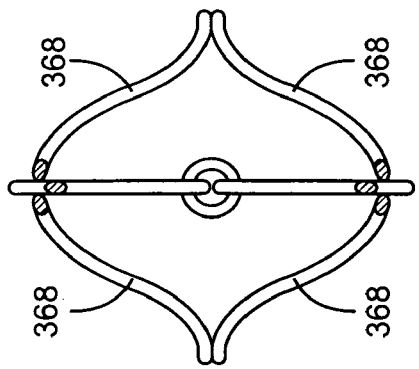

FIG. 67 is a cross-sectional view of FIG. 65 along line II-II.

Figure 68:
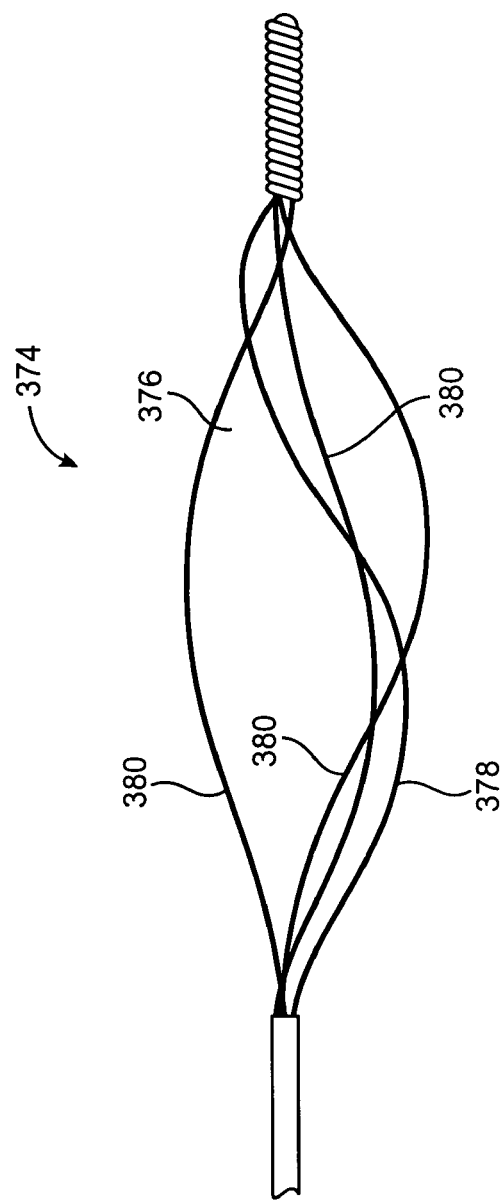

FIG. 68 shows another obstruction removing device.

Figure 69:
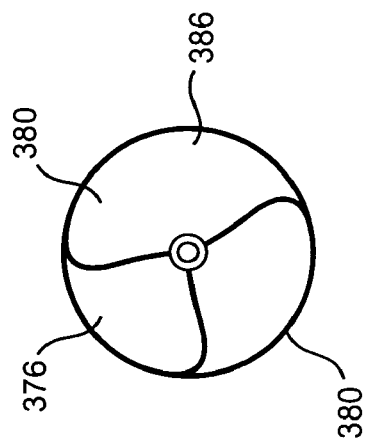

FIG. 69 is an end view of FIG. 68 showing a larger opening between some of the wires.

Figure 70:
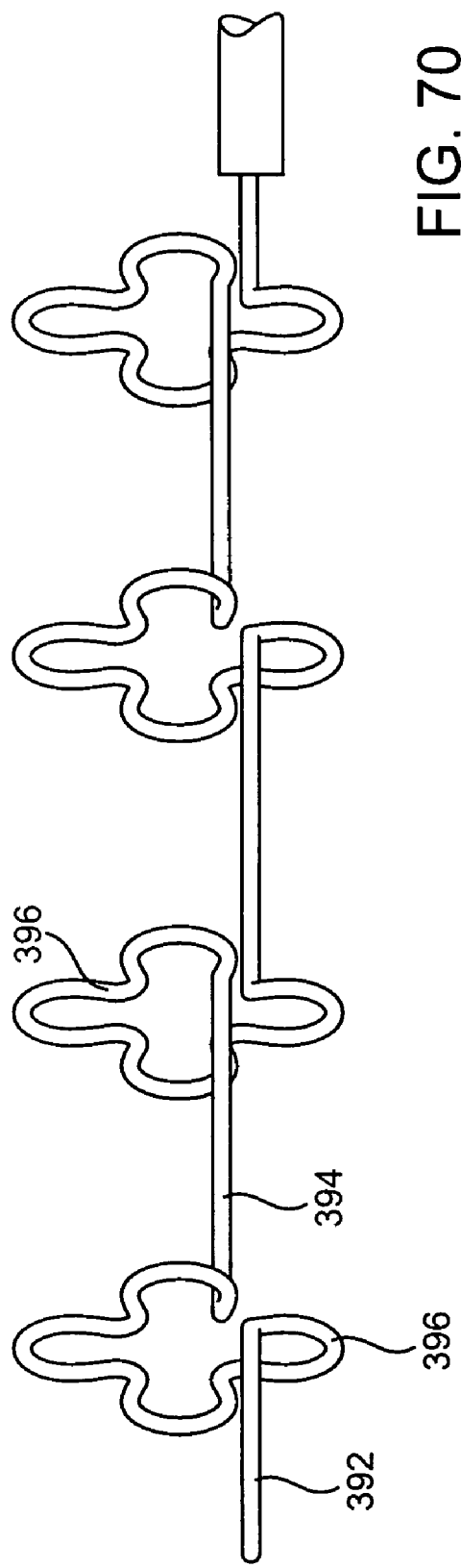

FIG. 70 shows another obstruction removing device.

Figure 71:
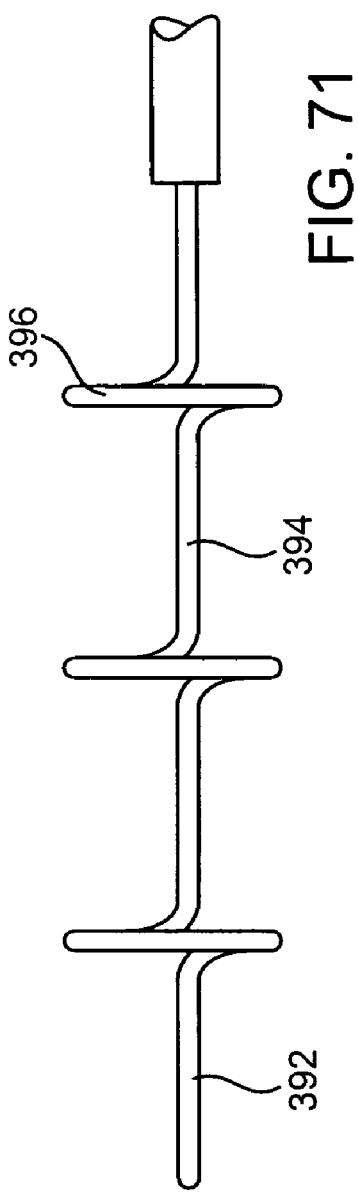

FIG. 71 is a side view of the device of FIG. 70.

Figure 72:
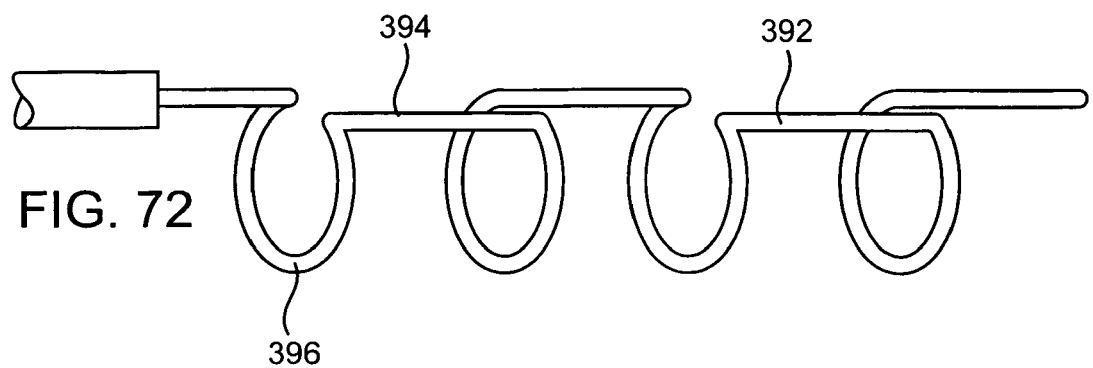

FIG. 72 shows another obstruction removing device.

Figure 73:
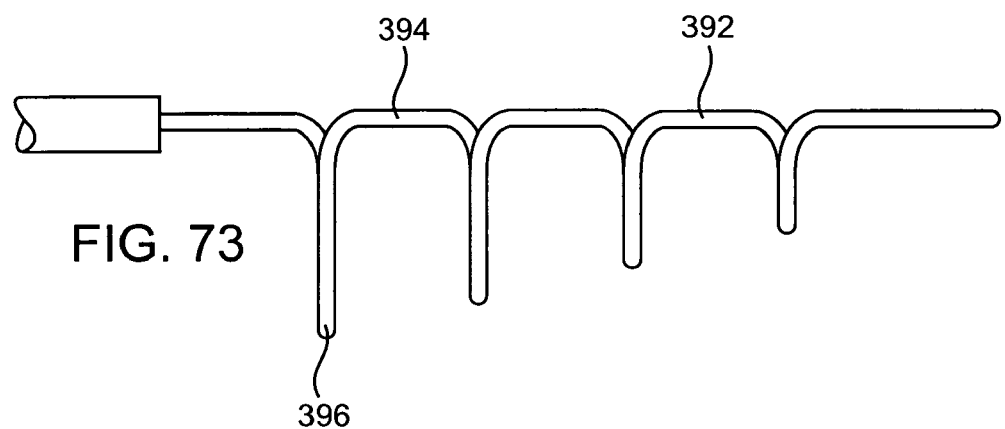

FIG. 73 is a side view of the device of FIG. 72.

Figure 74:
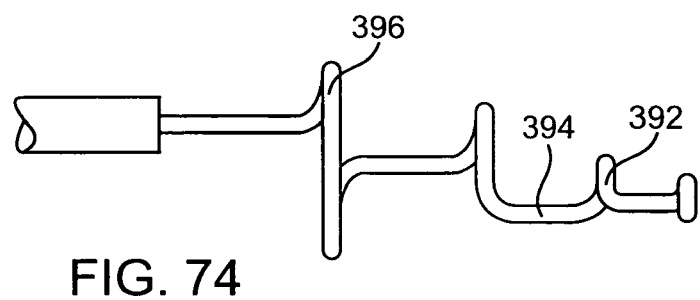

FIG. 74 is an alternative side view of the device of FIG. 72.

Figure 75:
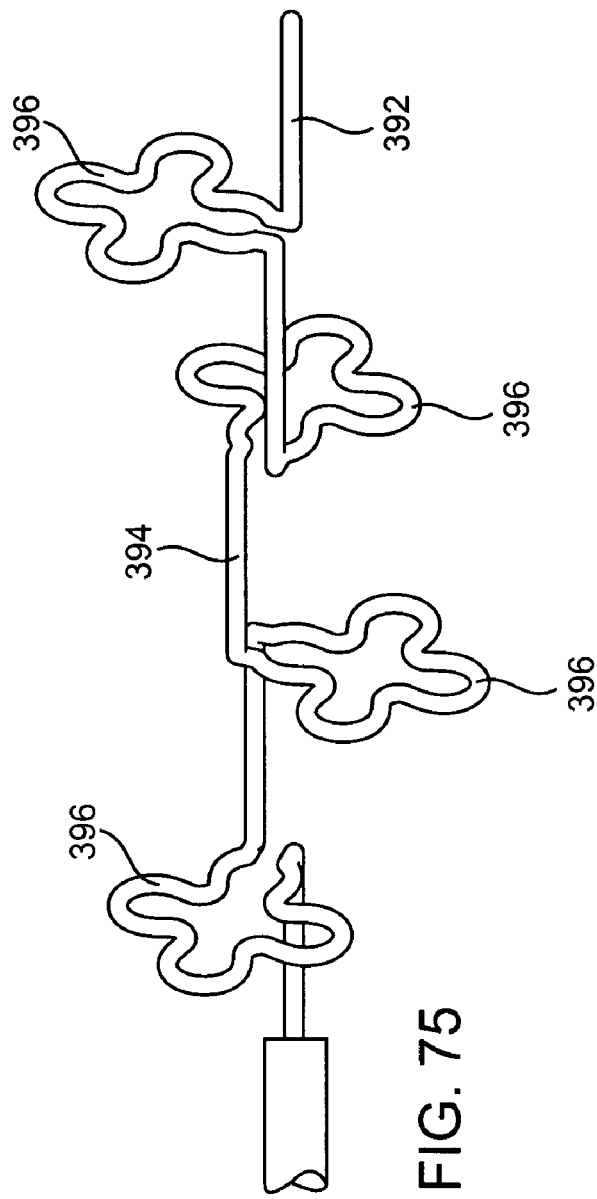

FIG. 75 shows another obstruction removing device.

Figure 76:
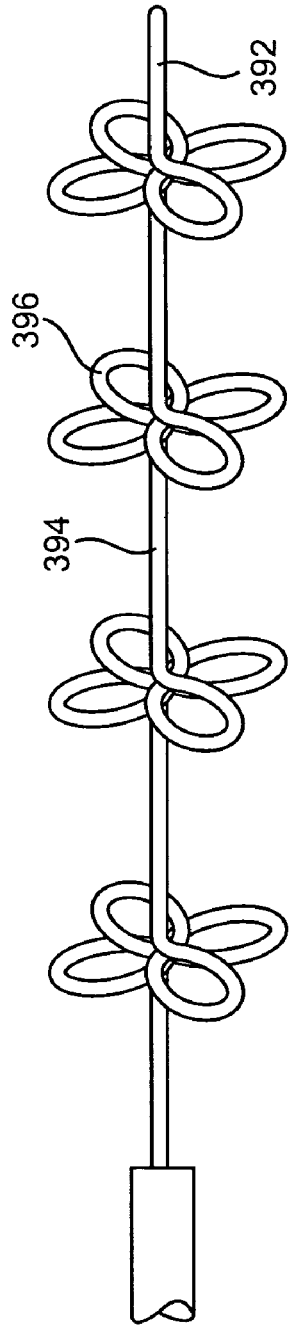

FIG. 76 shows another obstruction removing device.

Figure 77:
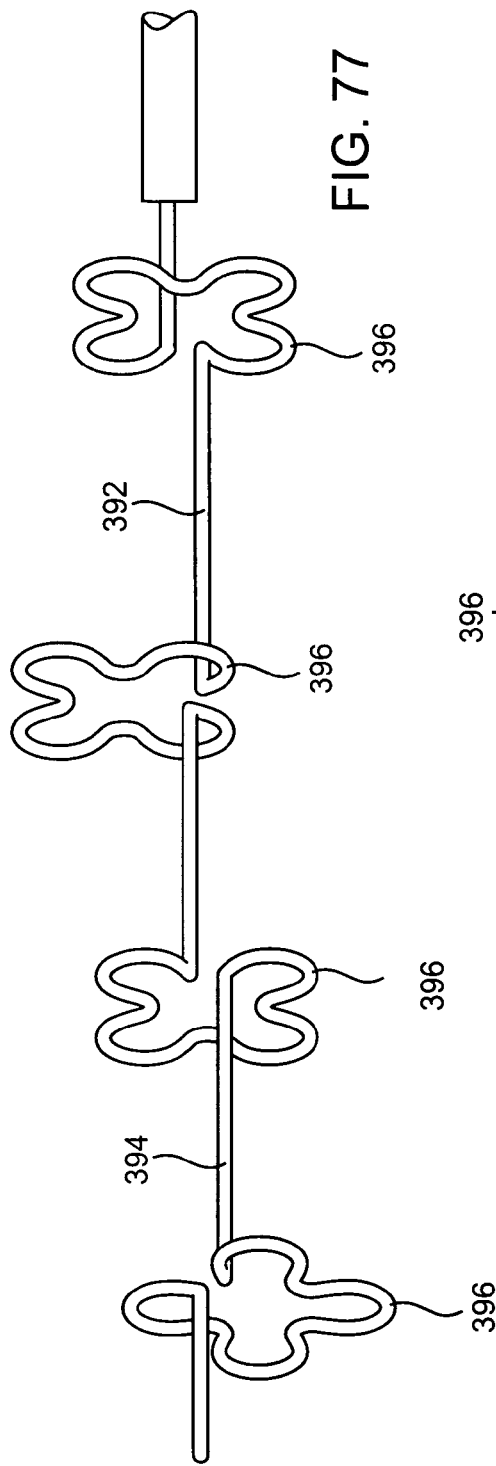

FIG. 77 shows another obstruction removing device.

Figure 78:
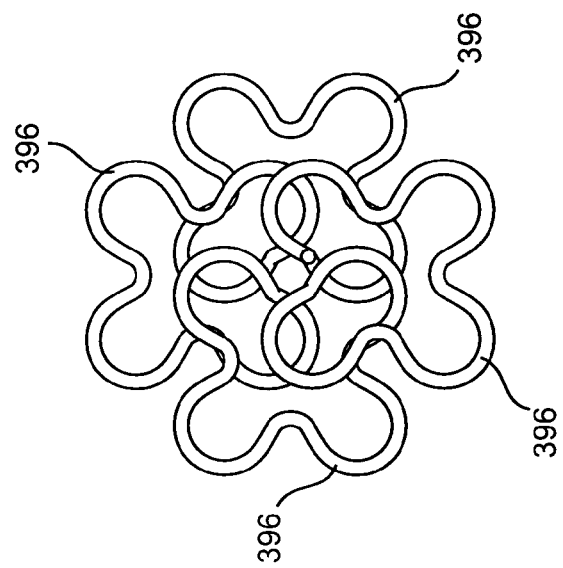

FIG. 78 is an end view of the obstruction removing device.

Figure 79:
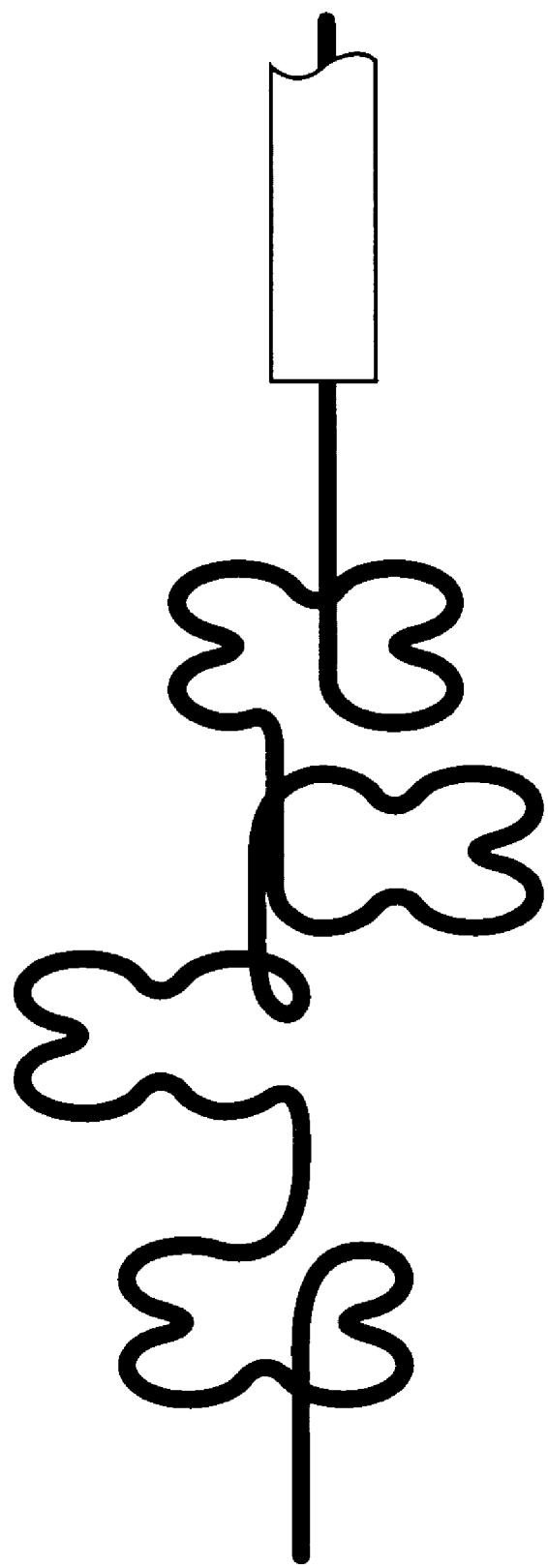

FIG. 79 shows another obstruction removing device.

FIG. 80 shows still another obstruction removing device having a loop.

FIG. 81 shows the device of FIG. 80 in a collapsed position.

Figure 82:
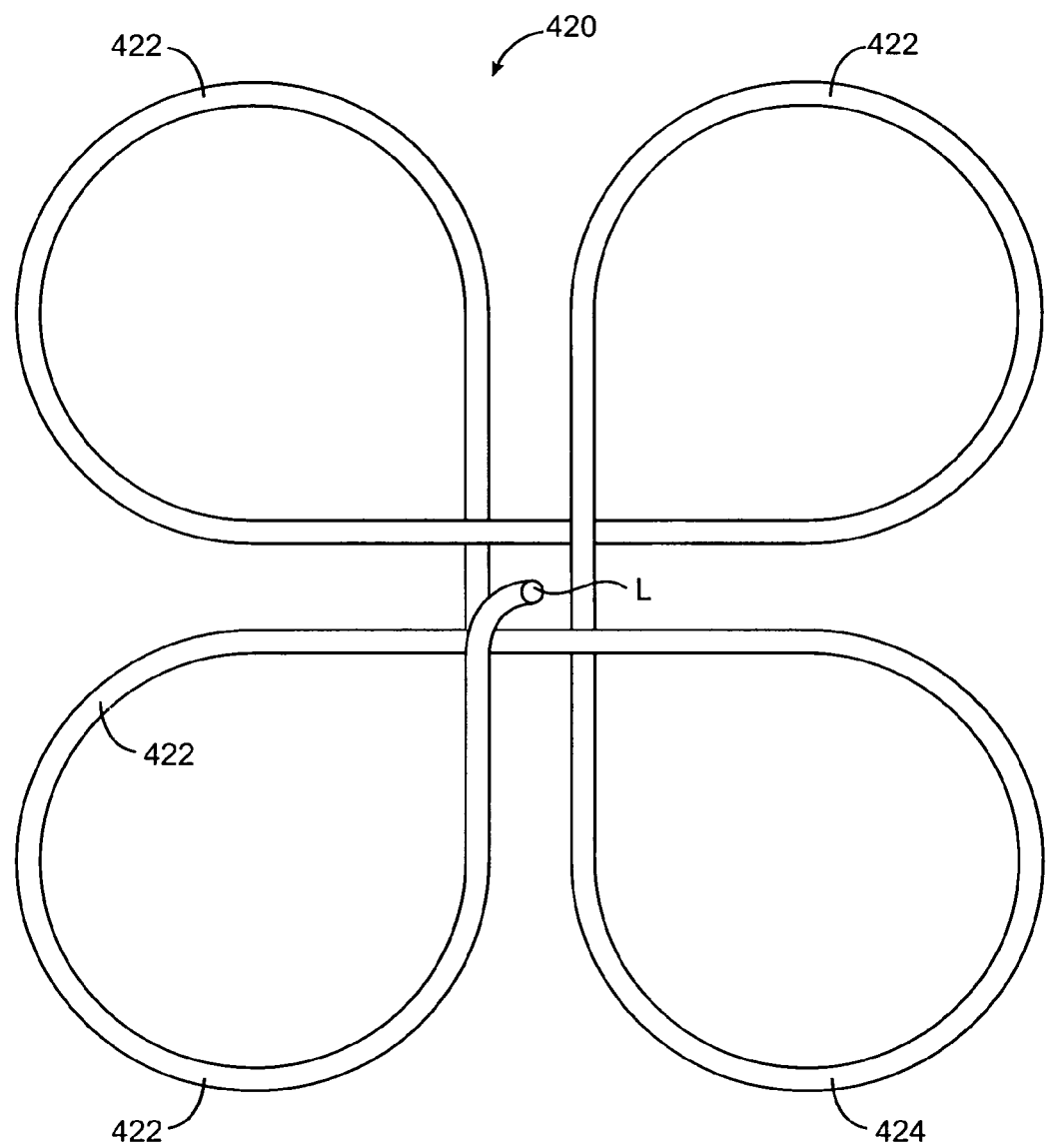
Figure 83:
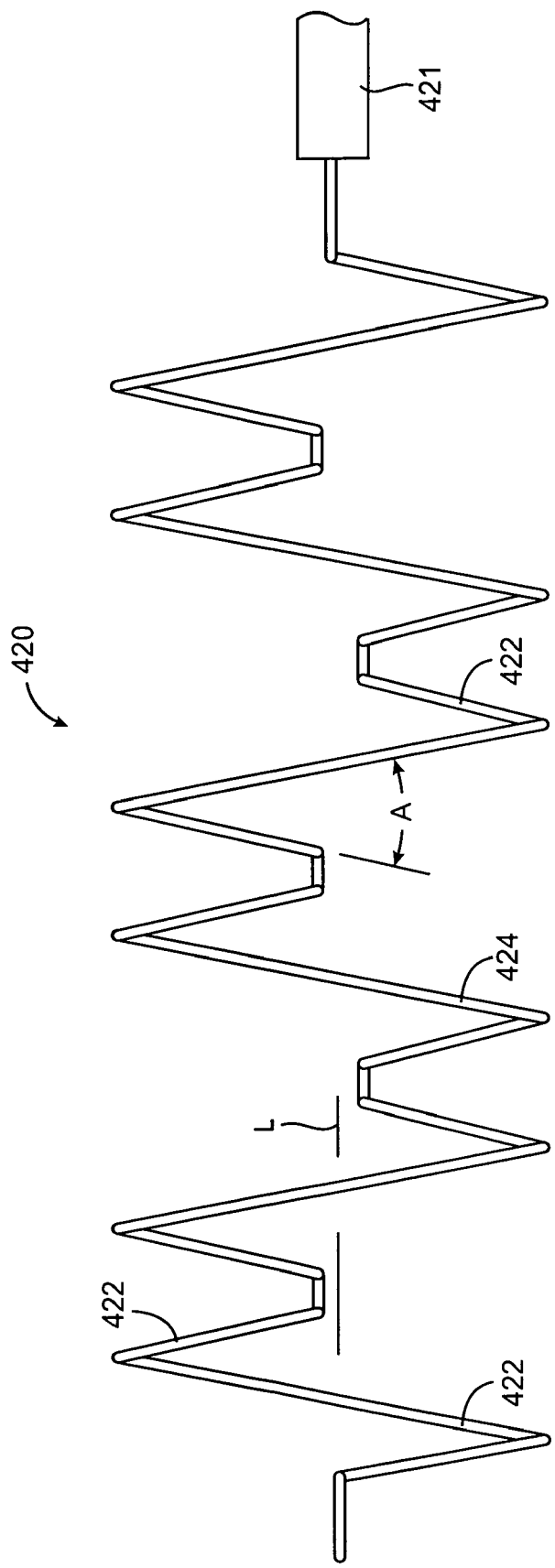

FIG. 82 shows a cross-sectional view of FIG. 83 along line III-III.

FIG. 83 shows a side view of another obstruction removing element.

DETAILED DESCRIPTION OF PREFERRED EMBODIMENTS

Referring now to FIGS. 1-4, a system 2 for removing an obstruction is shown. A guide catheter 4 is advanced to a location proximal to an obstruction. When accessing the cerebral vasculature, for example, the guide catheter 4 is often positioned in the carotid or vertebral artery. Of course, the guide catheter 4 may not be necessary or may be positioned in any other suitable location depending upon the location of the obstruction. The guide catheter 4 preferably has a flow restricting element 6 which restricts or even stops blood flow through the vessel as described below. The flow restricting element 6 is preferably a balloon 5 coupled to a source of inflation fluid 7 which is used to inflate the balloon 5.

An obstruction removing device 8 is advanced through the guide catheter 4 to the obstruction. A microcatheter 10 may also be positioned within the guide catheter 4 to deliver the obstruction removing device 8 further into the vasculature.

The obstruction removing device may be advanced by itself through the microcatheter 10 or may be contained within a sheath 12 which is advanced through the microcatheter 10. A source power 14 may also be coupled to the obstruction removal device 8 for use in the manner explained below. The power source 14 may simply produce a positive or negative charge or may be an RF or other suitable power source.

Figure 3:
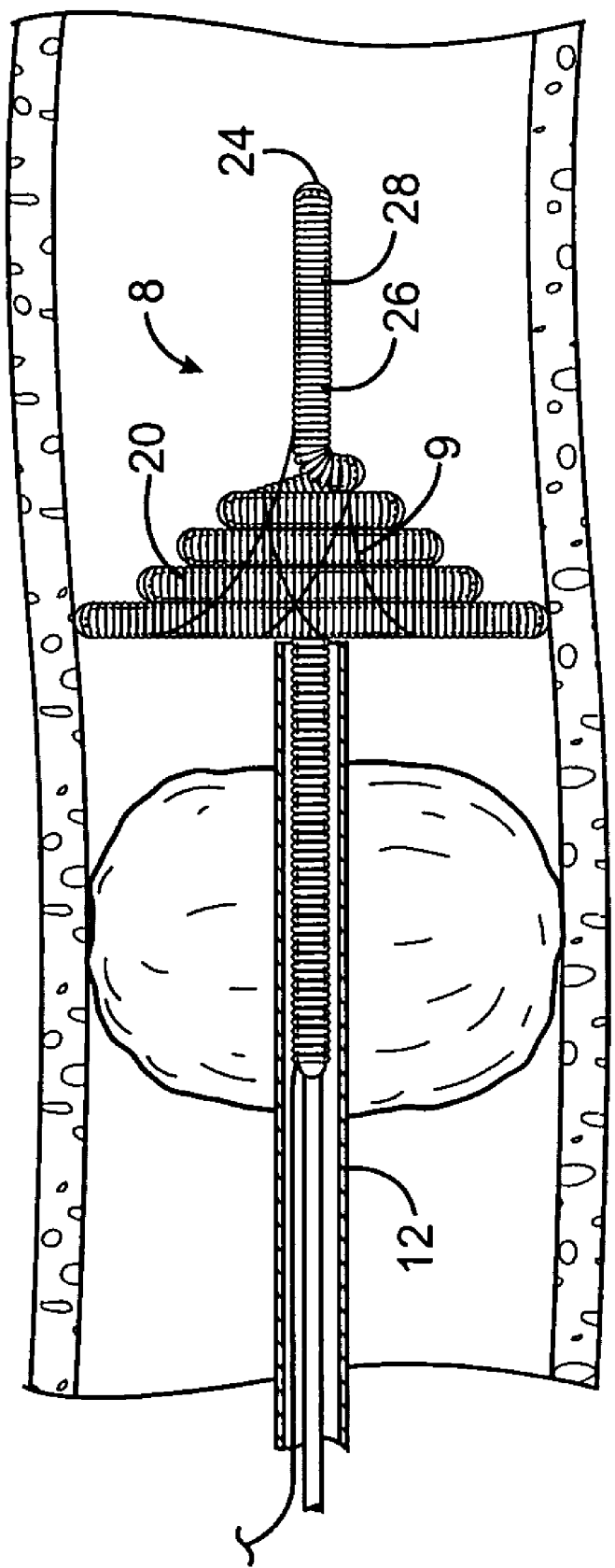
Figure 4:
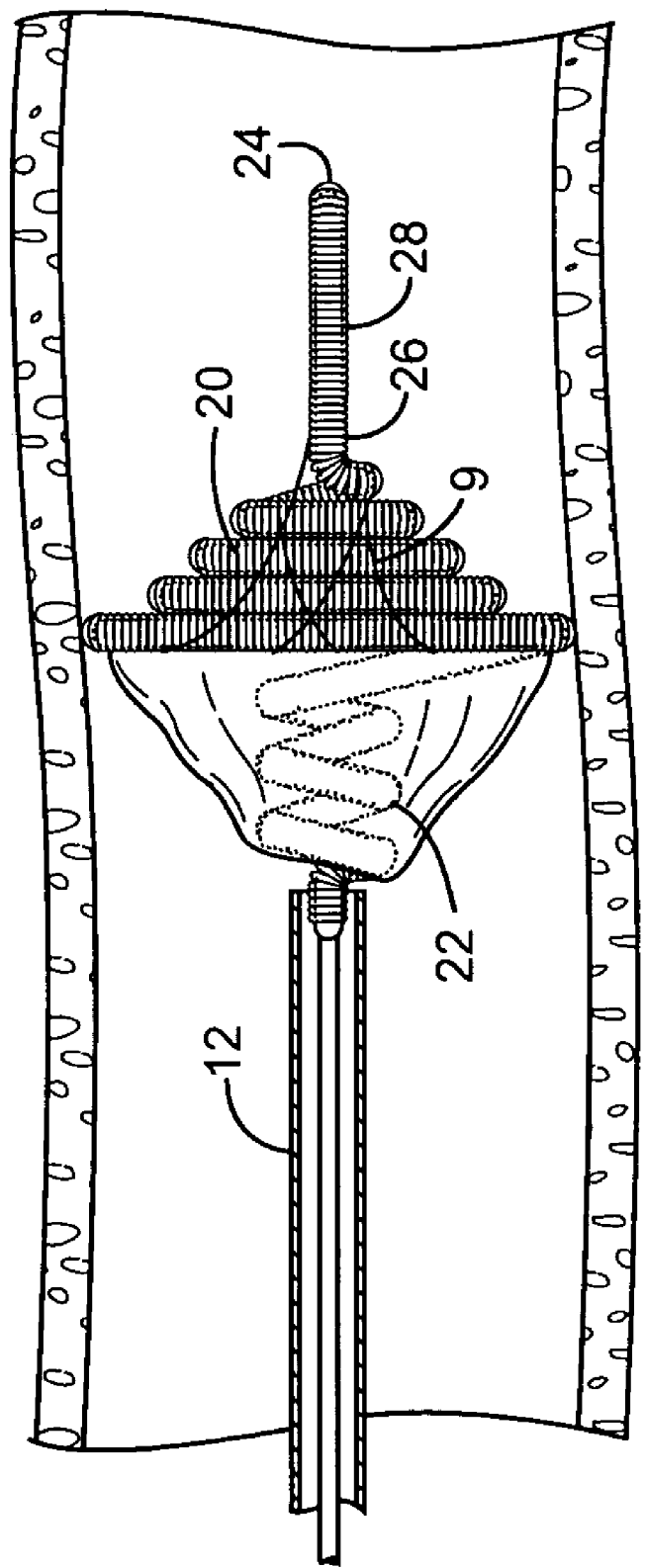

The obstruction removing device 8 has an engaging element 16 extending from an insertion element 18. The engaging element 16 is movable from a collapsed position (FIG. 2) to an expanded position (FIGS. 3 and 4). When the engaging element 16 is contained within the sheath 12 or microcatheter 10, the engaging element 16 is in a relatively straight configuration. The engaging element 16 has a distal portion 20, which forms a relatively closed structure, which can catch or trap the obstruction, or any part thereof, to prevent migration of the obstruction or part thereof. The engaging element 16 has a proximal portion 22 which is formed with smaller coils than the distal portion 20. The proximal portion 22 engages the obstruction as described below.

The engaging element 16 preferably has a number of markers 23, 25, 27 which provide an indication as to how much of the engaging element 16 extends from the sheath 12 or microcatheter 10. For example, markers 23, 25, 27 may indicate when the engaging element 16 is ½, ¾ or fully exposed. In this manner, the user may quickly advance the engaging element engaging element 16 through the sheath 12 or microcatheter 10 without inadvertently exposing and advancing the engaging element 16 out of the sheath 12 or microcatheter. The markers 23, 25, 27 can also be used to provide a controlled diameter of the engaging element 16 since the diameter of the engaging element 16 is known for the various positions corresponding to the markers 23, 25, 27. The markers 23, 25, 27 may also be used to size the vessel in which the engaging element 16 is positioned by observing when the engaging element 16 engages the vessel walls and determining the size of the engaging element 16 using the markers 23, 25, 27.

The insertion element 18 is preferably made of a superelastic material or stainless steel having a diameter of 0.004 to 0.038 inch and preferably about 0.010 inch. Although the insertion element 18 is preferably a solid, elongate element, the insertion element 18 may take any other suitable structure such as a hollow tube. The engaging element 16 is preferably made of a superelastic material, such as nitinol, and has a diameter of 0.005-0.018 inch, more preferably 0.005-0.010 inch and most preferably about 0.008 inch. The engaging element 16 has a rounded, atraumatic tip 24 to prevent damage to the vessel and facilitate advancement through the vessel, microcatheter 10 and/or sheath 12. A radiopaque wire 26, such as platinum ribbon 28 having a width of 0.004 inch and a thickness of 0.002 inch, is preferably wrapped around the engaging element 16 to improve radiopacity.

The device 8 is preferably self-expanding but may also be expanded with an actuator 29. The actuator 29 is preferably a thin filament which is tensioned to move the device 8 to the expanded position. An advantage of the invention is that the filament 29 extends through the same lumen as the device 8 thereby minimizing the overall size of the device. It is understood that throughout discussion of the devices and methods herein that any of the devices may be expanded using the actuator 29 rather than being self-expanding without departing from the scope of various aspects of the invention.

The device 8 may also include a cover 9 which extends between adjacent coils. The cover 9 may be a number of individual strands 11 which extend between the coils or may be an elastic membrane which covers the coils. The strands 11 are preferably elastic to stretch when the device 8 is expanded.

Use of the obstruction removing device 8 is now described. The guide catheter 4 is introduced into the patient and delivered proximal to the target vessel such as to the carotid or vertebral artery. The microcatheter 10 is then advanced through the guide catheter 4 further into the vasculature to a position proximal to, within or distal to the obstruction. The obstruction removal device 8 is then advanced through the microcatheter 10 either by itself or pre-loaded within the sheath 12. The obstruction removal device 8 is then advanced to the obstruction. Before advancing the obstruction removal device 8 further, the flow restricting element 6 on the guide catheter 4 is expanded to reduce and even stop flow through the vessel. Stopping flow in the vessel may help prevent the obstruction, or any parts thereof, from migrating downstream. Reducing flow through the vessel may also reduce the likelihood that the obstruction is disrupted by a combination of flow and the obstruction removal device 8.

The obstruction removal device 8 is then placed into the obstruction and preferably through the obstruction. The engaging element 16 is then advanced out of the microcatheter 10 or sheath 12 to permit the distal portion 20 of the engaging element 16 to expand at a location beyond the obstruction. In this manner, the relatively closed distal portion 20 prevents the obstruction, or any part thereof, from migrating downstream. The proximal portion 22 is then advanced out of the sheath 12 or microcatheter 10 so that the smaller coils of the proximal portion 22 engage the obstruction as shown in FIG. 4.

Figure 5:
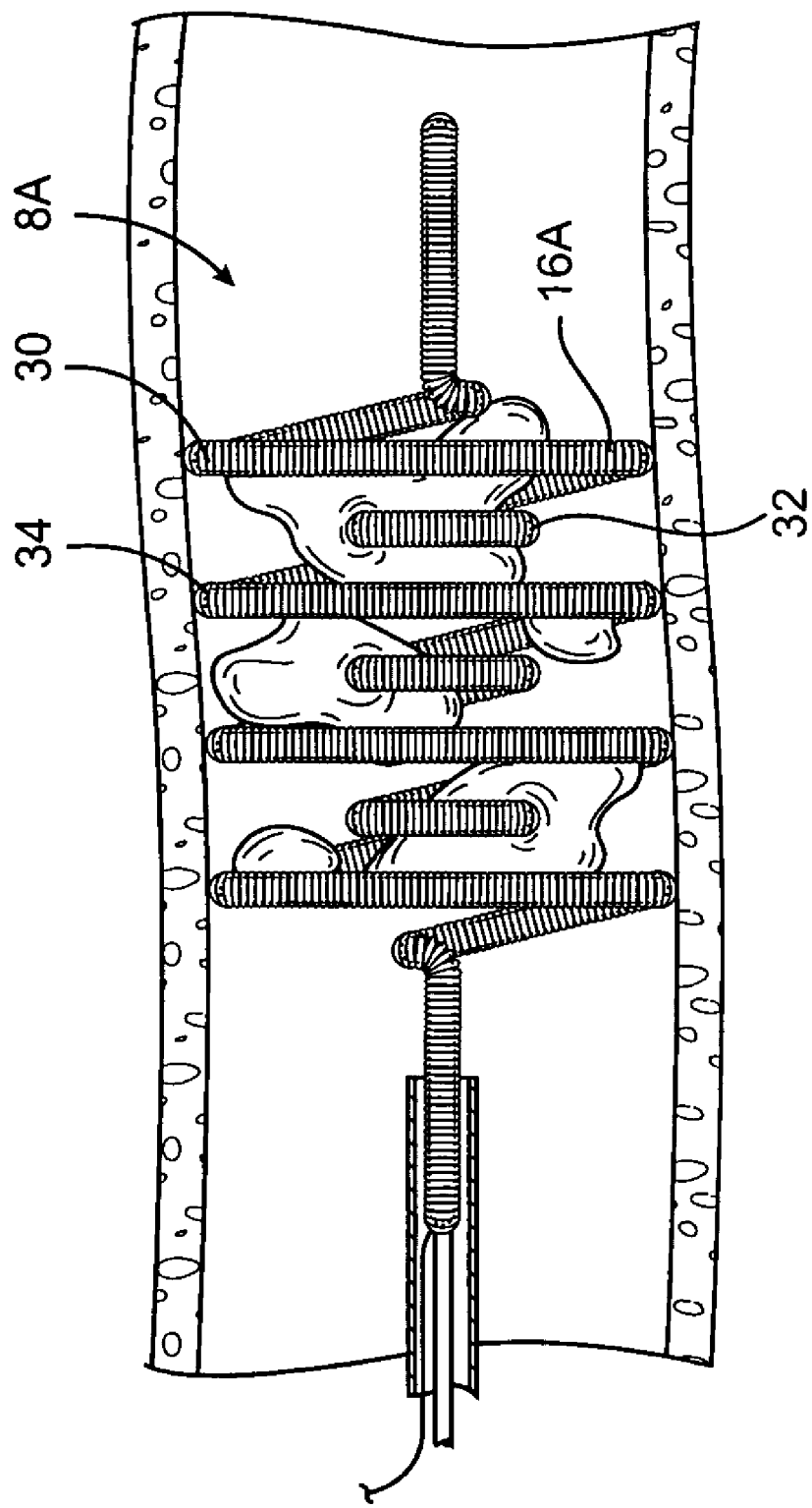

Referring to FIG. 5, another obstruction removal device 8A is shown wherein the same or similar reference numbers refer to the same or similar structure. The obstruction removal device 8A has a first section 30 with larger diameter coils than a second section 32. A third section 34 also has larger coils than the second section 32 with the second section 32 positioned between the first and third sections 30, 34. The obstruction removal device 8A may have a number of alternating small and large sections 30, 32, 34 which can enhance the ability of the obstruction removal device 8A to engage various obstructions. In the preferred embodiment of FIG. 5, the obstruction removal device 8A has four large sections 32, 34 with relatively large coils and three sections 30 having smaller coils.

The obstruction removal device 8A may be used in any suitable manner to engage the obstruction. For example, the microcatheter 10 or sheath 12 may be advanced through the obstruction and then retracted to expose the obstruction removal device 8A. The obstruction removal device 8A is then retracted into the obstruction to engage the obstruction. The obstruction removal device 8A may be rotated when moved into the obstruction to take advantage of the generally helical shape of the obstruction removal device. The obstruction removal device 8A may also be used to engage the obstruction by simply retracting the microcatheter 10 or sheath 12 with the obstruction removal device 8A expanding within the obstruction. Finally, the engaging element 16A may be exposed and expanded proximal to the obstruction and then advanced into the obstruction. When advancing the obstruction removal device 8A into the obstruction, the user may also twist the obstruction removal device 8A to take advantage of the generally helical shape. The alternating large and small sections 30, 32, 34 enhance the ability of the engaging element 16A to engage varying shapes and sizes of obstructions.

Figure 6:
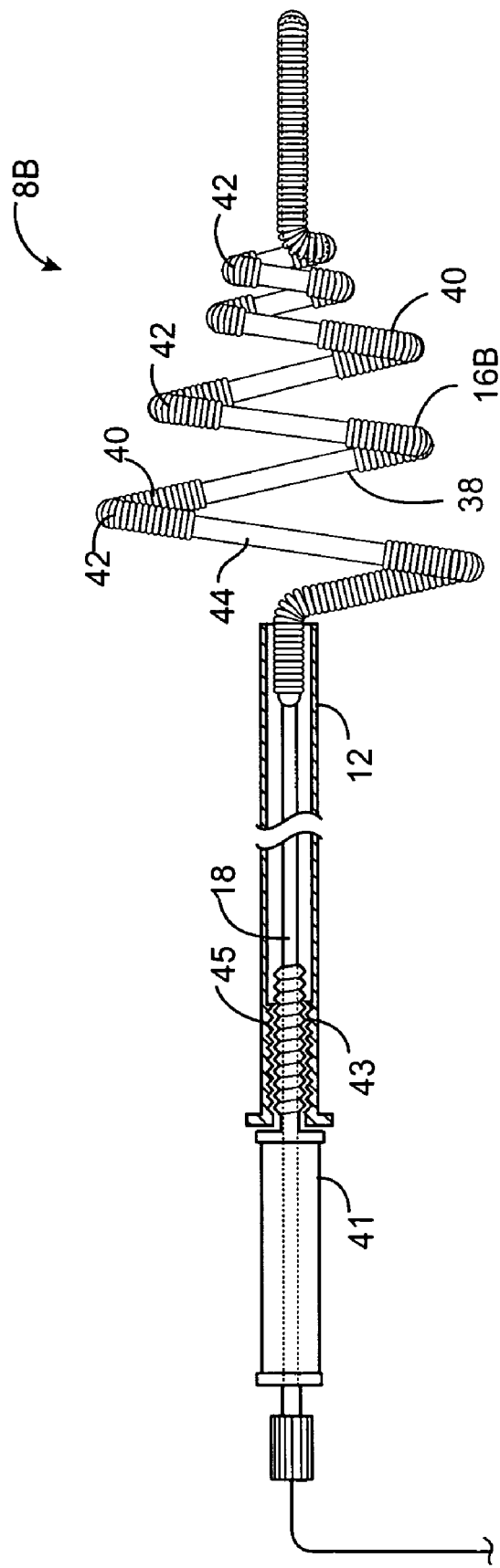

Referring to FIG. 6, still another obstruction removal device 8B is shown wherein the same or similar reference numbers refer to the same or similar structure. The obstruction removal device 8B has the insertion element 18 with an engaging element 16B extending therefrom. The engaging element 16B forms a helical coil 38 with a generally frustoconical shape, however, the engaging element 16B may take any other shape without departing from the scope of the invention including any shape disclosed in this application or any patent incorporated by reference herein.

A filament 40, preferably a radiopaque filament, is wrapped around the engaging element 16B. The filament 40 is wrapped somewhat loosely around the engaging element 16B so that the filament 40 provides additional surface area to engage the obstruction. The filament 40 forms a wound section 42, and more preferably at least five wound sections 42, which are separated by substantially exposed sections 44 of the engaging element 16B. The wound and exposed sections 42, 44 may be 1-5 mm long. Stated another way, the wound and exposed sections 42, 44 are at least 1 mm, more preferably at least 3 mm long, and no more than 8 mm long. The wound sections 42 may be formed by a single filament 40 which extends continuously between the wound sections 42 or may be formed by independent filaments 40 at each wound section 42 which are attached to the engaging element 16B.

The wound sections 40 may be movable along the engaging element 16B to provide flexibility when advancing the obstruction removal device 8B through small and tortuous vessels. The movable wound sections 40 may also allow different parts of the obstruction removal device 8B to grip different parts of the obstruction to hold the obstruction together or engage different parts of the obstruction. The obstruction removal device 8B is used in substantially the same manner as the other obstruction removal devices described herein. The obstruction removal device 8B has a handle 41 with a lead screw 43 which engages threads 55. The handle 41 is rotated to advance and retract the engaging element 16B.

Figure 7:
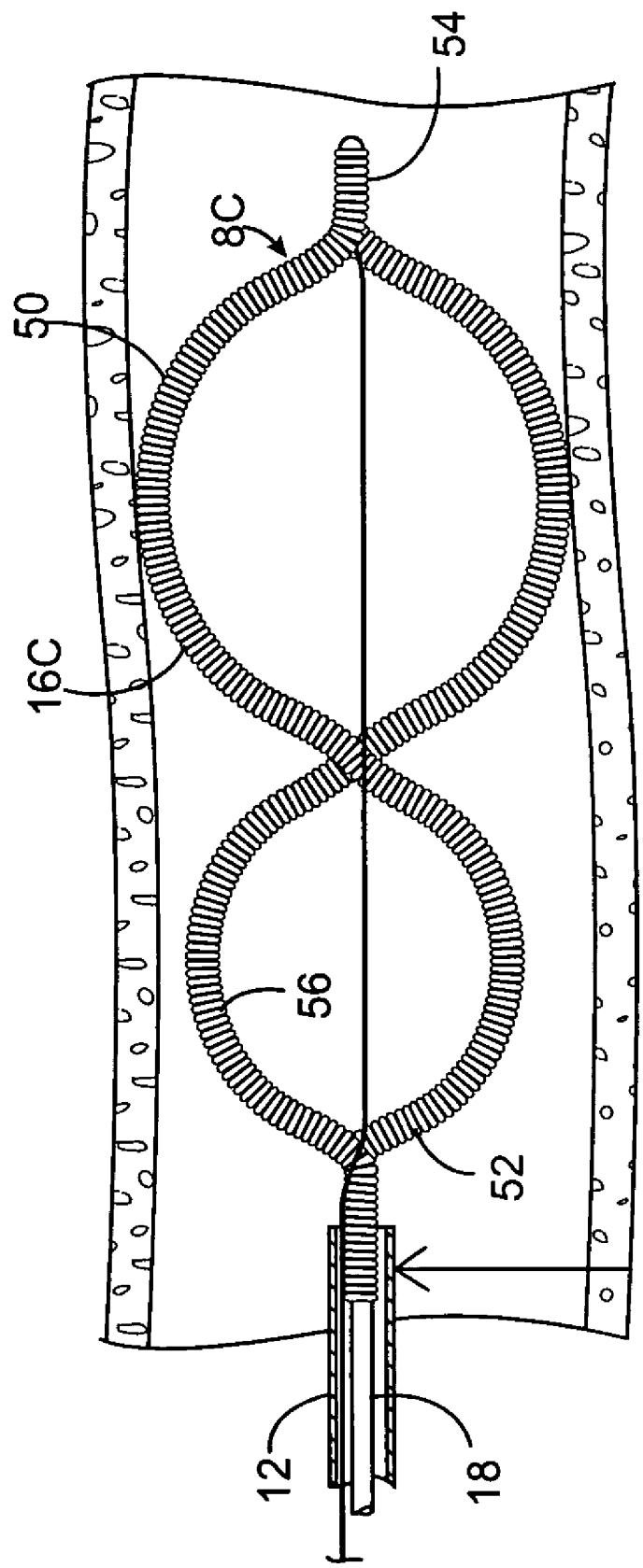

Referring to FIG. 7, still another obstruction removal device 8C is shown wherein the same or similar reference numbers refer to the same or similar structure. The obstruction removal device 8C has an engaging element 16C, which forms a first closed loop 50, and a second closed loop 52. The first loop 50 is preferably somewhat larger than the second closed loop 52 with the first loop 50 having a diameter of about 1.5-8.0 mm and the second loop 52 having a diameter of about 1.5-6.0 mm. A tip 54 extends from the first loop 50 for a distance of about 5 mm. A radiopaque element 56, such as platinum ribbon, is preferably wrapped around the loops 50, 52 to improve radiopacity and to enhance the ability of the engaging element 16C to hold the obstruction. The radiopaque element 56 also may provide advantages when engaging an obstruction in a manner similar to the obstruction removal devices described above with reference to FIG. 6.

Figure 8:
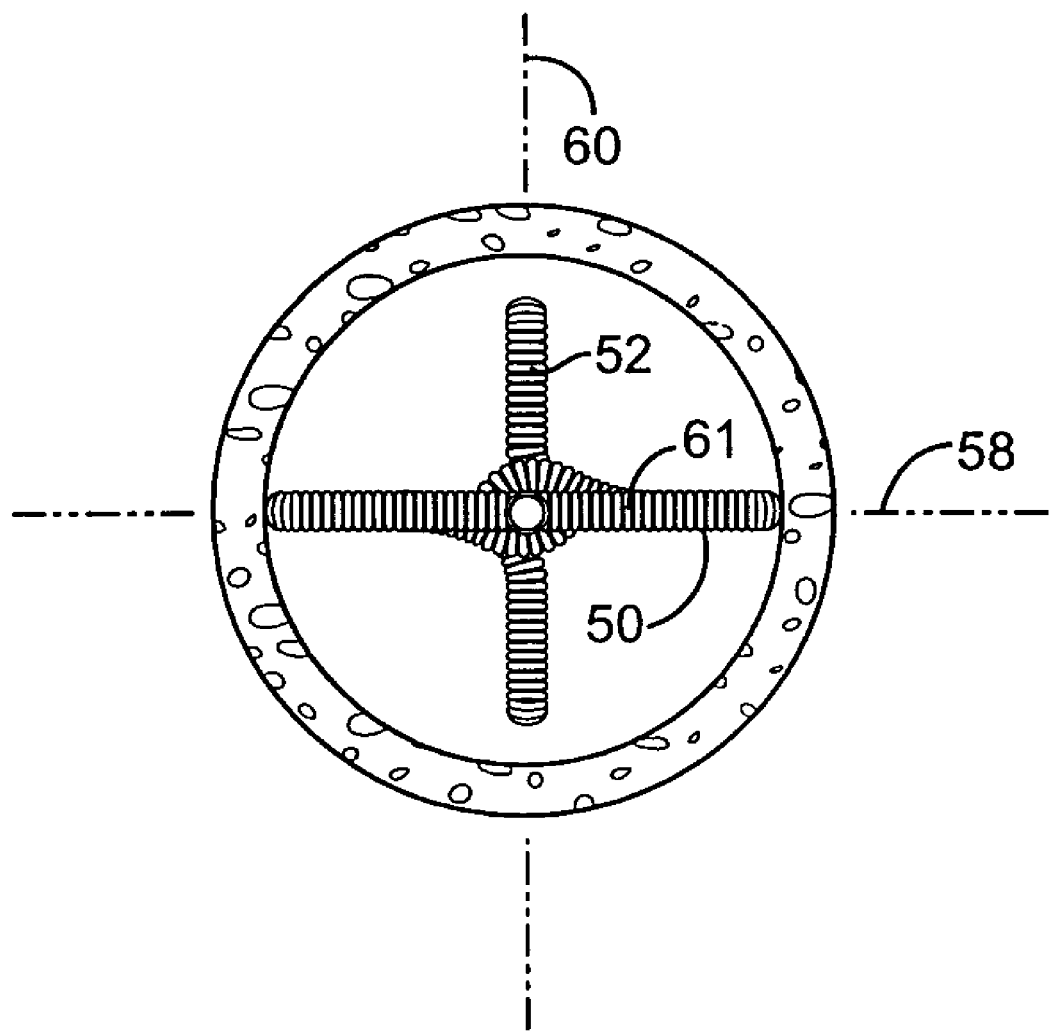

An advantage of the obstruction removal device 8C is that the loops 50, 52 exert substantially equal and opposing forces on the sheath 12 or microcatheter 10 through which the obstruction removal device 8C is advanced. In this manner, kinking or binding of the obstruction removal device 8C during advancement can be minimized or reduced altogether. Referring to the end view of FIG. 8, the first and second loops 50, 52 preferably lie in first and second planes 58, 60, respectively, which are preferably perpendicular to one another.

Another method of aiding mechanical capture of an obstruction is to coat the device and elements of the present invention with a material 61 which helps to adhere the obstruction, and in particular thrombus, to the device or element. The material 61 is preferably fibrin but may be any other suitable material. Use of the material 61 may be incorporated into any of the devices described herein or other suitable device such as the devices shown in FIG. 2-8, 22 or 30.

Figure 9:
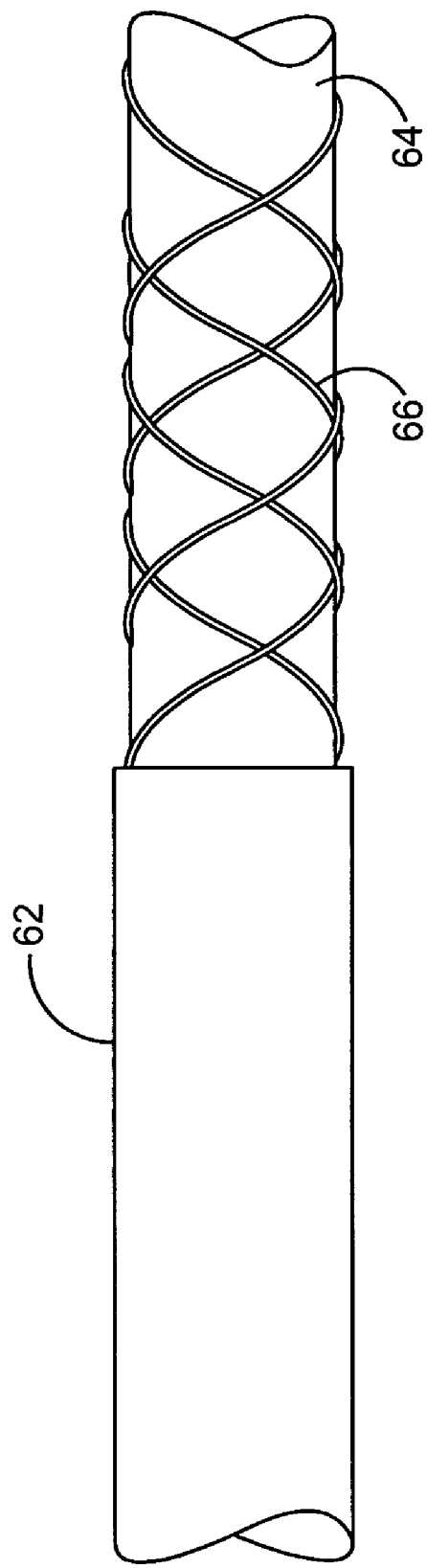

Referring to FIG. 9, an exploded view of a construction of the obstruction removal device 8, 8A, 8B, 8C is shown. A tube 62, which is preferably a thermoplastic polymer such as polyester or urethane is positioned over a core element 64. As mentioned above, the core element 64 is preferably a superelastic or stainless steel element at either the insertion element 18 or the engaging element 16 (FIGS. 2-7). A reinforcing strand 66 is trapped between the tube 62 and the core element 64 to reinforce the obstruction removal device. The strand 66 is preferably small and has a diameter or thickness of less than 0.005 inch, more preferably less than 0.0001 inch, so that the overall size of the obstruction removal device is not increased significantly with use of the strand 66. The strand 66 may be made of any suitable material including VECTRAN made by Celanese Acetate LLP or DACRON or KEVLAR which are both manufactured by Dupont. VECTRAN is a thermoplastic multifilament yarn spun from a liquid crystal polymer.

The strand 66 provides a degree of safety in that the strand 66 and tube 62 together prevent any part of the obstruction removal device from breaking free from the rest of the device. The tube 62 will resist breaking since it is more flexible than the core element 64 and can undergo larger deflections and displacements without breaking. In a preferred embodiment, 2-8 strands 66, preferably about 4 strands 66, are used. The overall size of the device is also relatively small with the outer diameter of the resulting structure being no more than 0.020 inch and more preferably no more than 0.012 inch.

The power source 14 may be also be used with any of the obstruction removal devices in the following manner, however, the methods and devices of the present invention may, of course, be practiced without the power source 14. As mentioned above, the power source 14 may simply produce a charge at the engaging element 16 or may be a source of RF energy. In one particular method of the present invention, the power source 14 produces a negative charge while advancing the engaging element 16 through the obstruction. The negative charge may aid in passing the engaging element 16 through the obstruction and may help to dissolve part of the obstruction. The power supply is then changed to produce a positive charge to adhere the obstruction to the engaging element 16. Alternatively, the power source 14 may be an RF energy source, which delivers RF to the engaging element 16 which also adheres the obstruction to the engaging element 16 and may help provide a controlled penetration into the obstruction. The obstruction is then removed by moving the obstruction into the guide catheter 4, which is then withdrawn to remove the obstruction. Use of the power source 14 is particularly useful when the obstruction is a biologic structure such as a clot.

Referring to FIGS. 10-14, another system 100 for removing an obstruction is shown. The system 100 is particularly useful for removing clots and thrombus from blood vessels but may also be used to remove other obstructions such as embolic coils and the like. The system 100 includes an expandable capture element 102 and an obstruction engaging device 106 which work together to capture the obstruction. The obstruction engaging device 106 engages the obstruction and moves the obstruction into the capture element 102 as described below. After the obstruction has been captured, the capture element 102 may then be used in various ways for ultimate removal of the obstruction. The capture element 102 may be advanced through the guide catheter 4 or through another catheter 107 which is advanced through the guide catheter 4. As will be explained below, the capture element 102 is preferably advanced over the obstruction engaging device 106.

The obstruction engaging device 106 may be any of the engaging or removal devices described herein or any other suitable device. Various aspects of the invention preferably include one or more features of the obstruction removing devices described herein and all aspects, features, dimensions, and characteristics of the obstruction removing and engaging devices described herein are incorporated here. It is understood that the term obstruction removal device and obstruction engaging device are interchangeable. The obstruction engaging device 106 may be contained within the sheath 12 or may be advanced by itself through the guide catheter 4 and/or catheter 107.

The engaging device 106 may have one or more filaments 108, preferably 1-4 and more preferably 1-2 filaments, which engage the obstruction. The filament 108 forms a relatively small, flexible interaction between the engaging device 106, capture element 102 and obstruction which provides advantages over the prior art method of using a balloon catheter. The filament 108 may deflect and displace to accommodate the geometry and orientation of the obstruction when the obstruction enters the capture element 102. The interaction between the balloon catheter and the expandable catheter of the prior art tends to shear off portions of the obstruction due to the relatively rigid interaction between the balloon catheter and expanded catheter. The filament 108 also has a relatively small size which further enhances the flexibility of the obstruction engaging device 108. The filament 108 may also form one or more loops 110 which further serve to create a soft, flexible interaction between the obstruction engaging device 106 and capture element 102. The filaments 108 may also form a filter which further prevents the obstruction or portions thereof from travelling downstream.

The capture element 102 preferably has a support structure 112 with a flexible cover 114 attached thereto. The support structure 112 is preferably self-expanding although the support structure 112 may also be selectively expanded by the user as explained below. The support structure 112 preferably has a loop 116 having integrally formed hinges 117. The hinges 117 are preferably formed by V-shaped interconnecting elements 120 although other shapes, such as U-shaped, may be used. The loop 116 is preferably formed as an integral structure with the loop 116 being formed from a tube of material which is cut, etched, treated or otherwise formed into the loop 116 with hinges 117. The loop is preferably made of a superelastic material although any suitable material may be used.

Figure 14:
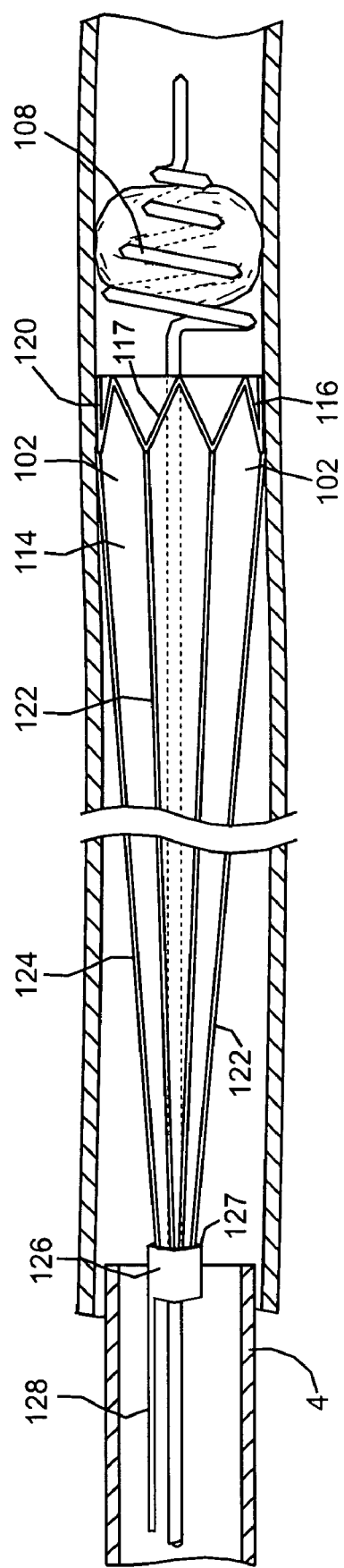
Figure 15:
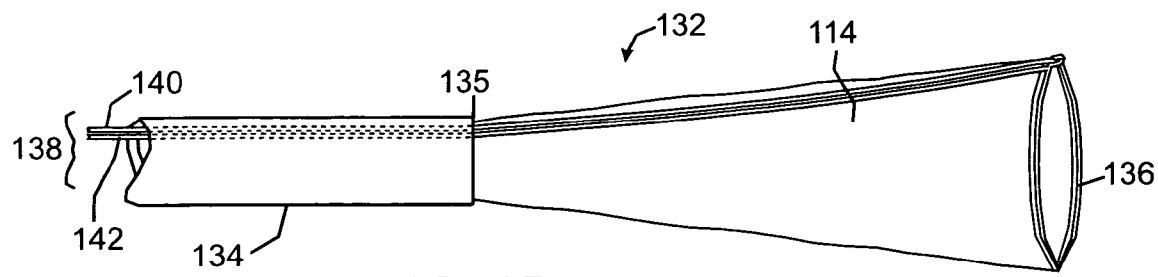
Figure 16:
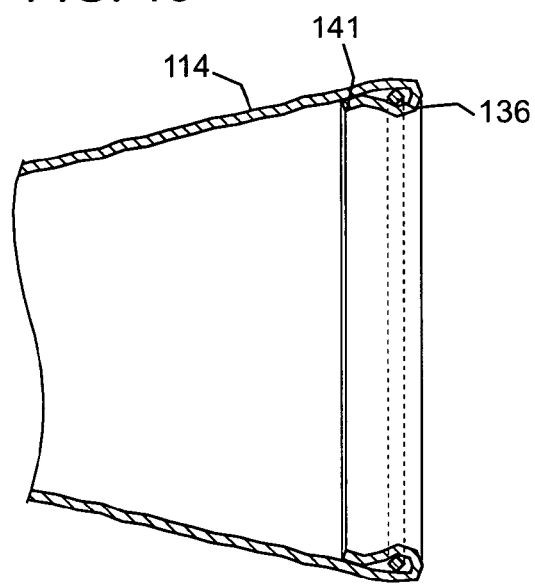
Figure 17:
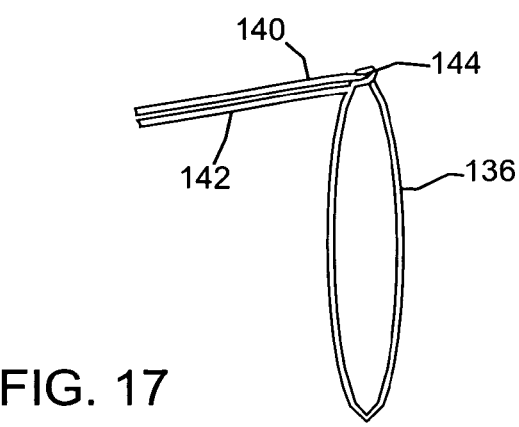

Struts 122 extend proximally from the loop 116. The struts 122 do not intersect and generally form a cone 124 when expanded. The struts 122 are coupled to a lumen 121 which receives the engaging device 106 so that the capture element 102 can be advanced over the engaging device 106 as described below. Referring also to FIG. 14, the struts 122 may also be coupled together at a hub 126 at the proximal end. The hub 126 has a lumen 127 which receives the engaging device 106. A shaft 128 extends from the hub 126 and is used to manipulate the capture element 102. The struts 122 are preferably made of a superelastic material or stainless steel and are attached to the closed loop 116 by soldering, welding, glue or any other suitable attachment method. The struts 122 may also be integrally formed with the loop 116. Of course, the supporting structure 112 may be made of any other suitable material and may be formed in any other suitable manner. The struts 122 may also be bowed outward so that the distal end of the device is preferentially closed before the entire device has been withdrawn as shown in FIGS. 23 and 24.

The cover 114 is preferably attached to the support structure 112 with glue, thread, suture or any other suitable method. The cover 114 preferably lies over the support structure 112 but may also be contained within the support structure 112. The cover 114 is relatively long to ensure that the entire obstruction is captured. The cover 114 is preferably at least three times, more preferably at least five times, and most preferably at least seven times larger than the maximum expanded diameter of the support structure 112 or cover 114. Of course, the capture element 102 may have any other suitable dimensions depending upon the particular application. The cover 114 is preferably made of ePTFE but may be made of any other suitable material. The cover 114 may also be a mesh-like structure, or any other suitable expandable structure which can contain the obstruction and parts thereof, without departing from the scope of the invention.

Various methods of the present invention are now described. The methods are described in connection with system 100 of FIGS. 10-14 but may be practiced with other suitable devices and systems. The present invention is well-suited for use in the cerebral vasculature and a cerebral application is described, however, the invention may be practiced in other vascular locations as well.

The guide catheter 4 is advanced to a suitable location. The obstruction engaging device 106 is then advanced through the guide catheter 4. Referring to FIGS. 11 and 12, the obstruction engaging device 106 is then used to engage the obstruction in any manner described herein. For example, the sheath 10 (see FIG. 10) may be advanced through the obstruction and then retracted so that a proximal portion 111 of the device 106 is contained within the obstruction. The device 106 is then moved proximally, and is preferably twisted, so that the loops 110 engage the obstruction. In the specific embodiment of FIGS. 11-14, the device 106 ensnares the obstruction with the loops 110 when twisted and moved proximally.

Figure 13:
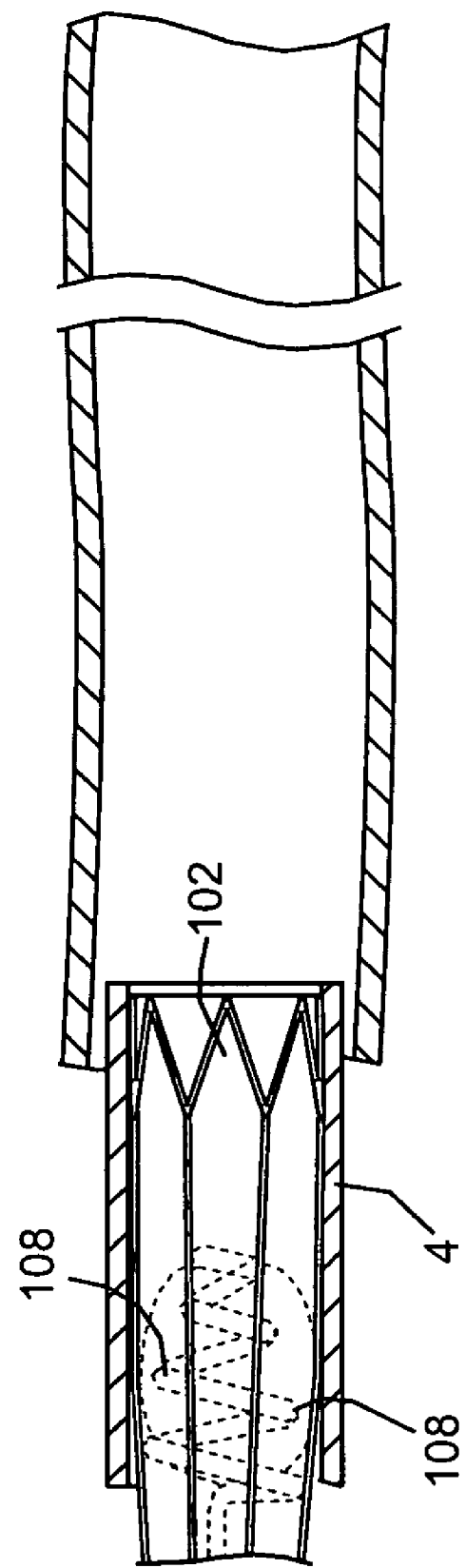

The capture element 102 is then advanced over the engaging device 106. The capture element 102 may be advanced through the guide catheter 4 or may be advanced through the catheter 107 which is advanced through the guide catheter 4 further into the cerebral vasculature. The capture element 102 is then moved out the catheter 107 or guide catheter 4 so that the capture element 102 expands. The obstruction is then moved into the capture element 102 with the device 106 as shown in FIG. 13. When the obstruction is contained within the capture element 102, the capture element 102 is then withdrawn into the catheter 107 or guide catheter 4 as shown in FIG. 14. The catheter 107 and/or guide catheter 4 are then withdrawn from the patient thereby withdrawing the obstruction.

It may be desirable to reduce or even stop blood flow through the blood vessel during the procedure to reduce flow forces on the obstruction when manipulating the obstruction. Reducing flow in the vessel may also prevent some parts of the obstruction from breaking off and flowing downstream before entering the capture element 102. Referring again to FIGS. 10 and 22, blood flow may be reduced by inflating a balloon 131 on the guide catheter 4 or the catheter 107. The balloon 131 is inflated using a suitable source of inflation fluid 133. Alternatively, the capture element 102 itself may also be used to reduce blood flow through the vessel. The capture element 102 naturally impedes blood flow since it expands within the blood vessel. The capture element 102 may also be designed to only partially occlude the vessel so that some blood flow is provided to the area downstream from the capture element 102. The device 102 may be modified to include a second loop 130 extending between the struts 122 to enhance the ability of the device 102 to occlude the vessel. The loop 130 preferably has the features of the loop 116. Although it is preferred to reduce or even stop flow in the vessel, the invention may also be practiced without reducing blood flow.

The devices and methods of the present invention may also be practiced with a source of vacuum 135 providing suction during capture of the obstruction. The source of vacuum 135 may be activated during engagement of the obstruction with the device 106, movement of the obstruction into the capture element 102, and/or withdrawal of the capture element 102 into the catheter 107 or guide catheter 4. The source of vacuum 135 is coupled to the guide catheter, 4, catheter 107 and lumen 121 for these purposes.

Referring to FIGS. 10 and 15-17, another capture element 132 for removing an obstruction is shown wherein the same or similar reference numbers refer to the same or similar structure. The capture element 132 is selectively expandable by the user which provides various advantages described below. The cover 114 is attached to a catheter 134 near or at the distal end 135. The catheter 134 may be the guide catheter 4 or the catheter 107 in the system 100 described above. An expandable and collapsible loop 136 is attached to the distal end of the cover 114 to expand and collapse the distal end of the cover 114. The loop 136 is expanded and collapsed by manipulating an actuator 138 which includes a control arm 140 and a stable arm 142. The control arm 140 extends and slides through an eyelet 144 when expanding and collapsing the loop 136. The stable arm 142 extends from the loop 136 at or near the eyelet 144 to stabilize the loop 136 when moving the control arm 140. The cover 114 is attached to the loop 136 using any suitable method. For example, the distal end may be inverted to create a fold 141 which surrounds the loop 136.

Figure 18:
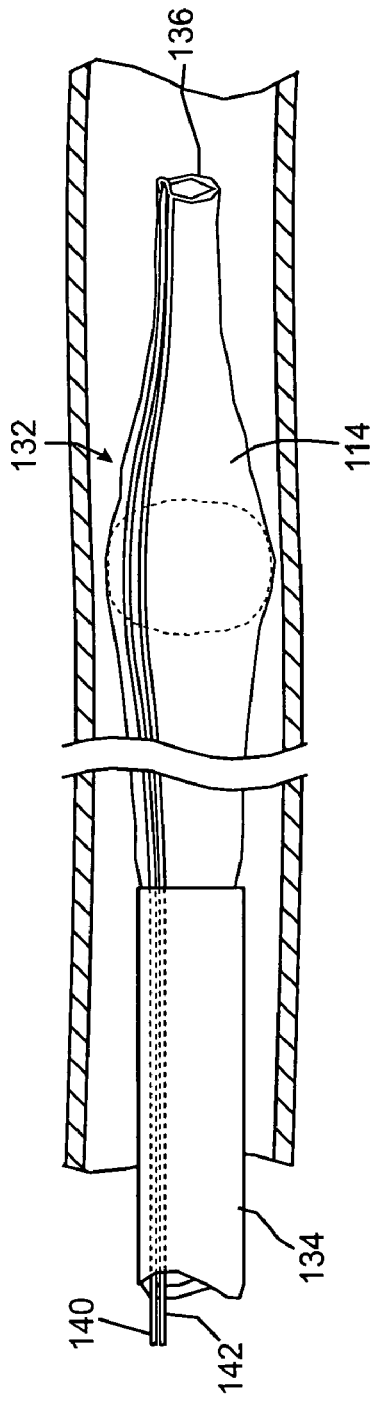

Another advantage of the capture element 132 is that the capture element 132 may be selectively expanded and contracted by the user. The capture element 132 may be fully or partially collapsed to trap the obstruction prior to withdrawal of the capture element 132 into the catheter 107 or guide catheter 4 as shown in FIG. 18. In fact, the capture element 132 may be withdrawn by itself by simply closing the distal end and withdrawing the capture element 132. In this manner, the capture element 132 protects the obstruction during withdrawal and prevents the obstruction from escaping. This provides obvious advantages over the system of Guenther described above.

Figure 10:
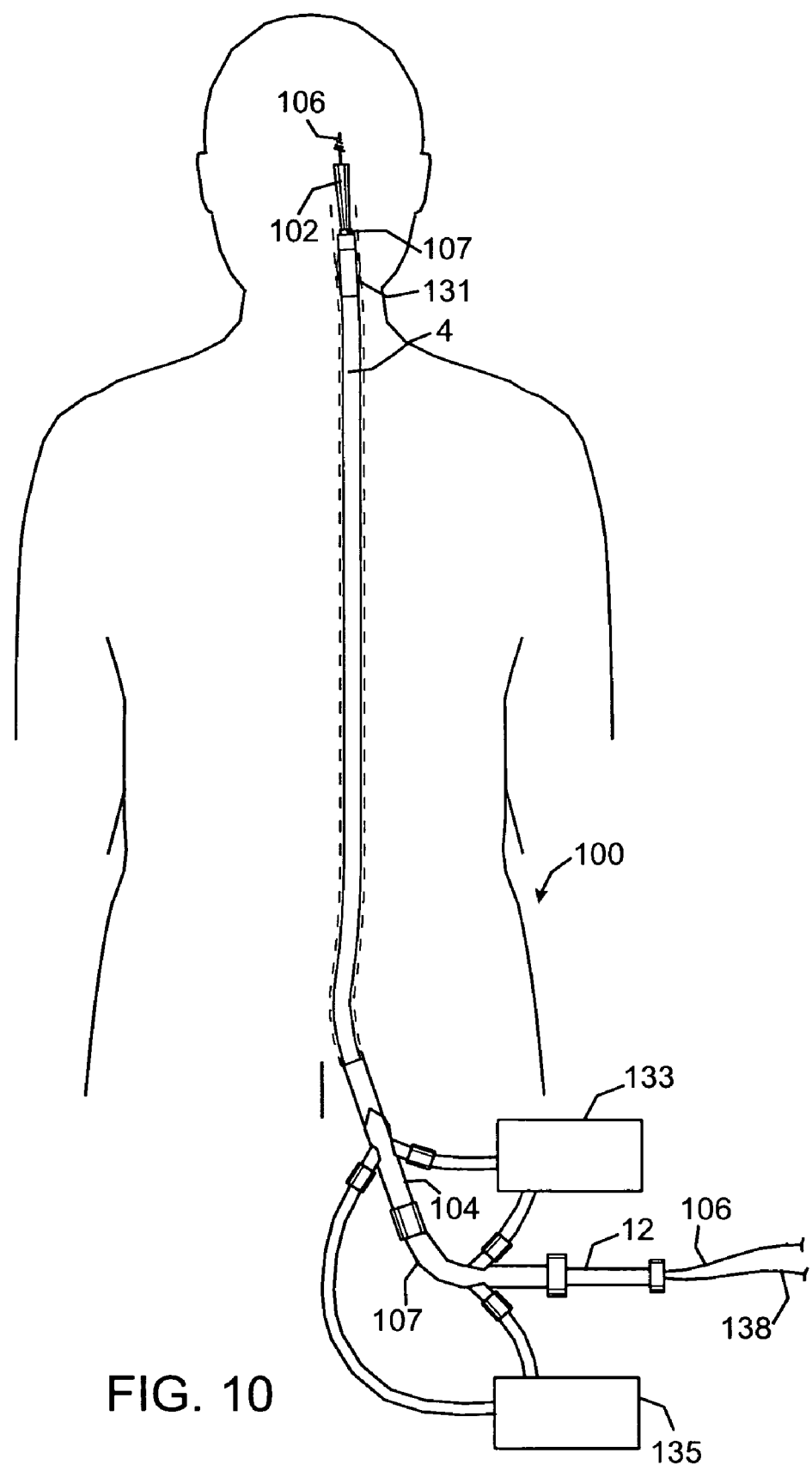
Figure 19:
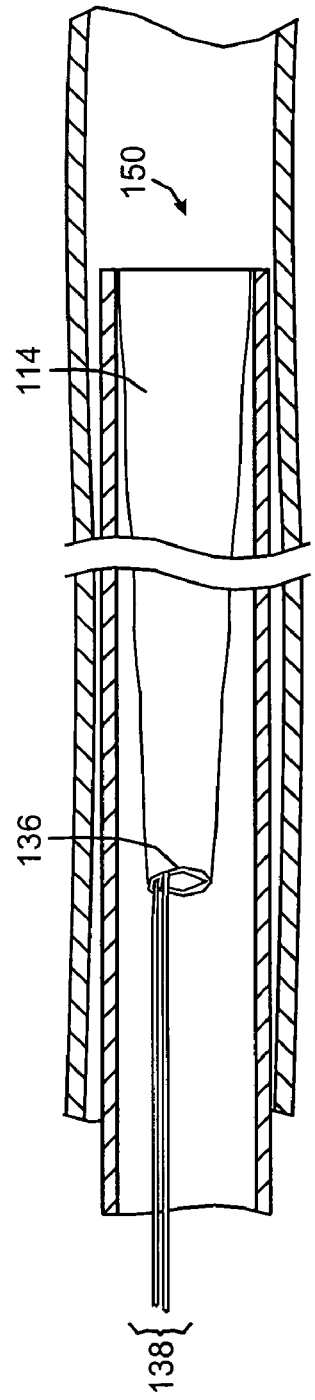

Referring to FIGS. 10 and 19, still another capture element 150 is shown in which the same or similar reference numbers refer to the same or similar structure. The capture element 150 has the cover 114 and the actuator 138 which includes the stable arm 142, control arm 140, and loop 136 although other actuating structures may be used. The capture element 150 is contained within the catheter 107 or the guide catheter 4 during introduction and is then everted out of the catheter 107 or catheter 4 when deployed. The capture element 150 may be used in substantially the same manner as the other capture elements described herein and in particular the capture element 132 of FIGS. 15-17. The capture element 150 may also be used to further collapse the cover 114 since the actuator 138 may be used to close the distal end with the cover 114 deployed. After the obstruction is contained within the capture element 150, the capture element 150 is withdrawn into the catheter 107 or catheter 4. Although it is preferred to withdraw the capture element 150 into the catheter 4 or catheter 107, the capture element 150 may be collapsed and then inverted back into the catheter 4, 107 thereby trapping the obstruction in the catheter 4, 107 itself.

Figure 20:
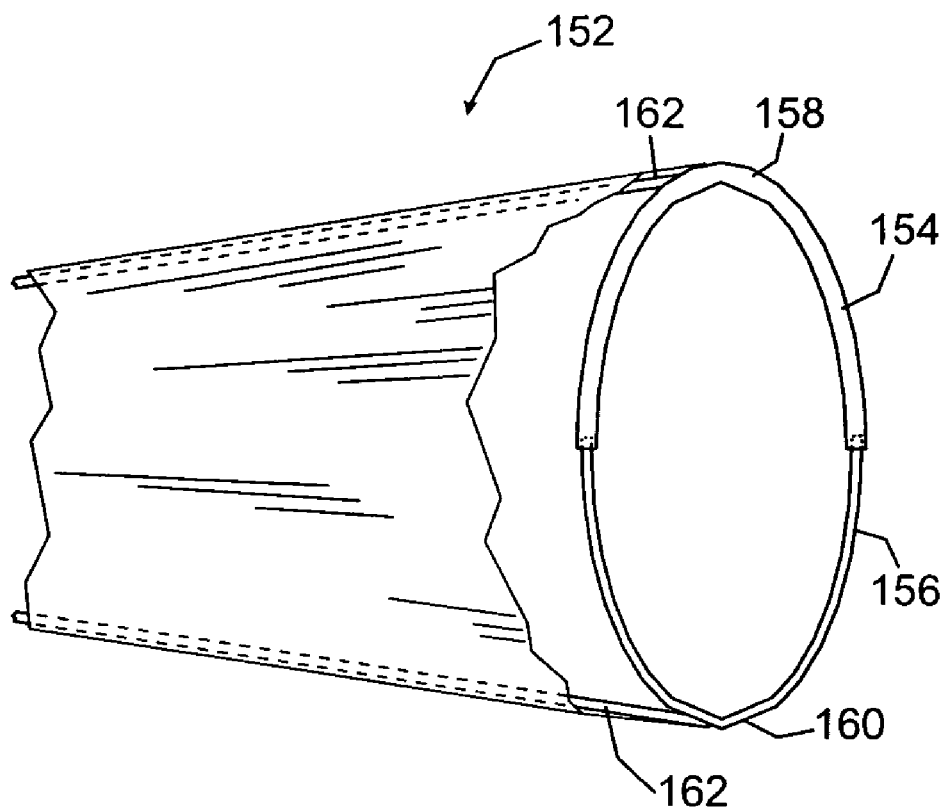
FIG. 20 shows another support structure for the capture element with the support structure in an expanded position.
Figure 21:
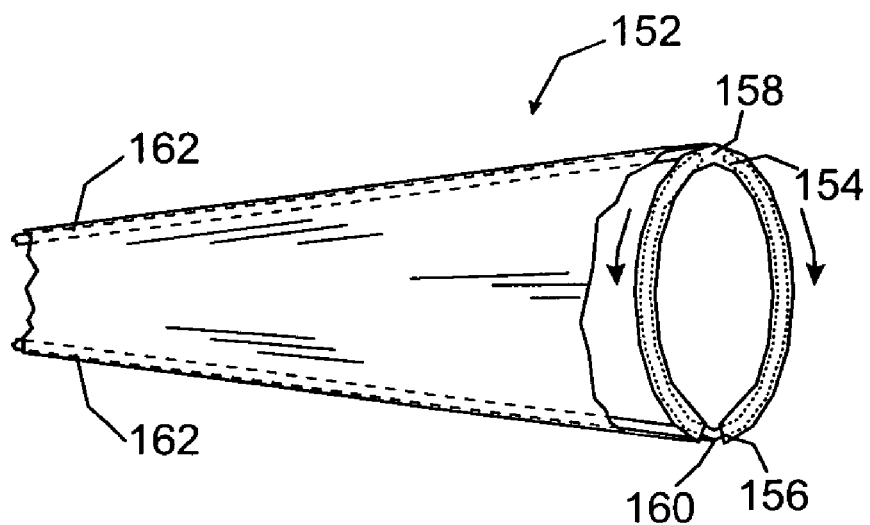
FIG. 21 shows the support structure of FIG. 20 in a collapsed position.
Figure 22:
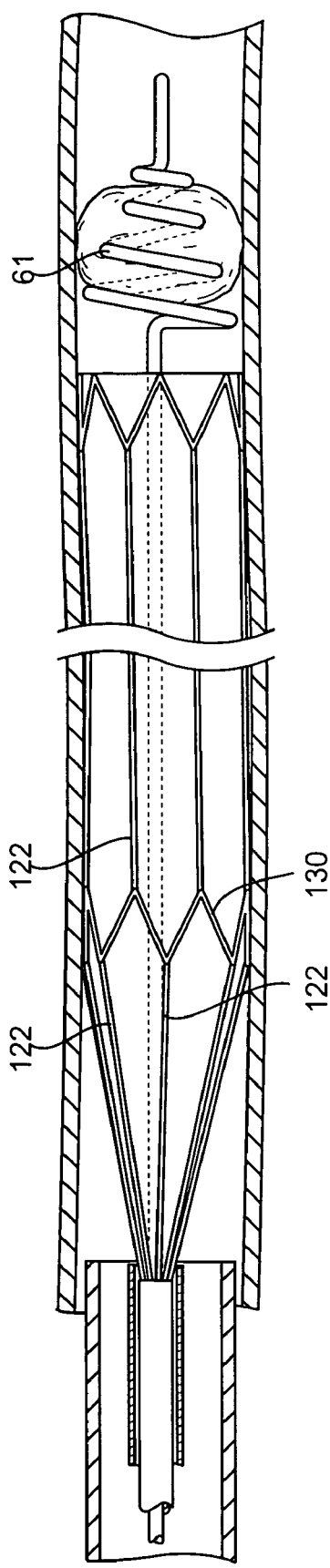
FIG. 22 shows still another support structure for the capture element.

Referring to FIGS. 20 and 21, the distal end of yet another capture element 152 is shown in which the same or similar reference numbers refer to the same or similar structure. The capture element 152 has a self-expanding support structure 154 with an expandable loop 156 at the distal end. The loop 156 has a tube 158 which receives a wire 160 at both ends. The slidable connection between the tube 158 and wire 160 permits the loop 156 to contract and expand between the positions of FIGS. 20 and 21. Struts 162 extend from the loop which engage the catheter to collapse the loop 156. The cover 114 is attached to the loop 156 by any suitable method. The capture element 152 is used in any manner described herein. The capture element 152 is used in any manner described herein and those methods are incorporated here.

Figure 25:
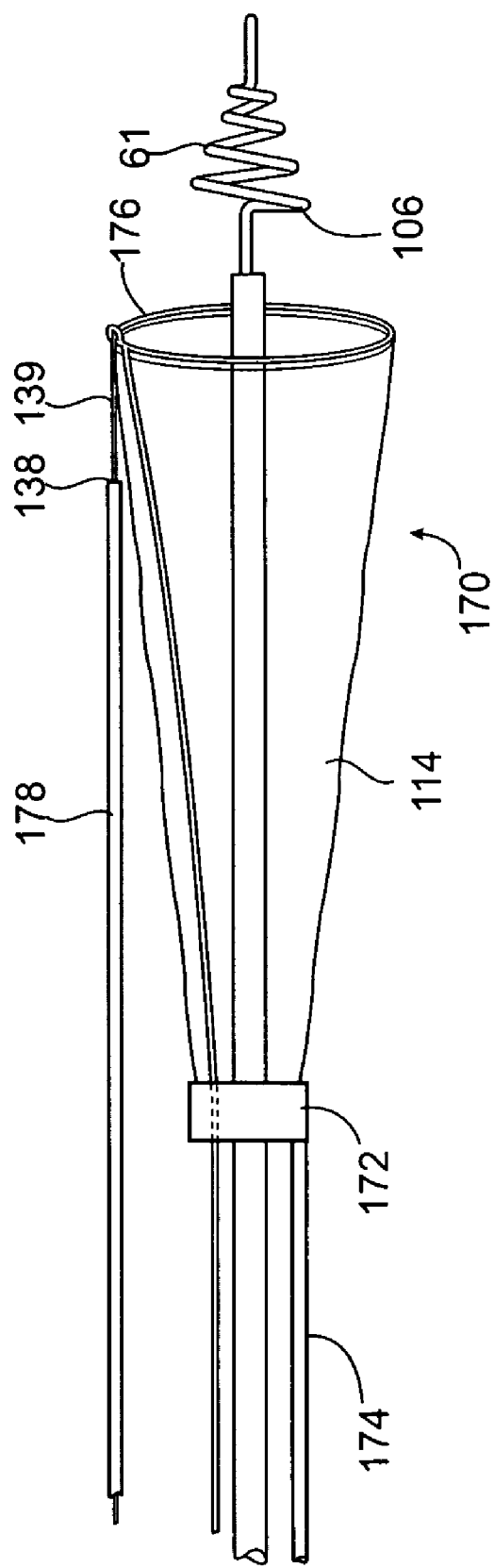
FIG. 25 shows another capture element.
Figure 28:
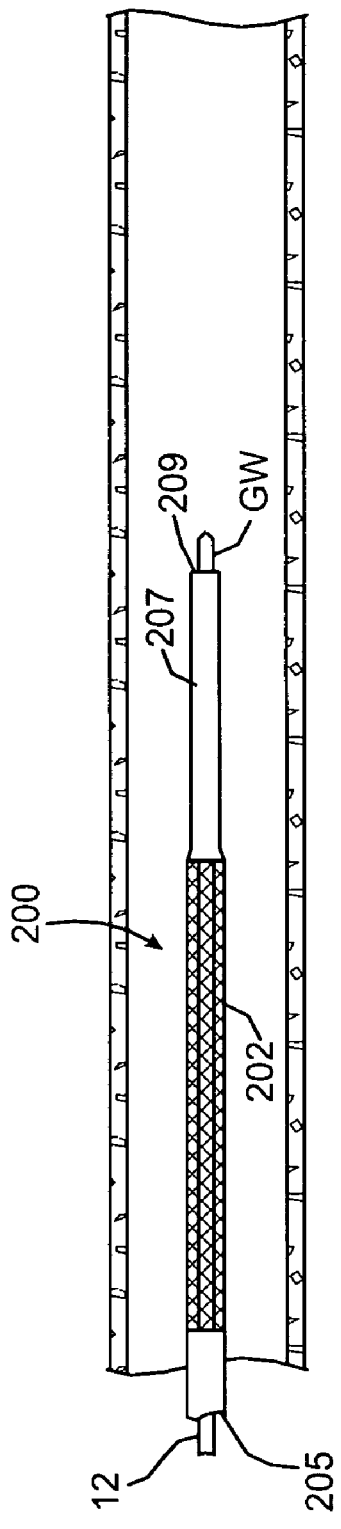
FIG. 28 shows another device for capturing an obstruction.

Referring to FIG. 25, still another device 170 is shown wherein the same or similar reference numbers refer to the same or similar structure. The device 170 is similar to the device of FIG. 15 in that the device 170 may be selectively expanded and collapsed by the user. The device 170 has a collar 172, which may also be a continuous sheath or tube, which slides over the catheter 107 or sheath 12. The engaging device 106 passes through the catheter 107 or sheath 12 (FIG. 10) and is used in the manner described herein. A 174 wire, or other elongate member, is coupled to the collar 172 for advancing and manipulating the collar 172.

The cover 114 is coupled to a loop 176 which is selectively expanded by the user as now explained. The loop 176 is manipulated with the actuator 138 which may be any suitable mechanism. The actuator 138 has a wire 139 passing through an actuator tube 178 and may also include the stable arm 142. The wire 139 is coupled to the loop so that movement of the wire 139 opens and closes the loop 176. The actuator tube 178 may be simply advanced to cinch the loop 176 closed. The loop 176 is preferably naturally biased toward the open position and is held closed by the tube 178.

The device 170 is used in substantially the same manner as the other devices described herein and discussion of those methods are specifically incorporated here. The device 170 may be advanced by itself through the vasculature with the tube 178 holding the loop 176 in the closed position. The cover 114 is advanced by manipulating the tube 178, wire 139 and wire 174. The cover 114 is advanced over the catheter 107 or sheath 12 and the tube 178 is retracted to permit the loop 176 to expand. The obstruction is then introduced into the cover 114 and the cover 114 is then closed by advancing the tube 178 to cinch the loop 176 closed. The actuator 138 may also be manipulated to open or close the loop 176 together with the tube 178 or independently of the tube 178.

Referring to FIGS. 26 and 27, still another device 180 is shown wherein the same or similar reference numbers refer to the same or similar structure. The device 180 has the cover 114 and a loop 182 coupled to the distal end of the cover 114. Stabilizing struts 184 extend from an end 186 of a tubular body 188 to the loop 182. Actuating arms 190 extend through the body 188 and are also attached to the loop 182. The arms 190 are manipulated to move the loop 182 between the collapsed and expanded positions of FIGS. 26 and 27. The engaging device 106 passes through the body 188 and may be delivered through the catheter 107 or sheath 12. The device 180 is used in substantially the same manner as the device of FIG. 15 and discussion of those methods are incorporated here.

Referring to FIGS. 28-33, another capture element 200 is shown for capturing an obstruction. The capture element 200 has an inverting portion 202 that inverts to entrap the obstruction. The capture element 200 is then withdrawn into the guide catheter 4 (FIG. 1) for removal of the obstruction from the patient.

Figure 31:
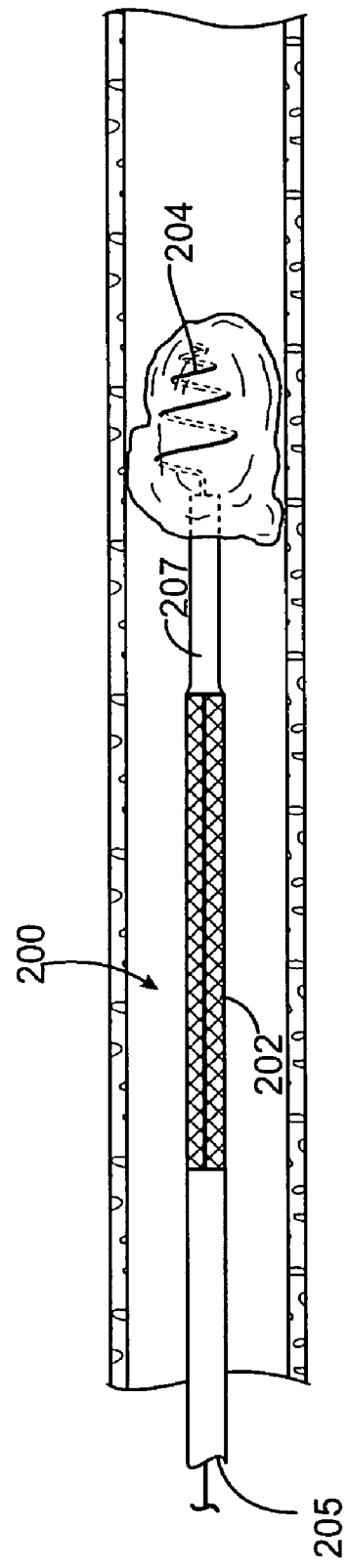
FIG. 31 shows the element engaging the obstruction.

Referring to FIG. 31, the engaging element 204 is shown engaging the obstruction. The element 204 may be any suitable element such as the obstruction engaging elements and removal devices described herein. The element 204 passes through a lumen 205 in the capture element 200. The engaging element 204 may be advanced through the capture element 200 by itself or may be contained within the microcatheter 10 or sheath 12 (FIGS. 1 and 2) which is advanced through the capture element 200.

Figure 29:
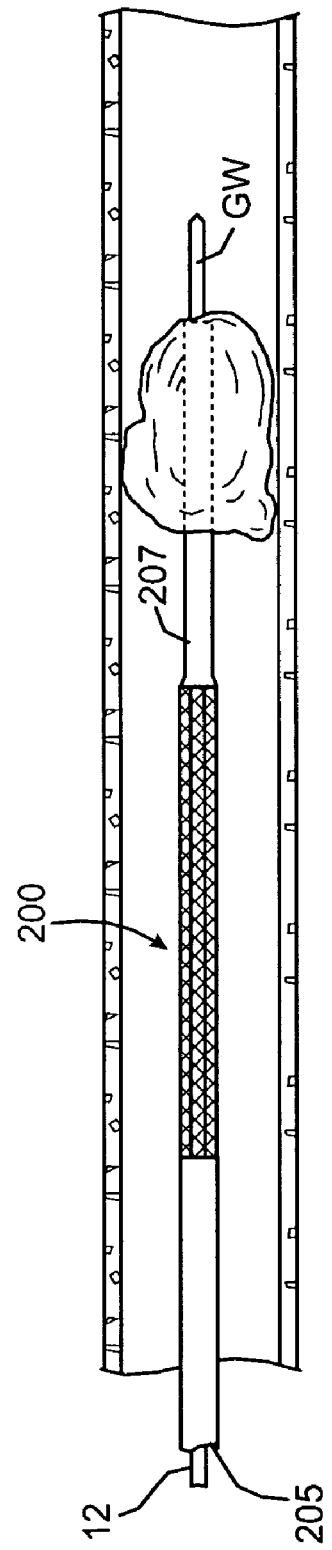
FIG. 29 shows the capture device of FIG. 28 advanced at least partially into engagement with the obstruction.
Figure 30:
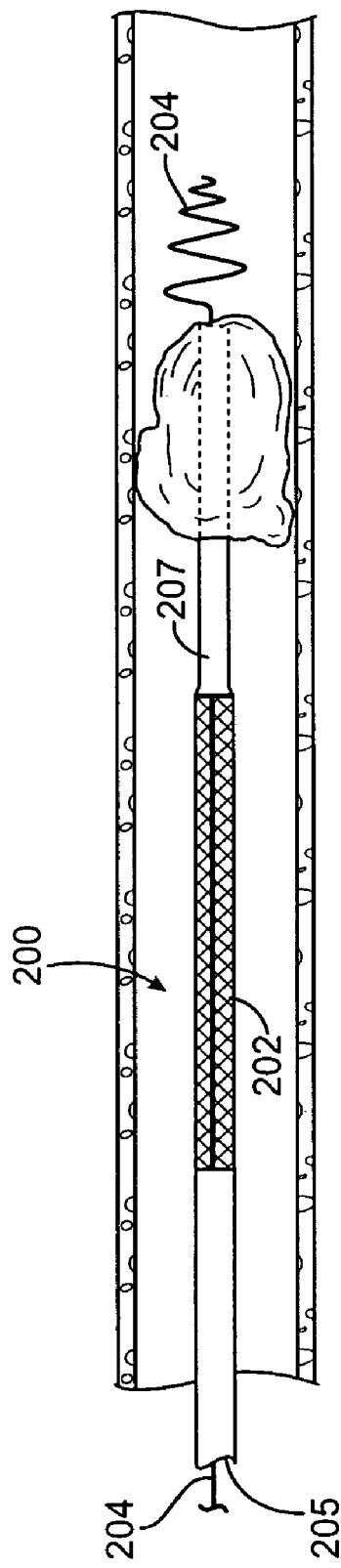
FIG. 30 shows an obstruction engaging element advanced through the capture element.

The capture element 200 has a distal portion 207 which is flexible and which may be partially contained, engaged or otherwise in contact with the obstruction as shown in FIG. 29. The distal portion 207 may also invert but preferably does not invert. The distal portion 207 necks-down at a distal end 209 to a size smaller than the guidewire GW so that the capture element 200 is advanced together with the guidewire. Of course, the capture element 200 may also be advanced by itself after introduction of the guidewire and may be contained within or advanced over another catheter without departing from the invention.

Figure 32:
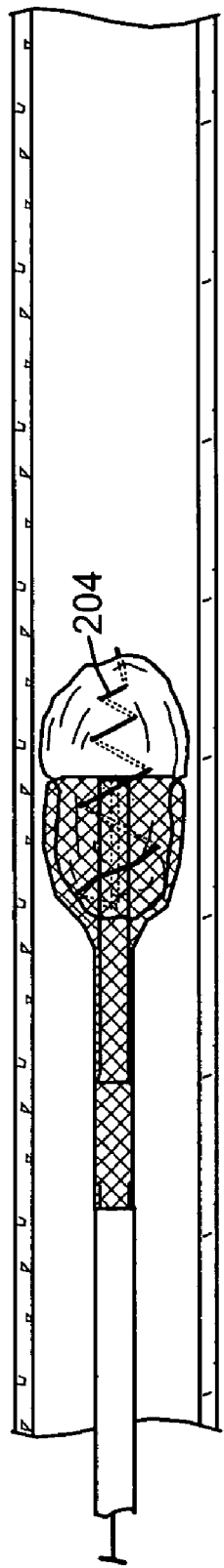
FIG. 32 shows the obstruction partially contained within the capture element.
Figure 33:
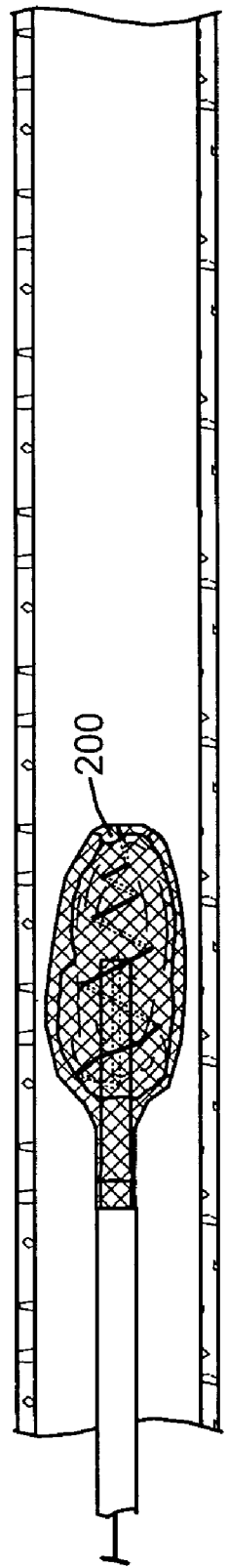
FIG. 33 shows the obstruction completely contained within an inverted portion of the capture element.
Figure 34:
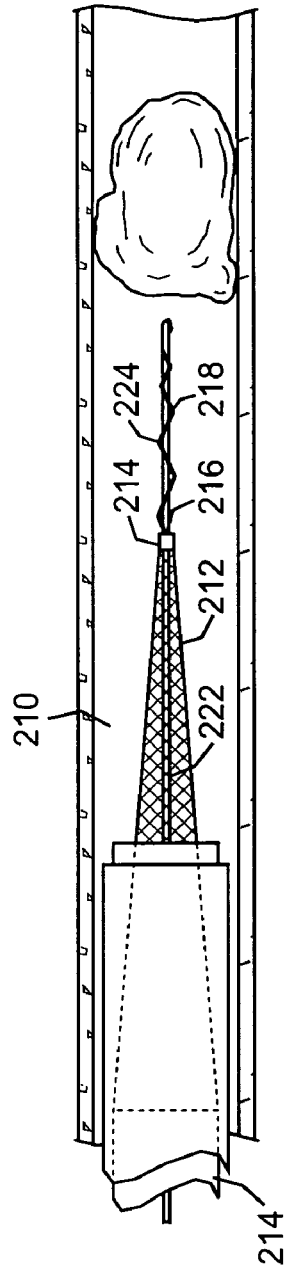
FIG. 34 shows still another device for capturing an obstruction.
Figure 35:
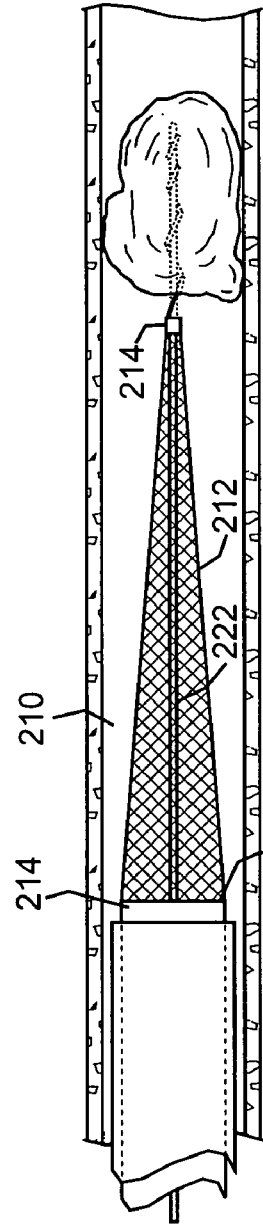
FIG. 35 shows the element engaging the obstruction.
Figure 36:
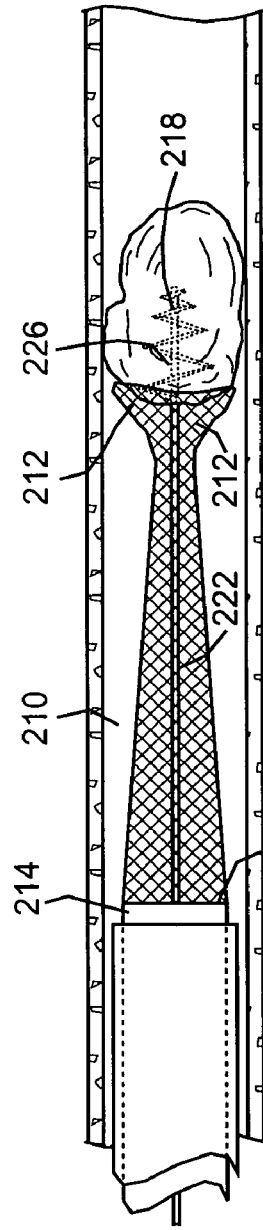
FIG. 36 shows the inverting portion beginning to invert to capture the obstruction.
Figure 39:
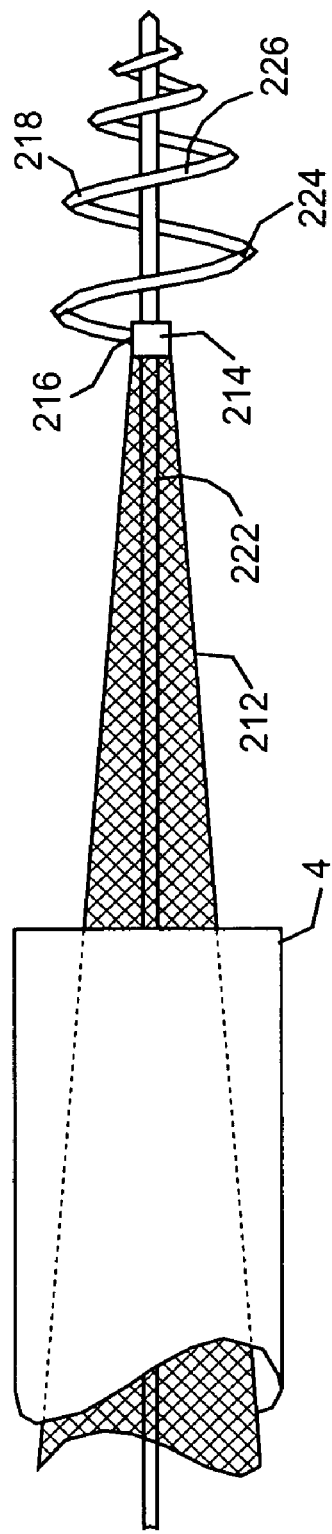
FIG. 39 shows the distal end of the device of FIGS. 34-38 with the engaging element expanded.
Figure 40:
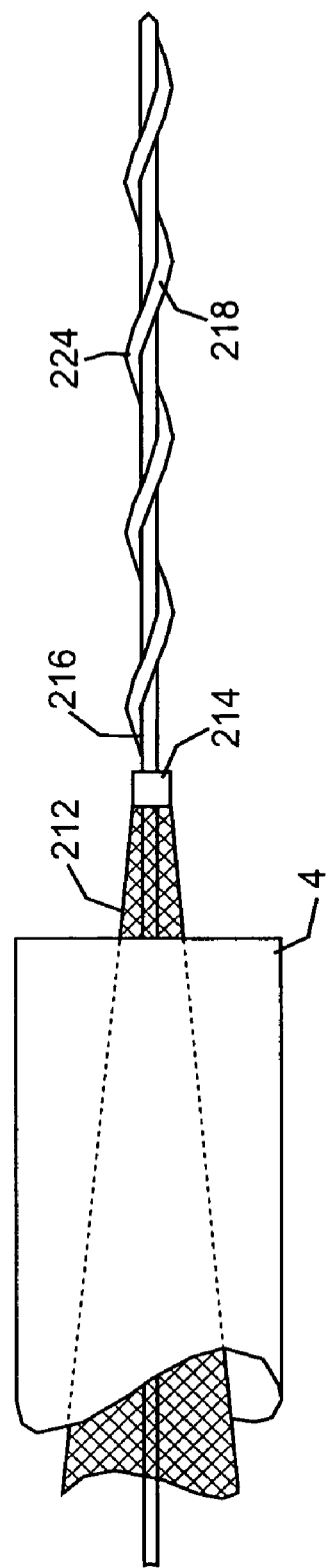
FIG. 40 shows the distal end of the device of FIGS. 34-38 with the engaging element collapsed.

The element 204 engages the obstruction in any suitable manner. The inverting portion 202 is then inverted by applying a compressive force to the inverting portion 202. The compressive force is applied by moving the capture element 200 relative to the engaging element 204 which causes the element 200 and/or obstruction to compress the inverting portion. Continued relative movement moves the obstruction into the inverted capture element 200 as shown in FIGS. 32 and 33 to capture the obstruction. The capture element 200 is then moved into the guide catheter 4 (FIG. 1) for removal from the patient. The capture element 200 may be made of any suitable materials. For example, the distal portion 207 may be made of any suitable polymeric material such as those described herein and the inverting portion 202 may be made of a braided or woven material or fabric made of fibers or filaments of nitinol, stainless steel, polymer or other material.

Referring to FIGS. 34-40, another capture element 210 for removing an obstruction is shown wherein the same or similar reference numbers refer to the same or similar structure. The capture element 210 also has an inverting portion 212 connected to an end 213 of a delivery element 214 which may be a hollow tube, sheath or catheter. The distal end of the capture element 210 has a collar 214 attached to a proximal end 216 of an engaging element 218. A distal end 220 of the obstruction engaging element 218 is attached to an inner element 222 such as a wire, mandrel or guidewire. The collar 214 slides over the inner element 222 so that when the inner element 222 and delivery element 214 are movable relative to one another. Relative movement between the inner element 222 and delivery element 214 moves the obstruction engaging element 218 between the expanded and collapsed positions (FIGS. 39 and 40) and also can collapse the capture element 210. The engaging element 218 is similar to the other elements and devices described herein in that the element has a filament 224 which is tensioned to collapse the filament 224. The filament 224 forms coils 226 around the inner element 222.

Figure 1:
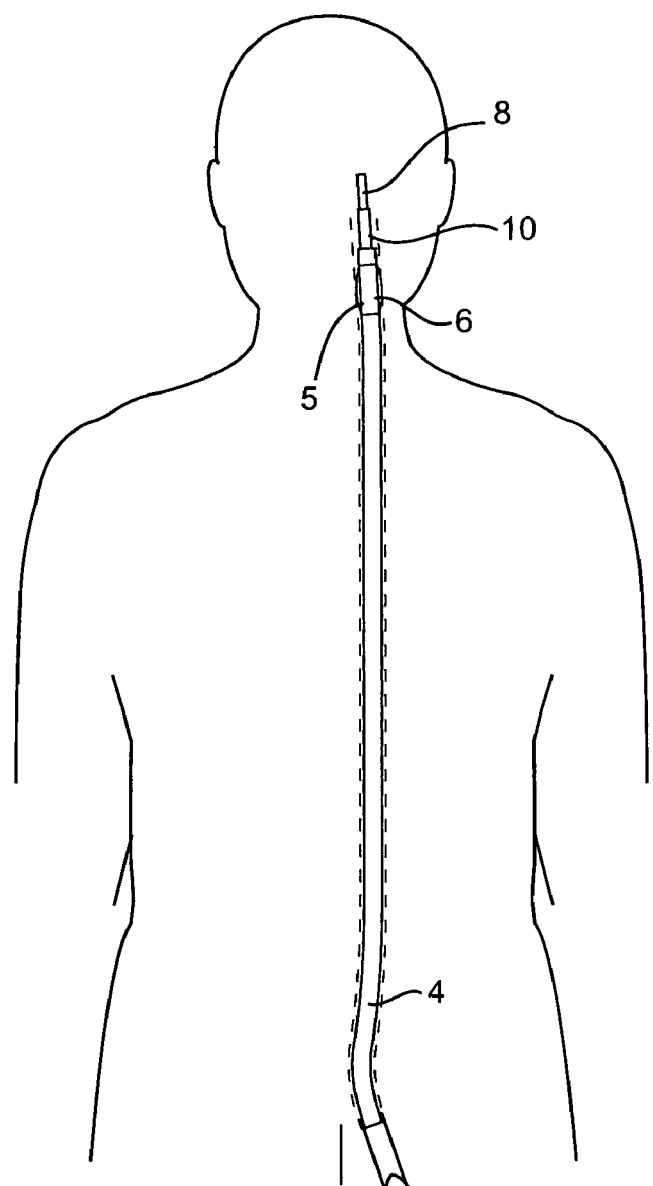
Figure 2:
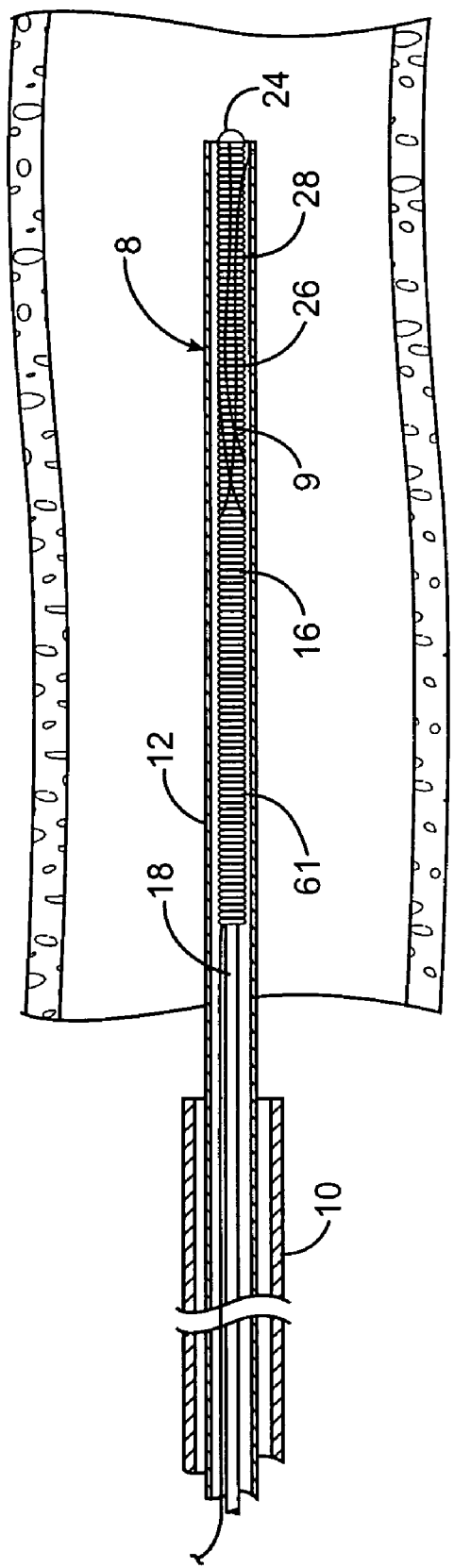

The capture element 210 and obstruction engaging element 218 are advanced through the patient in either the sheath 12 or microcatheter 10 (FIGS. 1 and 2). The capture element 210 and obstruction engaging element 218 are then positioned distal to the obstruction and the obstruction is engaged with the element 218. The capture element 210 and engaging element 218 are then moved relative to one another to invert the capture element 210 as described above.

Figure 41A:
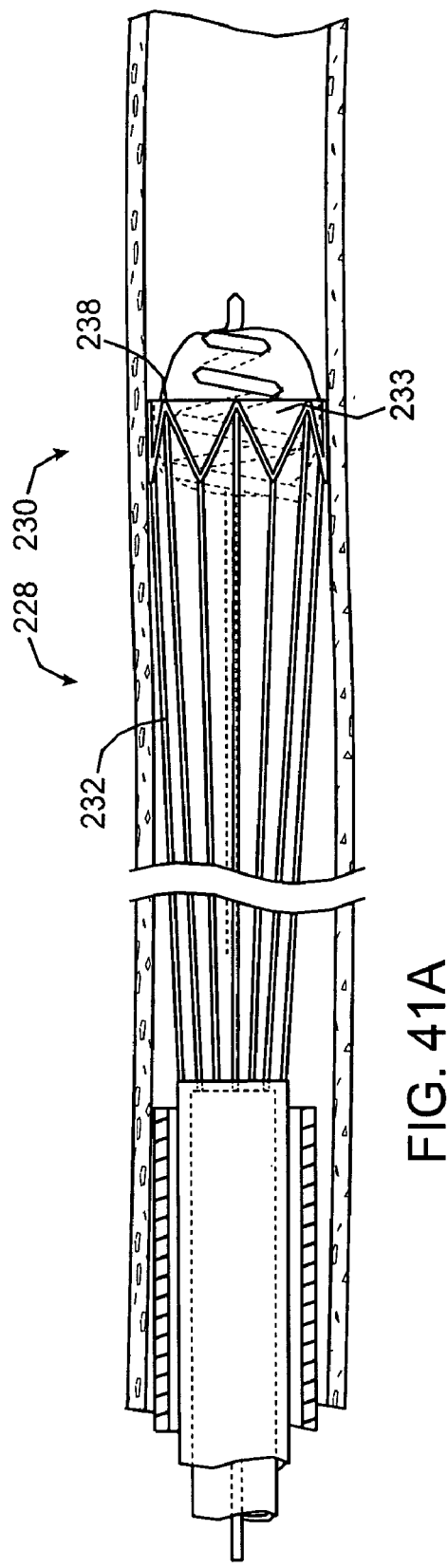
FIG. 41A shows an actuator for a medical device having which has a deformable frame being used as an obstruction capture device.
Figure 41B:
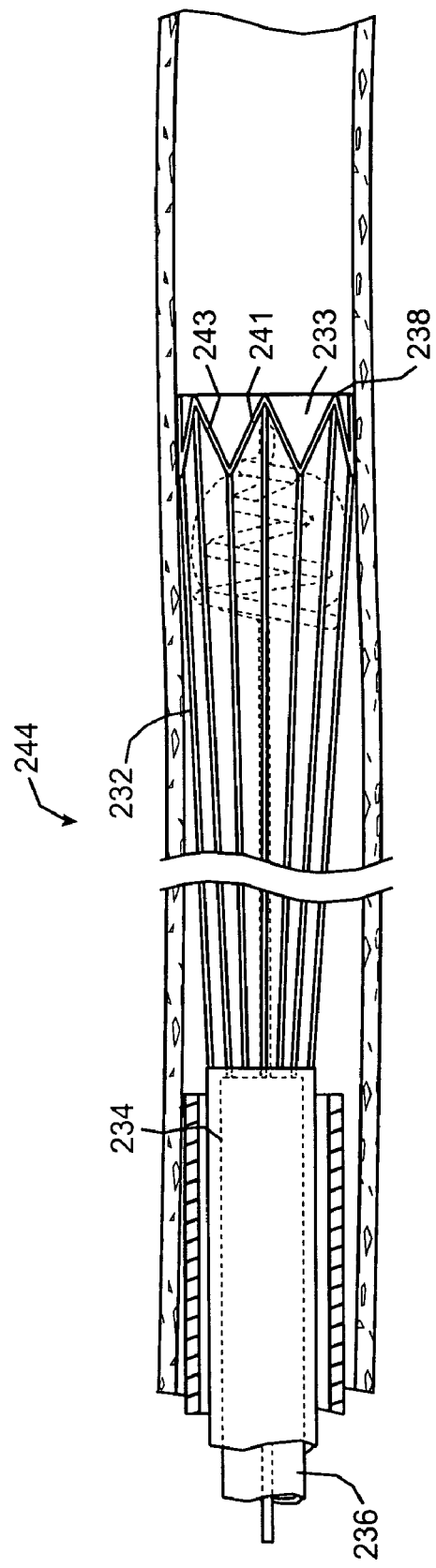
FIG. 41B shows the capture device with an obstruction contained therein.
Figure 43A:
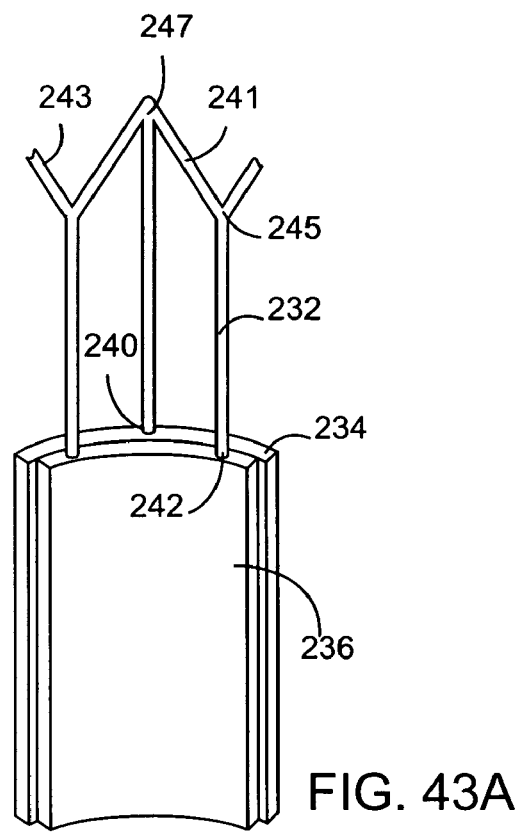
Figure 43C:
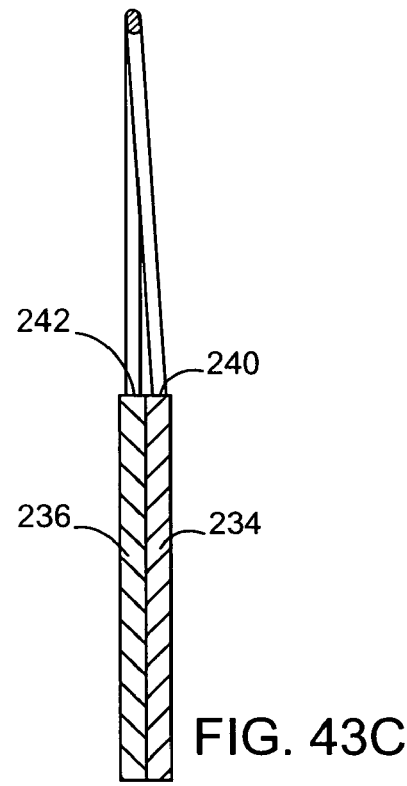
Figure 43B:
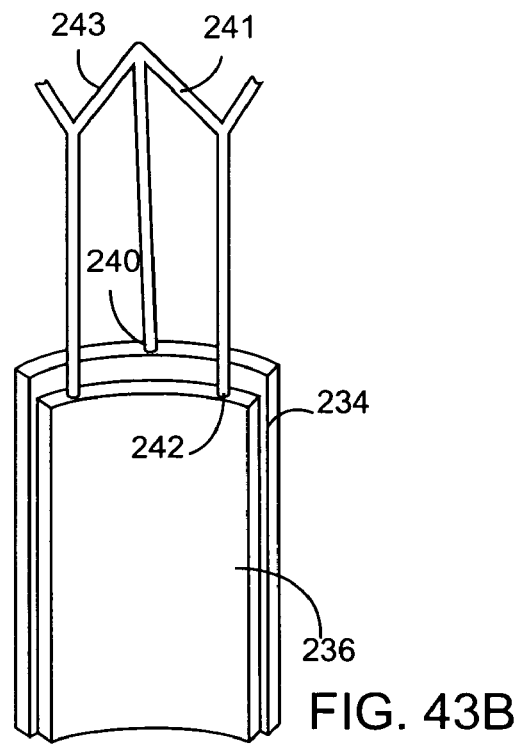
Figure 43D:
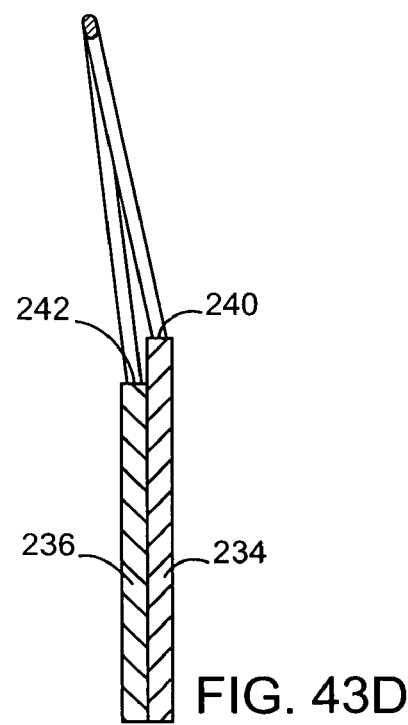

Referring to FIGS. 41-43, another aspect of the present invention is shown which provides an actuator 228 for a medical device 230. The actuator 228 may be used for actuating any medical device and a specific example is a capture element or an obstruction removal device. The medical device 230 has a frame 232, an outer member 234 and an inner member 236 positioned within the outer member 234. The frame 232 extends distally from the inner and outer members 236, 234.

The frame 232 has a distal end 238 which moves between the open (FIGS. 41A and B) and closed (FIGS. 42A and B) positions. The frame 232 has a first set of connectors 240 coupled to the outer member 234 and a second set of connectors 242 coupled to the inner member 236. The inner and outer members 236, 234 are moved relative to one another so that the frame 232 is deformed to open and close the distal end between the positions of FIGS. 41A and B and 42A and B. The inner and outer members 236, 234 are preferably tubes but may be any other suitable structure that permits longitudinal movement of the connectors 240, 242 in the manner described. The connectors 240, 242 extend longitudinally to a ring 241 formed of V-shaped elements 243. The connectors 240 attached to the inner member 236 are coupled to intersections 245 of the ring 241 and the other connectors 240 are attached to the other intersections 247 of the ring. Stated another way, the connectors 240, 242 are attached at spaced apart positions on the ring with one connector 240 between each pair of connectors 242. The frame 232 is preferably integrally formed in a manner similar to a stent. For example, the frame 232 may be formed by removing material from a tube to provide the frame structure.

A cover 233 may be provided over or under the frame 232 so that the frame 232 acts as an actuator 244 to open and close the cover 233. The cover 233 may be used in the same manner as any of the capture elements described herein. To this end, any of the obstruction engaging elements described herein may be used with the device to trap and remove obstructions.

Referring to FIGS. 44 and 45, still another medical device 250 is shown which is similar to the medical device 230 of FIGS. 41-43. The medical device also has a frame 252 having a distal end 254 which opens and closes. The frame 252 is made of a shape memory material which either recovers the open or closed position when heated. The shape memory material may be heated in any suitable manner including use of a heated fluid or by applying electrical energy which heats the frame 252 to cause the frame to assume the recovered shape. FIG. 45 shows the frame 252 assuming the collapsed shape upon application of electrical energy from an energy source 253. The cover 233 may also be provided so that the frame acts as an actuator for still another capture device. FIG. 45 show the medical device 250 being used to capture an obstruction. The device 250 is then withdrawn into the guide catheter or other suitable catheter for removal of the obstruction.

Referring to FIGS. 46-51, still another actuator for a medical device 256 is shown. The characteristics of the medical device 256 may be used to form any device. The medical device 256 has a plurality of longitudinally extending fingers 258. The fingers 258 are normally in a relatively straight configuration. The fingers 258 are bent inward so that a distal end 260 closes (FIG. 47). The fingers 258 may be attached to the cover 233 to open and close the cover 233 with the fingers 258. The fingers 258 are preferably bent by tensioning flexible, elongate members 262. The elongate members 262 may be attached to an inner member 264 (FIGS. 46 and 47) or an outer member 265 (FIGS. 48 and 49). Any of the obstruction engaging elements may be used with the medical device to remove an obstruction in any manner described herein. For example, FIGS. 50 and 51 show the medical device 256 being used to capture or remove an obstruction. The device 256 may be used to capture or engage the obstruction by itself or in cooperation with any a suitable engaging element 257.

Referring to FIGS. 52-55, another obstruction engaging element 270 is shown. The obstruction engaging element 270 includes a filament 272 which forms windings or coils 274. The windings 274 may take any suitable shape such as helical. The obstruction engaging element 270 is advanced to an obstruction in any manner described herein. For example, the obstruction engaging element 270 may be contained within the sheath 12 or catheter 10 (FIGS. 1 and 2) and advanced through the obstruction. The obstruction engaging element 270 is then advanced out of the sheath 12 or catheter 10 (FIGS. 1 and 2) to permit the obstruction engaging element 270 to expand.

When the element initially expands, the coils 274 do not overlap when viewed along a longitudinal axis L. The element 270 is then engaged by manipulating the element 270. After the obstruction has been engaged, the element 270 is rotated which tends to open the coils 274. This causes one or more proximal coils 274 to prolapse over other coils to ensnare the obstruction. Stated another way, the element 270 initially extends distally in a relatively continuous manner. After rotating the element 270, the element extends distally, then proximally, then distally again. Stated yet another way, the coils are manipulated so that they appear to overlap when viewed along the longitudinal axis L. The prolapsed or overlapping coils 274 may provide an even more secure engagement to the obstruction. The element 274 may also be formed to have the overlapping or prolapsed sections when in the natural, unbiased and expanded position as shown in FIG. 54.

Referring now to FIGS. 56 and 57, still another device 280 for removing an obstruction is shown. The device 280 may be used in any suitable manner described herein. For example, the device 280 may be advanced by itself or advanced while contained in a sheath or catheter. The sheath or catheter 281 holds the device 280 in a substantially straight configuration. The device 280 has an elongate element 282, such as a wire 284, which expands to the expanded shape of FIG. 57 similar to other embodiments described herein. The elongate element 282 has a distal end 286 coupled to an insertion element 288. A proximal end 290 of the elongate element 282 is coupled to a collar 292, which slides on the insertion element 288. Sliding of the collar 292 permits the elongate element 282 to move between the collapsed and expanded positions of FIGS. 56 and 57. The insertion element 288 also has a stop 294, which prevents movement of the collar 292 beyond the position of FIG. 57.

Still another device 300 is shown in FIG. 58. The device 300 is similar to many of the other devices described herein and may be used in any manner described herein. The device 300 is formed by an elongate element 302, such as a wire 304, which forms a number of coils 306. The device 300 has larger coils 308 at a distal portion 310 and smaller coils 312 along an intermediate portion 314. The smaller coils 312 are preferably stiffer than the larger, distal coils 308. In this manner, excessive elongate of the device can be reduced since the stiffer coils 312 help to resist elongation of the element 302 when the element is pulled. The device 300 is also particularly useful when using the following routine to remove an obstruction. The device 300 is positioned in a catheter or sheath which is advanced through the obstruction. The distal coils 308 are expanded distal to the occlusion but may be expanded within the obstruction as well. The device 300, and catheter if necessary, are then manipulated to expose the intermediate portion 314 within the obstruction. The intermediate portion 314 expands within the obstruction and engages the obstruction. The stiffer, intermediate portion 314 resists elongation when withdrawing or moving the obstruction so that the device 300 maintains good contact with the obstruction. The larger, distal coils 308 help to trap the obstruction and prevent parts of the obstruction from trailing or escaping removal. The device 300 also has a proximal portion 316, which may be expanded proximal to the occlusion so that the occlusion is substantially trapped between the proximal and distal portions 316, 310.

Referring to FIG. 59, another device 319 is shown which is similar to the device of FIG. 58. The device 300 has distal, intermediate and proximal portions 318, 320, 322. The proximal portion 322 differs from the proximal portion 316 of FIG. 58 in that the proximal portion 322 winds distally, then proximally, then distally again. The back-and-forth winding of the proximal portion 322 increases the stiffness of the proximal portion 322 which may help resist elongation of the device during withdrawal of the obstruction. If the device begins elongating during manipulation of the obstruction, the obstruction will engage the proximal portion which then helps to resist further elongation of the device. The device 319 may be used in the manner described above in connection with FIG. 58 in that the intermediate portion may be deployed within the obstruction.

Referring to FIGS. 60 and 61, an obstruction removing element 327, which may be any of the devices described herein or another suitable device, may also be covered with a flexible cover 328. In the preferred embodiment, the element 327 is an elongate element 327 such as a wire. The flexible cover 328 is preferably not rigidly adhered or attached to the element 327 so that the cover 328 has some freedom to move on the element 327. The cover 328 may be a flexible tube 330, such as an ePTFE tube or ribbon, which extends over the element 327. The tube 330 is very flexible and provides no structural properties to the element 327 and essentially follows the shape of the element 327. The tube 330 may simply extend through the element 327 or the element 327 may pass in and out of the tube as shown in FIG. 60. The cover may also be a braided structure 332 positioned over the element 327 as shown in FIG. 61. The cover 328 adds no significant stiffness or structural properties to the element 327 and can also be made very small and, therefore, does not substantially impact the size or advanceability of the device 327. When deployed, however, the cover 328 may fold, crease or bunch up which tends to increases the surface area of the element 327 for engaging the obstruction when expanded. The braided cover 332 can also help to filter the fluid flow to trap loose parts of the obstruction.

Referring to FIG. 62, another device 334 for removing an obstruction is shown. The device 334 is similar to other devices described herein and all methods described herein may be used with the device 334. The device 334 has a first elongate element 336 which may form coils 338 or other suitable structure when expanded. A second elongate element 340 extends next to the first elongate element 336 and forms substantially the same expanded shape as the first elongate element 336. The second elongate element 340 may be a filament 342, such as suture 346, which does not add significant structural properties to the device 334 similar to the cover 328 described in connection with FIGS. 60 and 61. The suture 346 may be attached to the first elongate element 336 at various points so that the suture 346 essentially follows the shape of the first elongate element 336. Alternatively, the second elongate element 340 may be a wire or ribbon which provides some structural properties. Referring to FIG. 63, for example, the first elongate element 336 is a round coil while the second elongate element 342 is a ribbon coil. The second elongate element 342 is wrapped around the first elongate element 336 at the distal end and extends parallel to the first elongate element 336 through an intermediate 344 or expandable section. The second elongate element 342 is again wrapped around the first elongate element 336 at a proximal portion 346. The second elongate element 342 may also form reinforcing 348 for the insertion element 350 as shown in FIG. 63 by encasing the second elongate element 342 in suitable polymer 352 to form a shaft as is known in the art.

Referring to FIG. 64, still another device 356 is shown for removing an obstruction. The device 356 has a proximal obstruction removing element 358 and a distal obstruction removing element 360. The elements 358, 360 are preferably independent so that they may be manipulated independently. Each of the obstruction removing elements 358, 360 may be any of those described herein or any other suitable structure. In one aspect of the invention, the distal obstruction removing element 360 may be deployed within or distal to the obstruction. The other element 358 is deployed on the proximal side of the obstruction, or within a proximal portion of the obstruction, to provide further control and entrapment of the obstruction. The proximal obstruction removing element may also be used to resist and prevent excessive elongation of the distal obstruction removing element 360 when the distal removing element 360 is pulled to move the obstruction. The elements 358 may extend through the same multi-lumen catheter or may be provided in separate catheters without departing from the scope of the invention.

Referring to FIGS. 65-67, still another device 362 for removing an obstruction is shown. The device 362 has an insertion element 364 and struts 366, preferably 2-4, extending from a distal end of the insertion element 364. Arms 368 extend from the struts 366 to form a cage-like structure 370. The device 362 preferably has at least two arms 368, preferably 2-4 arms, extending from the end of each strut 366. For example, FIG. 64 shows two struts 366 with three arms 368 extending from each strut 366. In another example, three struts 366 may be used with two arms 368 extending from each strut 366. The struts 366 are relatively short when viewed along the longitudinal axis and may be less than ½, and more preferably less than ⅓, the length of the arms 368. The distal end of the arms 368 are coupled together to form a tip 372 of the cage-like structure 370.

Referring now to FIGS. 68 and 69, still another device 374 is shown for removing obstructions. The device 374 has a cage-like structure 376 formed by a number of elongate elements 378 such as wires 380. The wires 380 are coupled together at proximal and distal ends 382, 384 to form the cage-like structure. The wires 380 may be substantially independent and are preferably not braided or woven. The elongate elements 378 may be wound helically, although other shapes and patterns may be used, with the elements 378 all wound in the same direction. Although cross-members or cross-elements may be provided, it is preferably to omit such cross-members and cross-elements. An advantage of providing the relatively independent elements 378 is that the entire structure may be collapsed to a smaller size than typical woven or braided elements. Referring to FIG. 69, an end-view of the device 374 shows that a larger spacing 386 between two of the wires 380 to permit the obstruction to pass into the opening. The other end, such as the distal end, preferably has a more symmetrical pattern to minimize the size of the openings and prevent the obstruction from escaping through the distal end. The proximal portion may also form larger coils than the distal section so that the obstruction may pass through openings in the proximal portion but is prevented from escaping through the distal end.

Referring now to FIGS. 70-79, various other devices for removing an obstruction are shown. The devices are held in a substantially straight, collapsed position when contained in a sheath or catheter as described herein. Referring to FIG. 70, an elongate element 392, such as a wire 394, forms a number of discrete structures 396 when permitted to expand. The discrete structures 396 may take any shape such as a circular structure (FIG. 72), or a flower-petal like structure (FIGS. 70 and 75-78). In one aspect, the structures 396 may be substantially parallel to one another (FIG. 71). In another aspect, the discrete structures extend from a side of an otherwise straight portion of the wire (FIG. 73) or may be centered with respect one another (FIG. 74). The discrete structure 396 may also have different sizes (FIGS. 73 and 74). The discrete structures 396 may also be oriented to create an interfering pattern as shown in the end view of FIG. 78. The discrete structures 396 may also be formed somewhat continuously as shown in FIG. 79.

Referring to FIGS. 80 and 81, still another obstruction removing device 400 is shown. The obstruction removing device 400 has a loop 402 and a basket 404 attached to the loop 402. The basket 404 may be formed in any suitable manner such as with a number of filaments 406 or wires. Of course, an integral structure, bag or any other structure may be used to form the basket 404. The basket 404 primarily forms a chamber 408 to receive the obstruction. The loop 402 is deflected into the collapsed position of FIG. 81 and expands to the position of FIG. 80. The loop 402 is an elongate oval in the collapsed position with the loop 402 generally lying in a plane P1 which is about 0-25 degrees relative to a longitudinal axis LA of the device. When the loop 402 expands, the loop 402 becomes less elongate and may form a circle. The loop 402 lies in a plane P2 which is preferably about 45-135 degrees, more preferably 70-110 degrees, relative to the longitudinal axis when LA in the expanded position.

The loop 402 may have a varying size or may have a constant perimeter size. In the embodiment of FIG. 80, the loop 402 substantially maintains the same perimeter size when moving between the expanded and collapsed positions with the loop 402 being simply deformed when collapsed. The loop may be formed by a single filament or wire 406 with the wire 406 having first and second ends 410, 412 coupled to an insertion element 414. The first and second ends 410, 412 are attached to the insertion element 414 with a platinum coil 416 wrapped around the first and seconds ends 410, 412 and the insertion element 414. Of course, any other method may be used to attach the loop including simply soldering or gluing the loop to the insertion element or using two or more wires or elements attached to one another. Thus, it can be appreciated that the deformable loop of the present invention may be provided in a number of different ways without departing from the scope of the invention. The wires 406 may also be wrapped with a radiopaque element such as platinum wire.

In use, the device of FIGS. 80 and 81 is deployed distal to the obstruction so that the loop 402 expands distal to the obstruction. The insertion element 414 is then manipulated to move the obstruction into the chamber 408 of the basket 404. The loop 402 may be sized to expand to a size and shape similar to the vessel in which it is being deployed. The loop 402 may then be partially or totally collapsed to prevent escape of the obstruction or parts thereof. The device is then removed in any suitable manner such as through a guide catheter.

Referring to FIGS. 82 and 83, another device 420 is shown. The end view of FIG. 82 shows a plurality of loops 422 formed. The loops 422 are oriented at different positions relative to a longitudinal axis L of the device and may be angularly displaced as shown in FIG. 82. The loops are angularly displaced relative to one another by about 60-90 degrees relative to the longitudinal axis L. The term loop as used herein does not necessarily mean that the elongate element forms a closed structure but rather forms a loop-like structure when viewed from an end as shown in FIG. 82. The device 420 may have at least 3, 8 or 12 loops. Stated another way, the device 420 may have about 6-40 loops. Similar to the other embodiments described above, the device 420 is held in the collapsed position by a catheter or sheath 421 or other suitable structure.

The loops 422 may be formed in any suitable manner. For example, the loops 422 may be formed by wrapping an elongate element 424, such as a wire, around at least two mandrels (not shown). The elongate element 424 is wound around the mandrels to form a repeating series of loops. Each of the successive loops 422 may be formed by a different mandrel. Although each of the loops 422 may be formed by one mandrel, the loops 422 may also be formed by more than one mandrel. The loops are relatively elongate as shown in FIG. 83. The loops are generally helical and may have an angle A of about 20-60 degrees so that they are somewhat stretched and elongate.

While the above is a description of the preferred embodiments of the invention, various alternatives, substitutions and modifications may be made without departing from the scope thereof, which is defined by the following claims. Thus, the preferred embodiments should not be taken as limiting the scope of the invention. For example, although all of the obstruction removal devices described herein are self-expanding structures, the obstruction removal devices may also have actuating mechanisms for moving the engaging element between the expanded and collapsed positions. Furthermore, the present invention is directed to a number of separate inventions and each of these inventions may be claimed independently of one another. Each feature, aspect and advantage of the invention may be claimed independent of one another without departing from the scope of the invention. For example, use of the power source 14 is independent of the using the intermittent wound sections 42 but may be used with any of the devices and methods described herein. As a further example, any engaging device, even a balloon, may be used with some of the inventive aspects of the capture element and any capture element may be used with inventive aspects of the engaging device. Finally, the devices of the present invention may also be used in connection with simply controlling blood flow through an area and not necessarily with removal of an obstruction.

What is claimed is:

1. A method of removing an obstruction from a blood vessel, comprising the steps of:
   providing an obstruction removing device having a first obstruction removing element and a second obstruction removing element, the first and second obstruction removing elements both being movable from a collapsed position to an expanded position, the first and second obstruction removing elements being independently movable, the second obstruction removing element being a wire element;
   positioning the obstruction removing device in at least one catheter with the first and second obstruction removing elements in the collapsed position;
   advancing the catheter through the obstruction;
   moving the first obstruction removing element out of the catheter after the advancing step so that the obstruction removing element moves toward the expanded position;
   expanding the second obstruction removing element on a proximal side of the obstruction so that the obstruction is positioned between the first obstruction removing element and the expanded wire element of the second obstruction removing element; and
   engaging the obstruction by moving at least one of the first and second obstruction removing elements.

2. The method of claim 1, wherein:
   the providing step is carried out with the first and second obstruction removing elements both being elongate wire elements; and
   the expanding step is carried out with the second obstruction engaging element forming at least one coil when the wire is expanded, the first obstruction engaging element passing through the at least one coil of the second obstruction engaging element.

* * * * *